(12) United States Patent
Fleetham et al.

(10) Patent No.: US 11,834,459 B2
(45) Date of Patent: Dec. 5, 2023

(54) HOST MATERIALS FOR ELECTROLUMINESCENT DEVICES

(71) Applicant: Universal Display Corporation, Ewing, NJ (US)

(72) Inventors: Tyler Fleetham, Newtown, PA (US); Peter Wolohan, Princeton, NJ (US); Hsiao-Fan Chen, Lawrence Township, NJ (US)

(73) Assignee: Universal Display Corporation, Ewing, NJ (US)

( * ) Notice: Subject to any disclaimer, the term of this patent is extended or adjusted under 35 U.S.C. 154(b) by 865 days.

(21) Appl. No.: 16/682,126

(22) Filed: Nov. 13, 2019

(65) Prior Publication Data

US 2020/0190103 A1 Jun. 18, 2020

Related U.S. Application Data

(60) Provisional application No. 62/778,673, filed on Dec. 12, 2018.

(51) Int. Cl.
*C07D 495/04* (2006.01)
*C07D 519/00* (2006.01)
(Continued)

(52) U.S. Cl.
CPC ......... *C07D 495/04* (2013.01); *C07D 519/00* (2013.01); *H10K 85/654* (2023.02);
(Continued)

(58) Field of Classification Search
CPC ..... C07D 495/04; C07D 519/00; H01L 51/00; H01L 51/5221; H01L 51/0067; H01L 51/0072
See application file for complete search history.

(56) References Cited

U.S. PATENT DOCUMENTS 2,010,023 A 8/1935 Hothersall
4,769,292 A 9/1988 Tang
(Continued)

FOREIGN PATENT DOCUMENTS

CN 103313979 A 9/2013
CN 104926805 A 9/2015
(Continued)

OTHER PUBLICATIONS

Chun et al., caplus abstract of U.S. Pat. No. 9,067,947, 2015.*
Wong, Wai-Yeung, "Multifunctional Iridium Complexes Based on Carbazole Modules as Highly Efficient Electrophosphors," Angew. Chem. Int. Ed., 45:7800-7803 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode: an Isoindole Derivative," Chem. Mater., 15(16):3148-3151 (2003).
Okumoto, Kenji et al., "Green Fluorescent Organic Light-Emitting Device with External Quantum Efficiency of Nearly 10%," Appl. Phys. Lett., 89:063504-1-063504-3 (2006).
Paulose, Betty Marie Jennifer S, et al., "First Examples of Alkenyl Pyridines as Organic Ligands for Phosphorescent Iridium Complexes," Adv. Mater., 16(22):2003-2007 (2004).
(Continued)

*Primary Examiner* — Sun Jae Yoo
(74) *Attorney, Agent, or Firm* — Riverside Law LLP

(57) ABSTRACT

A compound of Formula I

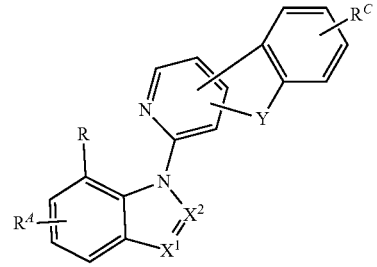

Formula I wherein
$X^1$ and $X^2$ are independently $CR^X$ or N, and at least one of $X^1$ or $X^2$ is $CR^X$;
Y is selected from the group consisting of O, S, Se, NR', BR', CR'R", and SiR'R";
R', and R" are each independently selected from the group consisting of alkyl, cycloalkyl, heteroalkyl, heterocycloalkyl, aryl, heteroaryl, and combinations thereof;
R is selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;
$R^A$, and $R^C$ each independently represent mono to the maximum allowable substitution, or no substitution; and
each $R^X$, $R^A$, and $R^C$ is independently a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof, and wherein any two substituents $R^X$, $R^A$, and $R^C$ may be optionally joined to form a ring, with the proviso that R does not join with $R^A$ to form a ring.

18 Claims, 2 Drawing Sheets

(51) Int. Cl.
- H01L 51/00 (2006.01)
- C07D 491/048 (2006.01)
- H10K 85/60 (2023.01)
- H10K 50/11 (2023.01)
- H10K 50/81 (2023.01)
- H10K 50/82 (2023.01)
- H10K 101/10 (2023.01)

(52) U.S. Cl.
CPC ....... H10K 85/657 (2023.02); H10K 85/6572 (2023.02); H10K 50/11 (2023.02); H10K 50/81 (2023.02); H10K 50/82 (2023.02); H10K 2101/10 (2023.02)

(56) References Cited

U.S. PATENT DOCUMENTS

| | | |
|---|---|---|
| 5,061,569 A | 10/1991 | Vanslyke |
| 5,247,190 A | 9/1993 | Friend |
| 5,703,436 A | 12/1997 | Forrest |
| 5,707,745 A | 1/1998 | Forrest |
| 5,834,893 A | 11/1998 | Bulovic |
| 5,844,363 A | 12/1998 | Gu |
| 6,013,982 A | 1/2000 | Thompson |
| 6,087,196 A | 7/2000 | Sturm |
| 6,091,195 A | 7/2000 | Forrest |
| 6,097,147 A | 8/2000 | Baldo |
| 6,294,398 B1 | 9/2001 | Kim |
| 6,303,238 B1 | 10/2001 | Thompson |
| 6,337,102 B1 | 1/2002 | Forrest |
| 6,468,819 B1 | 10/2002 | Kim |
| 6,528,187 B1 | 3/2003 | Okada |
| 6,687,266 B1 | 2/2004 | Ma |
| 6,835,469 B2 | 12/2004 | Kwong |
| 6,921,915 B2 | 7/2005 | Takiguchi |
| 7,087,321 B2 | 8/2006 | Kwong |
| 7,090,928 B2 | 8/2006 | Thompson |
| 7,154,114 B2 | 12/2006 | Brooks |
| 7,250,226 B2 | 7/2007 | Tokito |
| 7,279,704 B2 | 10/2007 | Walters |
| 7,332,232 B2 | 2/2008 | Ma |
| 7,338,722 B2 | 3/2008 | Thompson |
| 7,393,599 B2 | 7/2008 | Thompson |
| 7,396,598 B2 | 7/2008 | Takeuchi |
| 7,431,968 B1 | 10/2008 | Shtein |
| 7,445,855 B2 | 11/2008 | Mackenzie |
| 7,534,505 B2 | 5/2009 | Lin |
| 7,968,146 B2 | 6/2011 | Wagner |
| 8,409,729 B2 | 4/2013 | Zeng |
| 8,962,158 B2 | 2/2015 | Komori |
| 9,067,947 B2 * | 6/2015 | Lin ............... H01L 51/0061 |
| 10,593,890 B2 | 3/2020 | Zeng |
| 11,245,080 B2 | 2/2022 | Zeng |
| 2002/0034656 A1 | 3/2002 | Thompson |
| 2002/0121860 A1 | 9/2002 | Seo |
| 2002/0134984 A1 | 9/2002 | Igarashi |
| 2002/0158242 A1 | 10/2002 | Son |
| 2003/0104243 A1 | 6/2003 | Aziz |
| 2003/0132704 A1 | 7/2003 | Aziz |
| 2003/0137239 A1 | 7/2003 | Matsuura |
| 2003/0138657 A1 | 7/2003 | Li |
| 2003/0148142 A1 | 8/2003 | Fryd |
| 2003/0152802 A1 | 8/2003 | Tsuboyama |
| 2003/0162053 A1 | 8/2003 | Marks |
| 2003/0175553 A1 | 9/2003 | Thompson |
| 2003/0230980 A1 | 12/2003 | Forrest |
| 2004/0036077 A1 | 2/2004 | Ise |
| 2004/0137267 A1 | 7/2004 | Igarashi |
| 2004/0137268 A1 | 7/2004 | Igarashi |
| 2004/0164292 A1 | 8/2004 | Tung |
| 2004/0174116 A1 | 9/2004 | Lu |
| 2004/0263065 A1 | 12/2004 | Yeh |
| 2005/0025993 A1 | 2/2005 | Thompson |
| 2005/0089715 A1 | 4/2005 | Cosimbescu |
| 2005/0112407 A1 | 5/2005 | Ogasawara |
| 2005/0238919 A1 | 10/2005 | Ogasawara |
| 2005/0244673 A1 | 11/2005 | Satoh |
| 2005/0260441 A1 | 11/2005 | Thompson |
| 2005/0260449 A1 | 11/2005 | Walters |
| 2006/0008670 A1 | 1/2006 | Lin |
| 2006/0057423 A1 | 3/2006 | Steudel |
| 2006/0202194 A1 | 9/2006 | Jeong |
| 2006/0227081 A1 | 10/2006 | Joo |
| 2006/0240279 A1 | 10/2006 | Adamovich |
| 2006/0251923 A1 | 11/2006 | Lin |
| 2006/0263635 A1 | 11/2006 | Ise |
| 2006/0280965 A1 | 12/2006 | Kwong |
| 2007/0190359 A1 | 8/2007 | Knowles |
| 2007/0237982 A1 | 10/2007 | Inoue |
| 2007/0252516 A1 | 11/2007 | Kondakova |
| 2007/0278938 A1 | 12/2007 | Yabunouchi |
| 2008/0015355 A1 | 1/2008 | Schafer |
| 2008/0018221 A1 | 1/2008 | Egen |
| 2008/0106190 A1 | 5/2008 | Yabunouchi |
| 2008/0124572 A1 | 5/2008 | Mizuki |
| 2008/0220265 A1 | 9/2008 | Xia |
| 2008/0297033 A1 | 12/2008 | Knowles |
| 2009/0008605 A1 | 1/2009 | Kawamura |
| 2009/0009065 A1 | 1/2009 | Nishimura |
| 2009/0017330 A1 | 1/2009 | Iwakuma |
| 2009/0030202 A1 | 1/2009 | Iwakuma |
| 2009/0039776 A1 | 2/2009 | Yamada |
| 2009/0045730 A1 | 2/2009 | Nishimura |
| 2009/0045731 A1 | 2/2009 | Nishimura |
| 2009/0101870 A1 | 4/2009 | Prakash |
| 2009/0108737 A1 | 4/2009 | Kwong |
| 2009/0115316 A1 | 5/2009 | Zheng |
| 2009/0165846 A1 | 7/2009 | Johannes |
| 2009/0167162 A1 | 7/2009 | Lin |
| 2009/0179554 A1 | 7/2009 | Kuma |
| 2009/0302743 A1 | 12/2009 | Kato |
| 2010/0012931 A1 | 1/2010 | Kato |
| 2010/0184942 A1 | 7/2010 | Chen |
| 2010/0187977 A1 | 7/2010 | Kai |
| 2010/0187984 A1 | 7/2010 | Lin |
| 2010/0237334 A1 | 9/2010 | Ma |
| 2011/0062429 A1 | 3/2011 | Kai |
| 2011/0278552 A1 | 11/2011 | Numata |
| 2012/0001158 A1 | 1/2012 | Asari |
| 2012/0001165 A1 | 1/2012 | Komori |
| 2012/0056171 A1 | 3/2012 | Kim |
| 2012/0104940 A1 | 5/2012 | Shin |
| 2012/0175598 A1 | 7/2012 | Balaganesan |
| 2012/0205640 A1 | 8/2012 | Kai |
| 2013/0026452 A1 | 1/2013 | Kottas |
| 2013/0119354 A1 | 5/2013 | Ma |
| 2013/0248849 A1 | 9/2013 | Feldman |
| 2014/0034914 A1 | 2/2014 | Saki |
| 2014/0054564 A1 | 2/2014 | Kim |
| 2014/0077179 A1 | 3/2014 | Shin |
| 2014/0084273 A1 | 3/2014 | Nakayama |
| 2014/0124756 A1 | 5/2014 | Yokoyama |
| 2014/0225046 A1 | 8/2014 | Jatsch |
| 2014/0374711 A1 | 12/2014 | Cho |
| 2015/0021556 A1 | 1/2015 | Xia |
| 2015/0041785 A1 | 2/2015 | Sannomiya |
| 2015/0053938 A1 | 2/2015 | Zeng |
| 2015/0060796 A1 | 3/2015 | Kim |
| 2015/0171340 A1 | 6/2015 | Seungjae |
| 2015/0179949 A1 | 6/2015 | Miyata |
| 2015/0179955 A1 | 6/2015 | Miyata |
| 2015/0228909 A1 | 8/2015 | Kim |
| 2015/0228911 A1 | 8/2015 | Kim |
| 2015/0236262 A1 | 8/2015 | Cho |
| 2015/0255726 A1 | 9/2015 | Kawamura |
| 2015/0318487 A1 | 11/2015 | Ito |
| 2015/0380662 A1 | 12/2015 | Kim |
| 2016/0005979 A1 | 1/2016 | Kim |
| 2016/0111663 A1 | 4/2016 | Kim |
| 2016/0118590 A1 | 4/2016 | Ito |
| 2016/0133844 A1 | 5/2016 | Kim |
| 2016/0163995 A1 | 6/2016 | Kang |
| 2016/0225992 A1 | 8/2016 | Ito |
| 2016/0276596 A1 | 9/2016 | Jang |

(56) References Cited

U.S. PATENT DOCUMENTS

| | | | |
|---|---|---|---|
| 2016/0293853 A1 | 10/2016 | Zeng |
| 2017/0025618 A1 | 1/2017 | Zheng |
| 2017/0047527 A1 | 2/2017 | Lee |
| 2017/0069847 A1 | 3/2017 | Kim |
| 2017/0069848 A1 | 3/2017 | Zeng |
| 2017/0098784 A1 | 4/2017 | Kim |
| 2017/0263869 A1 | 9/2017 | Tada |
| 2017/0271598 A1 | 9/2017 | Zeng |

FOREIGN PATENT DOCUMENTS

| | | | |
|---|---|---|---|
| CN | 106543205 A | 3/2017 |
| CN | 107075363 A | 8/2017 |
| EP | 0650955 | 5/1995 |
| EP | 0908787 | 4/1999 |
| EP | 1238981 | 9/2002 |
| EP | 1725079 | 11/2006 |
| EP | 2034538 | 3/2009 |
| EP | 2551932 | 1/2013 |
| EP | 2617712 | 7/2013 |
| EP | 2977378 | 1/2016 |
| JP | 2003300980 | 10/2003 |
| JP | 200511610 | 1/2005 |
| JP | 2007123392 | 5/2007 |
| JP | 2007254297 | 10/2007 |
| JP | 2008074939 A | 4/2008 |
| JP | 2010135467 | 6/2010 |
| JP | 2012049518 | 3/2012 |
| JP | 2012056880 A | 3/2012 |
| JP | 2014077046 A | 5/2014 |
| KR | 20100082049 | 7/2010 |
| KR | 20100131745 A | 12/2010 |
| KR | 20110011579 | 2/2011 |
| KR | 20110066766 | 6/2011 |
| KR | 201110102055 A | 9/2011 |
| KR | 20120021203 | 3/2012 |
| KR | 20130025268 | 3/2013 |
| KR | 20130132226 | 12/2013 |
| KR | 20140001568 | 1/2014 |
| KR | 20140009019 | 1/2014 |
| KR | 20140023589 A | 2/2014 |
| KR | 20140127705 | 11/2014 |
| KR | 20140134947 | 11/2014 |
| KR | 20140145355 A | 12/2014 |
| KR | 20150012835 | 2/2015 |
| KR | 20150133998 A | 12/2015 |
| TW | 201114743 A | 5/2011 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2004111066 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006067074 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006115301 | 11/2006 |
| WO | 2006121811 | 11/2006 |
| WO | 2006128800 | 12/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008044723 | 4/2008 |
| WO | 2008056746 | 5/2008 |
| WO | 2008057394 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 A2 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2009148016 | 12/2009 |
| WO | 2009148062 | 12/2009 |
| WO | 2010011390 | 1/2010 |
| WO | 2010107244 | 9/2010 |
| WO | 2010111175 | 9/2010 |
| WO | 2010126234 | 11/2010 |
| WO | 2012029253 | 3/2012 |
| WO | 2012039561 | 3/2012 |
| WO | 2012087007 | 6/2012 |
| WO | 2013027902 | 2/2013 |
| WO | 2013041176 | 3/2013 |
| WO | 2013109045 | 7/2013 |
| WO | 2013154325 | 10/2013 |
| WO | 2013154325 A1 | 10/2013 |
| WO | 2013162284 | 10/2013 |
| WO | 2013165189 | 11/2013 |
| WO | 2013183851 | 12/2013 |
| WO | 2014010910 | 1/2014 |
| WO | 2014044722 | 3/2014 |
| WO | 2014061546 | 4/2014 |
| WO | 2014061961 | 4/2014 |
| WO | 2014088285 | 6/2014 |
| WO | 2014129846 | 8/2014 |
| WO | 2014142467 | 9/2014 |
| WO | 2014142472 | 9/2014 |
| WO | 2014157708 | 10/2014 |
| WO | 2014200244 | 12/2014 |
| WO | 2014208755 | 12/2014 |
| WO | 2015009102 | 1/2015 |
| WO | 2015022835 A1 | 2/2015 |
| WO | 2015022987 | 2/2015 |
| WO | 2015053524 A1 | 4/2015 |
| WO | 2015063046 | 5/2015 |
| WO | 2015099507 | 7/2015 |
| WO | 2015108325 | 7/2015 |
| WO | 2015111848 | 7/2015 |
| WO | 2015152644 | 10/2015 |
| WO | 2015167259 | 11/2015 |
| WO | 2017056052 | 4/2017 |
| WO | 2014069637 | 2/2020 |

OTHER PUBLICATIONS

Tang, C.W and VanSlyke, S.A., "Organic Electroluminescent Diodes," Appl. Phys. Lett., 51(12):913-915 (1987).
T. Ostergard et al., "Langmuir-Blodgett Light-Emitting Diodes Of Poly(3-Hexylthiophene): Electro-Optical Characteristics Related to Structure," Synthetic Metals, 87:171-177 (1997).
Tung, Yung-Liang et al., "Organic Light-Emitting Diodes Based on Charge-Neutral Ru II PHosphorescent Emitters," Adv. Mater., 17(8):1059-1064 (2005).
Van Slyke, S. A. et al., "Organic Electroluminescent Devices with Improved Stability," Appl. Phys. Lett, 69(15 ):2160-2162 (1996).
Wong, Keith Man-Chung et al., "A Novel Class of Phosphorescent Gold(III) Alkynyl-Based Organic Light-Emitting Devices with Tunable Colour," Chem. Commun., 2906-2908 (2005).
Adachi, Chihaya et al., "Organic Electroluminescent Device Having a Hole Conductor as an Emitting Layer," Appl. Phys. Lett., 55(15):1489-1491 (1989).

(56) References Cited

OTHER PUBLICATIONS

Baldo et al., "Highly Efficient Phosphorescent Emission from Organic Electroluminescent Devices," Nature, vol. 395,151-154, (1998).
GAO, Zhiqiang et al., "Bright-Blue Electroluminescence From a Silyl-Substituted ter-(phenylene- vinylene) derivative," Appl. Phys. Lett., 74(6):865-867 (1999).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Wang, Y. et al., "Highly Efficient Electroluminescent Materials Based on Fluorinated Organometallic Iridium Compounds," Appl. Phys. Lett., 79(4):449-451 (2001).
Kwong, Raymond C. et al., "High Operational Stability of Electrophosphorescent Devices," Appl. Phys. Lett., 81(1):162-164 (2002).
Holmes, R.J. et al., "Blue Organic Electrophosphorescence Using Exothermic Host-Guest Energy Transfer," Appl. Phys. Lett., 82(15):2422-2424 (2003).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Sun, Yiru and Forrest, Stephen R., "High-Efficiency White Organic Light Emitting Devices with Three Separate Phosphorescent Emission Layers," Appl. Phys. Lett., 91 :263503-1-263503-3 (2007).
Adachi, Chihaya et al., "High-Efficiency Red Electrophosphorescence Devices," Appl. Phys. Lett., 78(11):1622-1624 (2001).
Hamada, Yuji et al., "High Luminance in Organic Electroluminescent Devices with Bis(10-hydroxybenzo[h]quinolinato)beryllium as an Emitter," Chem. Lett., 905-906 (1993).
Nishida, Jun-ichi et al., "Preparation, Characterization, and Electroluminescence Characteristics of a-Diimine-type Platinum(II) Complexes with Perfluorinated Phenyl Groups as Ligands," Chem. Lett., 34(4):592-593 (2005).
Baldo et al., "Very high-efficiency green organic light-emitting devices based on electrophosphorescence," Appl. Phys. Lett., vol. 75, No. 3, 4-6 (1999).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
NIU, Yu-Hua et al., "Highly Efficient Electrophosphorescent Devices with Saturated Red Emission from a Neutral Osmium Complex," Chem. Mater., 17(13):3532-3536 (2005).
Lo, Shih-Chun et al., "Blue Phosphorescence from Iridium(III) Complexes at Room Temperature," Chem. Mater., 18(21):5119-5129 (2006).
Takizawa, Shin-ya et al., "Phosphorescent Iridium Complexes Based on 2-Phenylimidazo[1,2- a]pyridine Ligands: Tuning of Emission Colortoward the Blue Region and Application to Polymer Light-Emitting Devices," Inorg. Chem., 46(10):4308-4319 (2007).
Lamansky, Sergey et al., "Synthesis and Characterization of Phosphorescent Cyclometalated Iridium Complexes," Inorg. Chem., 40(7):1704-1711 (2001).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Noda, Tetsuya and Shirota,Yasuhiko, "5,6-Bis(dinnesitylboryl)-2,2'-bithiophene and 5,5"-Bis(dimesitylboryl)-2,240 :5',2"-terthiophene as a Novel Family of Electron-Transporting Amorphous Molecular Materials," J. Am. Chem. Soc., 120 (37):9714-9715 (1998).
Sakamoto, Youichi et al., "Synthesis, Characterization, and Electron-Transport Property of Perfluorinated Phenylene Dendrimers," J. Am. Chem. Soc, 122(8):1832-1833 (2000).
Adachi, Chihaya et al., "Nearly 100% Internal Phosphorescence Efficiency in an Organic Light Emitting Device," J. Appl. Phys., 90(10):5048-5051 (2001).
Shirota, Yasuhiko et al., "Starburst Molecules Based on p-Electron Systems as Materials for Organic Electroluminescent Devices," Journal of Luminescence, 72-74:985-991 (1997).
Inada, Hiroshi and SHIROTA, Yasuhiko, "1,3,5-Tris[4-(diphenylamino)phenyl]benzene and its Methylsubstituted Derivatives as a Novel Class of Amorphous Molecular Materials," J. Mater. Chem., 3(3):519-320 (1993).
Kido, Junji et al.,"1,2,4-Triazole Derivative as an Electron Transport Layer in Organic Electroluminescent Devices," Jpn. J. Appl. Phys., 32:L917-L920 (1993).
GUO, Tzung-Fang et al., "Highly Efficient Electrophosphorescent Polymer Light-Emitting Devices," Organic Electronics, 1:15-20 (2000).
Palilis, Leonidas C., "High Efficiency Molecular Organic Light-Emitting Diodes Based On Silole Derivatives And Their Exciplexes," Organic Electronics, 4:113-121 (2003).
Ikeda, Hisao et al., "P-185: Low-Drive-Voltage OLEDs with a Buffer Layer Having Molybdenum Oxide," SID Symposium Digest, 37:923-926 (2006).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Salbeck, J. et al., "Low Molecular Organic Glasses for Blue Electroluminescence," Synthetic Metals, 91:209-215 (1997).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Yoshida, Kei et al., Machine translation of JP-2012056880-A (2012) pp. 1-19. (Year: 2012).
Machine translation of KR2014/0134947A (Year: 2014).
Office Action (Notice of Allowance and Fees Due (PTOL-85)) dated Jun. 16, 2022 for U.S. Appl. No. 15/283,982 (pp. 1-11).
Park Seong JE et al., machine translation of WO-2014142472-A1, pp. 1-25. (Year: 2014) (25 Pages).
Merriam-Webster definition of "single"("single." Merriam-Webster.com. Merriam-Webster, n.d. Web. Dec. 23, 2019). (Year: 2019) (2 pages).
Chae Mi Young et al., machine translation of KR-20110102055-A (2011) pp. 1-69. (Year: 2011).
Kim et al., Machine translation of WO-2014142472-A1 (2014) pp. 1-25. (Year: 2014).
Tanaka et al., machine translation of WO-2014208755-A1 (2014) pp. 1-78. (Year: 2014).

* cited by examiner

HOST MATERIALS FOR ELECTROLUMINESCENT DEVICES

CROSS-REFERENCE TO RELATED APPLICATIONS

This application claims priority under 35 U.S.C. § 119(e) to U.S. Provisional Application No. 62/778,673, filed Dec. 12, 2018, the entire contents of which are incorporated herein by reference.

FIELD

The present invention relates to compounds for use as hosts and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted Ir(ppy)$_3$, which has the following structure:

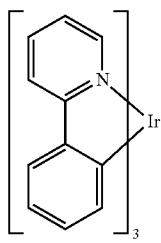

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY

A compound of Formula I

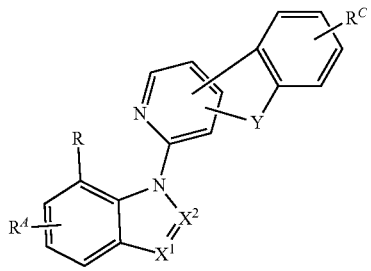

Formula I wherein
$X^1$ and $X^2$ are independently $CR^X$ or N, and at least one of $X^1$ or $X^2$ is $CR^X$;
Y is selected from the group consisting of O, S, Se, NR', BR', CR'R", and SiR'R";
R', and R" are each independently selected from the group consisting of alkyl, cycloalkyl, heteroalkyl, heterocycloalkyl, aryl, heteroaryl, and combinations thereof;
R is selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;
$R^A$, and $R^C$ each independently represent mono to the maximum allowable substitution, or no substitution; and
each $R^X$, $R^A$, and $R^C$ is independently a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof, and wherein any two substituents $R^X$, $R^A$, and $R^C$ may be optionally joined to form a ring, with the proviso that R does not join with $R^A$ to form a ring.

An OLED comprising the compound of the present disclosure in an organic layer therein is also disclosed.

A consumer product comprising the OLED is also disclosed.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
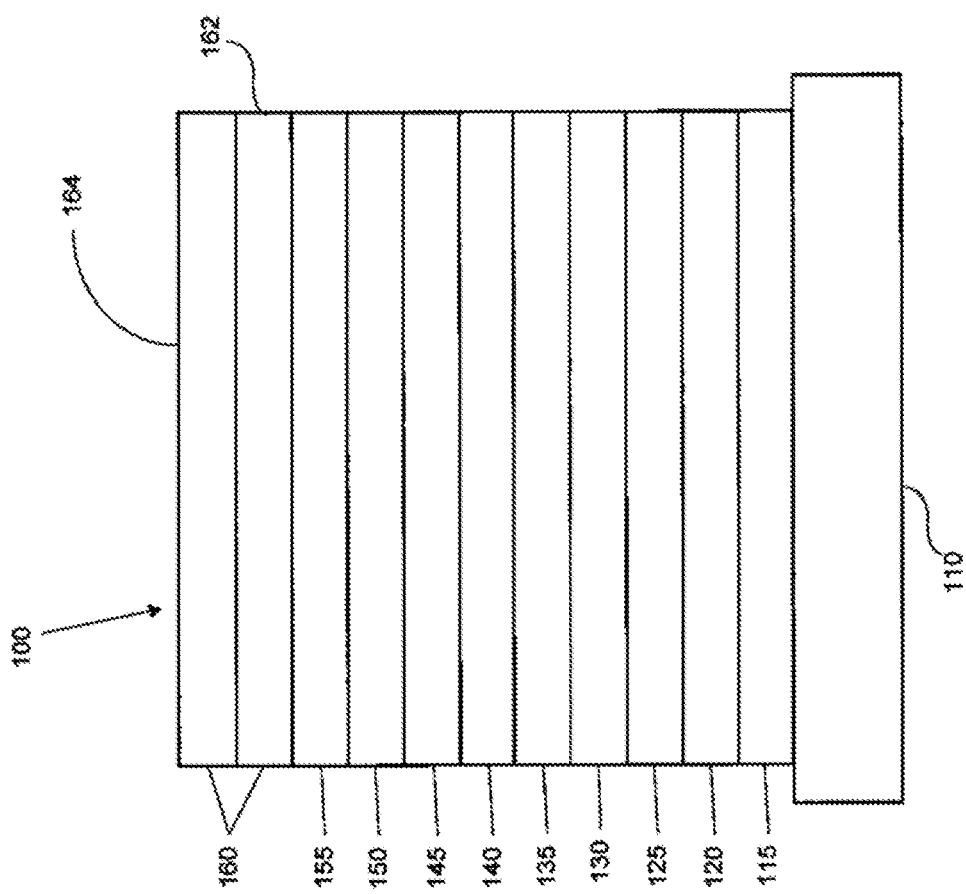
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
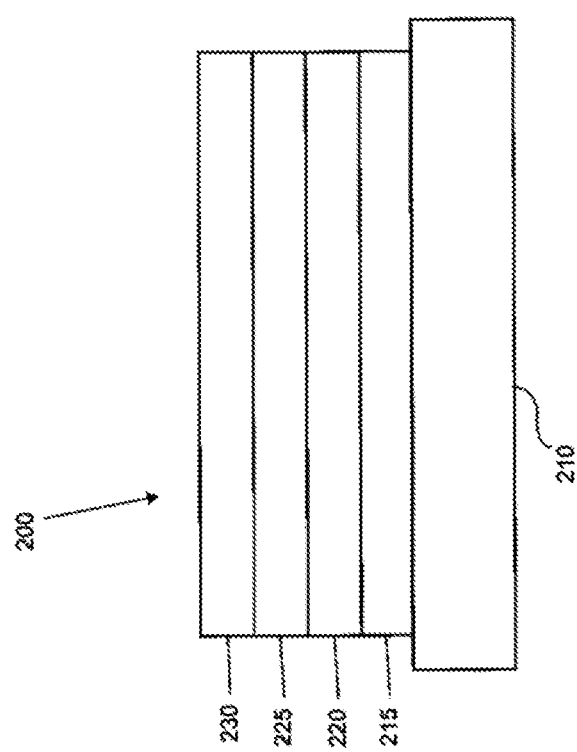
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms "halo," "halogen," or "halide" as used interchangeably and refer to fluorine, chlorine, bromine, and iodine.

The term "acyl" refers to a substituted carbonyl radical (C(O)—$R_s$).

The term "ester" refers to a substituted oxycarbonyl (—O—C(O)—$R_s$ or —C(O)—O—$R_s$) radical.

The term "ether" refers to an —OR radical.

The terms "sulfanyl" or "thio-ether" are used interchangeably and refer to a —$SR_s$ radical.

The term "sulfinyl" refers to a —S(O)—$R_s$ radical.

The term "sulfonyl" refers to a —$SO_2$—$R_s$ radical.

The term "phosphino" refers to a —$P(R_s)_3$ radical, wherein each $R_s$ can be same or different.

The term "silyl" refers to a —$Si(R_s)_3$ radical, wherein each $R_s$ can be same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo[3.1.1]heptyl, spiro[4.5]decyl, spiro[5.5]undecyl, adamantyl, and the like. Additionally, the cycloalkyl group may be optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group is optionally substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si and Se, preferably, O, S or N. Preferred alkenyl, cycloalkenyl, or heteroalkenyl groups are those containing two to fifteen carbon atoms. Additionally, the alkenyl, cycloalkenyl, or heteroalkenyl group is optionally substituted.

The term "alkynyl" refers to and includes both straight and branched chain alkyne radicals. Preferred alkynyl groups are those containing two to fifteen carbon atoms. Additionally, the alkynyl group is optionally substituted.

The terms "aralkyl" or "arylalkyl" are used interchangeably and refer to an alkyl group that is substituted with an aryl group. Additionally, the aralkyl group is optionally substituted.

The term "heterocyclic group" refers to and includes aromatic and non-aromatic cyclic radicals containing at least one heteroatom. Optionally the at least one heteroatom is selected from O, S, N, P, B, Si and Se, preferably, O, S or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" refers to and includes both single-ring hetero-aromatic groups and polycyclic aromatic ring systems that include at least one heteroatom. The heteroatoms include, but are not limited to O, S, N, P, B, Si and Se. In many instances, O, S or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted or substituted with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

In some instances, the preferred general substituents are selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

In some instances, the preferred general substituents are selected from the group consisting of deuterium, fluorine, alkyl, cycloalkyl, alkoxy, aryloxy, amino, silyl, aryl, heteroaryl, sulfanyl, and combinations thereof.

In yet other instances, the more preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R^1$ represents mono-substitution, then one $R^1$ must be other than H (i.e., a substitution). Similarly, when $R^1$ represents di-substitution, then two of $R^1$ must be other than H. Similarly, when $R^1$ represents no substitution, $R^1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. US 2011/0037057, which are hereby incorporated by reference in their entireties, describe the making of deuterium-substituted organometallic complexes. Further reference is made to Ming Yan, et al., *Tetrahedron* 2015, 71, 1425-30 and Atzrodt et al., *Angew. Chem. Int. Ed. (Reviews)* 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2,2' positions in a biphenyl, or 1,8 position in a naphthalene, as long as they can form a stable fused ring system.

In one aspect, the present invention includes a compound of Formula I:

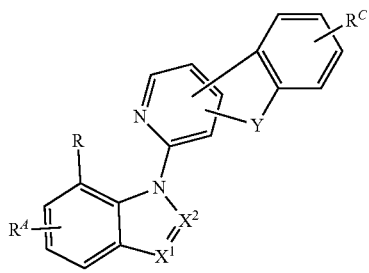

Formula I wherein $X^1$ and $X^2$ are independently $CR^X$ or N, and at least one of $X^1$ or $X^2$ is $CR^X$;

Y is selected from the group consisting of O, S, Se, NR', BR', CR'R", and SiR'R";

R', and R" are each independently selected from the group consisting of alkyl, cycloalkyl, heteroalkyl, heterocycloalkyl, aryl, heteroaryl, and combinations thereof;

R is selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;

$R^A$, and $R^C$ each independently represent mono to the maximum allowable substitution, or no substitution; and each $R^X$, $R^A$, and $R^C$ is independently a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof, and wherein any two substituents $R^X$, $R^A$, and $R^C$ may be optionally joined to form a ring, with the proviso that R does not join with $R^A$ to form a ring.

In one embodiment, each $R^X$, $R^A$, and $R^C$ is independently a hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

In one embodiment, each $R^A$ is H.

In one embodiment, each $R^C$ is H.

In one embodiment, when any two substituents $R^X$, $R^A$, or $R^C$ are optionally joined to form a ring, the ring is optionally substituted with a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof, and wherein any two substituents may be optionally joined to form a ring.

In one embodiment, the compound is Formula II

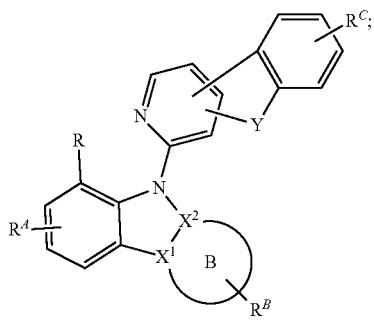

wherein ring B is a 5-membered or 6-membered heterocyclic or carbocyclic ring;

$R^B$ represents mono to the maximum allowable substitution, or no substitution; and $R^B$ is a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof, and wherein any two substituents of $R^B$ may be optionally joined to form a ring.

In one embodiment, R is a substituted or unsubstituted aryl or heteroaryl. In one embodiment, R comprises a chemical group selected from the group consisting of carbazole, aza-carbazole, dibenzofuran, aza-dibenzofuran, dibenzothiophene, aza-dibenzothiophene, benzene, pyrimidine, and triazine.

In one embodiment, Y is O or S.

In one embodiment, $X^1$ is N and $X^2$ is $CR^X$. In one embodiment, $X^1$ and $X^2$ are both $CR^X$.

In one embodiment, ring B is a 5-membered ring. In one embodiment, ring B is a 6-membered ring.

In one embodiment, two adjacent $R^B$ substituents join to form a 5-membered or 6-membered aromatic ring that is fused to ring B.

In one embodiment, each $R^B$ is H.

In one embodiment, the compound is selected from the group consisting of

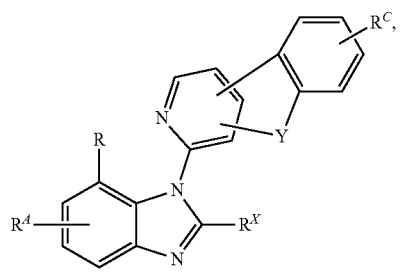

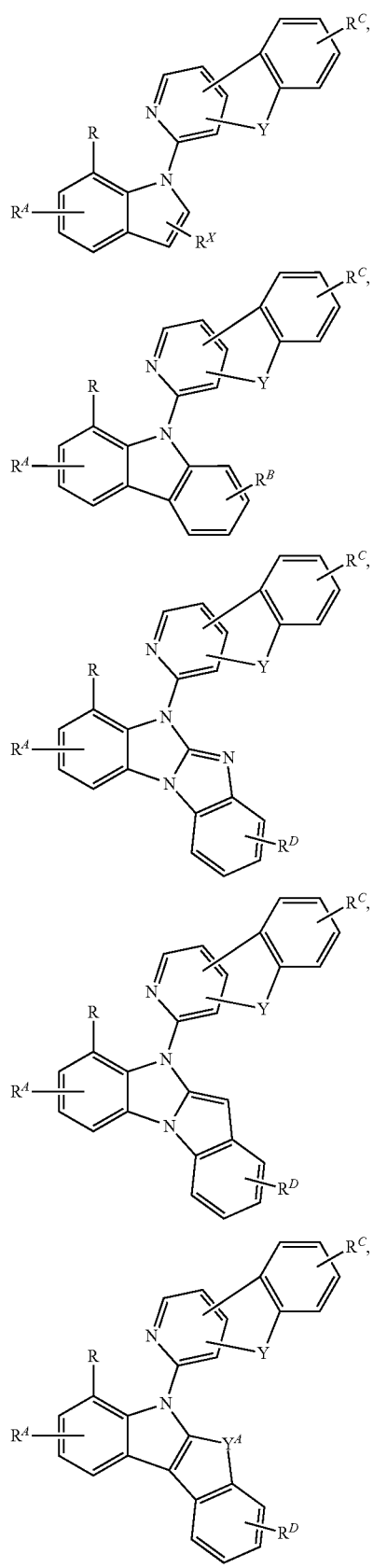
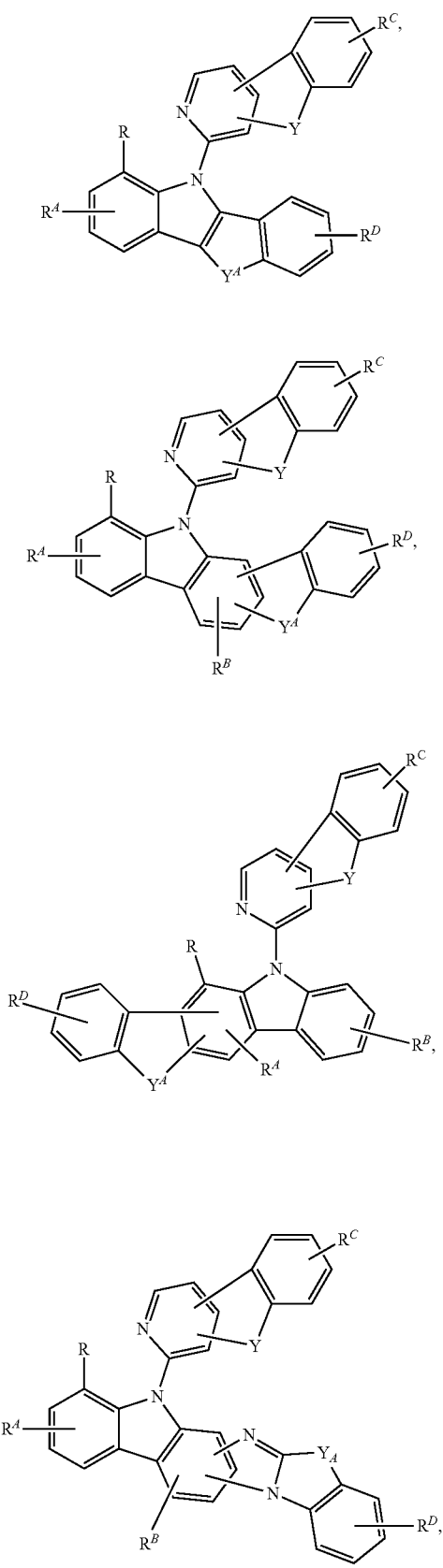

-continued
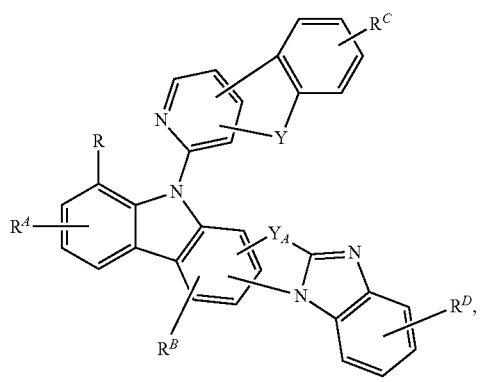
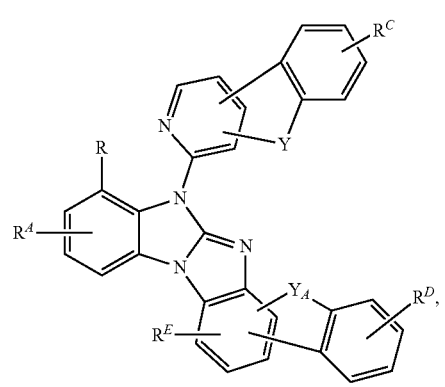
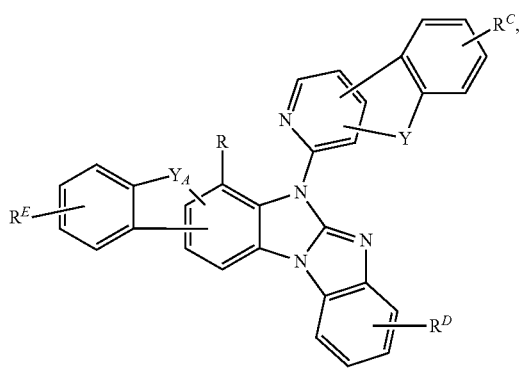
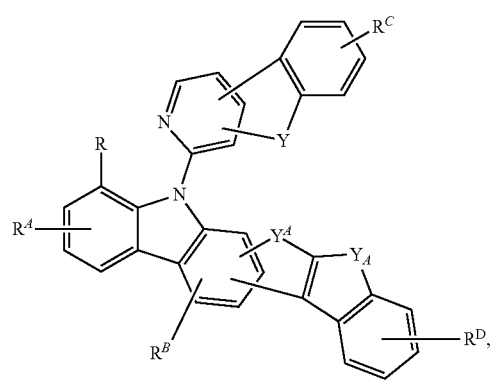
-continued
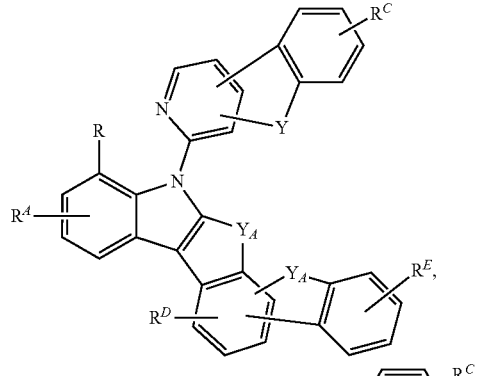
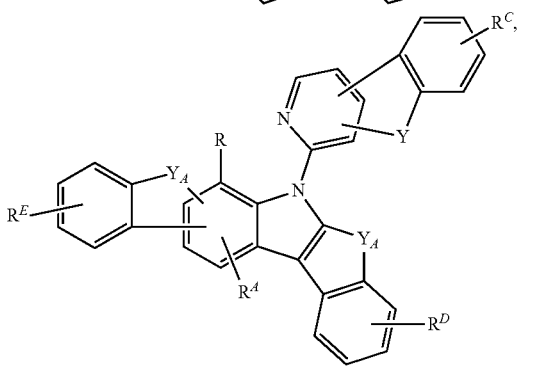
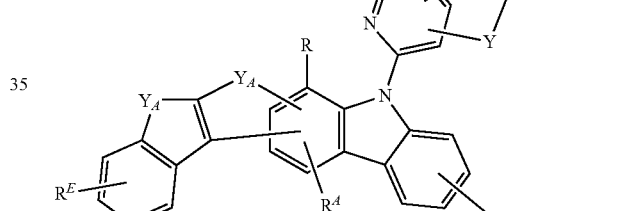
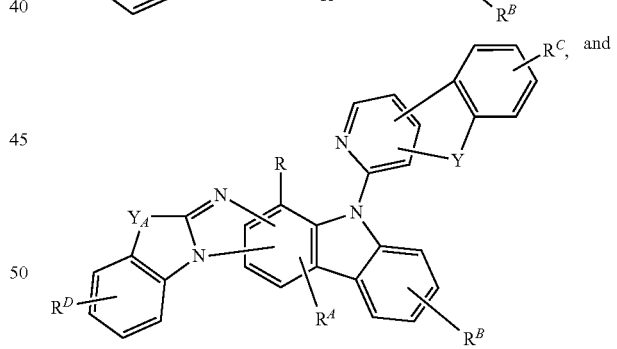
and
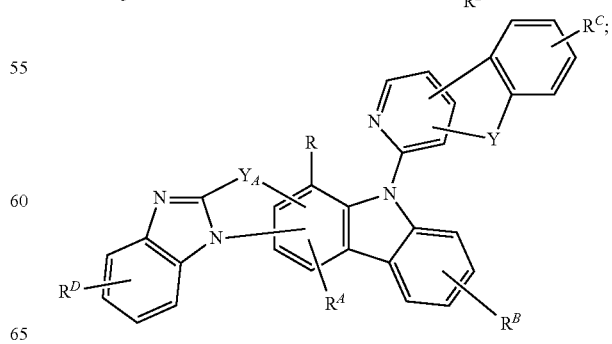

wherein
each $Y_A$ is selected from the group consisting of O, S, Se, NR', CR'R", and SiR'R"; $R^D$ and $R^E$ independently represent mono to the maximum allowable substitution, or no substitution; and
each $R^D$ and $R^E$ is independently a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof, and any two substituents $R^D$ or $R^E$ may be optionally joined to form a ring.

In one embodiment, the compound is Compound X selected from the group consisting of

| Structure | $R_1$, $R_2$, Ar | x equal to | Compound x |
|---|---|---|---|
| (indole structure) | Ar = Ai<br>$R_1$ = Rj<br>i and j are each independently an integer from 1 to 50 | 50(i − 1) + j | Compound 1-2500 |
| (carbazole structure) | Ar = Ai<br>$R_1$ = Rj<br>i and j are each independently an integer from 1 to 50 | 50(i − 1) + j + 2500 | Compound 2501-5000 |
| (benzimidazole fused structure) | Ar = Ai<br>$R_1$ = Rj<br>i and j are each independently an integer from 1 to 50 | 50(i − 1) + j + 5000 | Compound 5001-7500 |
| (indolo-fused structure) | Ar = Ai<br>$R_1$ = Rj<br>i and j are each independently an integer from 1 to 50 | 50(i − 1) + j + 7500 | Compound 7501-10000 |
| (benzofuran-indole structure) | Ar = Ai<br>$R_1$ = Rj<br>i and j are each independently an integer from 1 to 50 | 50(i − 1) + j + 10000 | Compound 10001-12500 |
| (dibenzofuran-indole structure) | Ar = Ai<br>$R_1$ = Rj<br>i and j are each independently an integer from 1 to 50 | 50(i − 1) + j + 12500 | Compound 12501-15000 |

-continued

| Structure | $R_1$, $R_2$, Ar | x equal to | Compound x |
|---|---|---|---|
| (structure) | Ar = Ai<br>$R_1$ = Rj<br>i and j are each independently an integer from 1 to 50 | 50(i − 1) + j + 15000 | Compound 15001-17500 |
| (structure) | Ar = Ai<br>$R_1$ = Rj<br>i and j are each independently an integer from 1 to 50 | 50(i − 1) + j + 17500 | Compound 17501-20000 |
| (structure) | Ar = Ai<br>$R_1$ = Rj<br>i and j are each independently an integer from 1 to 50 | 50(i − 1) + j + 20000 | Compound 20001-22500 |
| (structure) | Ar = Ai<br>$R_1$ = Rj<br>i and j are each independently an integer from 1 to 50 | 50(i − 1) + j + 22500 | Compound 22501-25000 |
| (structure) | Ar = Ai<br>$R_1$ = Rj<br>i and j are each independently an integer from 1 to 50 | 50(i − 1) + j + 25000 | Compound 25001-27500 |
| (structure) | Ar = Ai<br>$R_1$ = Rj<br>i and j are each independently an integer from 1 to 50 | 50(i − 1) + j + 27500 | Compound 27501-30000 |

-continued

| Structure | R₁, R₂, Ar | x equal to | Compound x |
|---|---|---|---|
|  | Ar = Ai<br>R₁ = Rj<br>i and j are each independently an integer from 1 to 50 | 50(i − 1) + j + 30000 | Compound 30001-32500 |
|  | Ar = Ai<br>R₁ = Rj<br>i and j are each independently an integer from 1 to 50 | 50(i − 1) + j + 32500 | Compound 32501-35000 |
|  | Ar = Ai<br>R₁ = Rj<br>i and j are each independently an integer from 1 to 50 | 50(i − 1) + j + 35000 | Compound 35001-37500 |
|  | Ar = Ai<br>R₁ = Rj<br>i and j are each independently an integer from 1 to 50 | 50(i − 1) + j + 37500 | Compound 37501-40000 |
|  | Ar = Ai<br>R₁ = Rj<br>i and j are each independently an integer from 1 to 50 | 50(i − 1) + j + 40000 | Compound 40001-42500 |
|  | Ar = Ai<br>R₁ = Rj<br>i and j are each independently an integer from 1 to 50 | 50(i − 1) + j + 42500 | Compound 42501-45000 |

-continued

| Structure | R₁, R₂, Ar | x equal to | Compound x |
|---|---|---|---|
| (structure) | Ar = Ai<br>R₁ = Rj<br>i and j are each independently an integer from 1 to 50 | 50(i − 1) + j + 45000 | Compound 45001-47500 |
| (structure) | Ar = Ai<br>R₁ = Rj<br>i and j are each independently an integer from 1 to 50 | 50(i − 1) + j + 47500 | Compound 47501-50000 |
| (structure) | Ar = Ai<br>R₁ = Rj<br>R₂ = Rk<br>i, j, and k are each independently an integer from 1 to 50 | 2500(i − 1) + 50(j − 1) + k + 50000 | Compound 50001-175000 |
| (structure) | Ar = Ai<br>R₁ = Rj<br>R₂ = Rk<br>i, j, and k are each independently an integer from 1 to 50 | 2500(i − 1) + 50(j − 1) + k + 175000 | Compound 175001-300000 |
| (structure) | Ar = Ai<br>R₁ = Rj<br>R₂ = Rk<br>i, j, and k are each independently an integer from 1 to 50 | 2500(i − 1) + 50(j − 1) + k + 300000 | Compound 300001-425000 |
| (structure) | Ar = Ai<br>R₁ = Rj<br>R₂ = Rk<br>i, j, and k are each independently an integer from 1 to 50 | 2500(i − 1) + 50(j − 1) + k + 425000 | Compound 425001-550000 |

-continued

| Structure | R₁, R₂, Ar | x equal to | Compound x |
|---|---|---|---|
| (structure) | Ar = Ai<br>R₁ = Rj<br>R₂ = Rk<br>i, j, and k are each independently an integer from 1 to 50 | 2500(i − 1) + 50(j − 1) + k + 550000 | Compound 550001-675000 |
| (structure) | Ar = Ai<br>R₁ = Rj<br>R₂ = Rk<br>i, j, and k are each independently an integer from 1 to 50 | 2500(i − 1) + 50(j − 1) + k + 675000 | Compound 675001-800000 |
| (structure) | Ar = Ai<br>R₁ = Rj<br>R₂ = Rk<br>i, j, and k are each independently an integer from 1 to 50 | 2500(i − 1) + 50(j − 1) + k + 800000 | Compound 800001-925000 |
| (structure) | Ar = Ai<br>R₁ = Rj<br>R₂ = Rk<br>i, j, and k are each independently an integer from 1 to 50 | 2500(i − 1) + 50(j − 1) + k + 925000 | Compound 925001-1050000 |
| (structure) | Ar = Ai<br>R₁ = Rj<br>R₂ = Rk<br>i, j, and k are each independently an integer from 1 to 50 | 2500(i − 1) + 50(j − 1) + k + 1050000 | Compound 1050001-1175000 |
| (structure) | Ar = Ai<br>R₁ = Rj<br>R₂ = Rk<br>i, j, and k are each independently an integer from 1 to 50 | 2500(i − 1) + 50(j − 1) + k + 1175000 | Compound 1175001-1300000 |

| Structure | $R_1, R_2, Ar$ | x equal to | Compound x |
|---|---|---|---|
| (structure) | Ar = Ai<br>$R_1$ = Rj<br>$R_2$ = Rk<br>i, j, and k are each independently an integer from 1 to 50 | 2500(i − 1) + 50(j − 1) + k + 1300000 | Compound 1300001-1425000 |
| (structure) | Ar = Ai<br>$R_1$ = Rj<br>$R_2$ = Rk<br>i, j, and k are each independently an integer from 1 to 50 | 2500(i − 1) + 50(j − 1) + k + 1425000 | Compound 1425001-1550000 |
| (structure) | Ar = Ai<br>$R_1$ = Rj<br>$R_2$ = Rk<br>i, j, and k are each independently an integer from 1 to 50 | 2500(i − 1) + 50(j − 1) + k + 1550000 | Compound 1550001-1675000 |
| (structure) | Ar = Ai<br>$R_1$ = Rj<br>$R_2$ = Rk<br>i, j, and k are each independently an integer from 1 to 50 | 2500(i − 1) + 50(j − 1) + k + 1675000 | Compound 1675001-1800000 |
| (structure) | Ar = Ai<br>$R_1$ = Rj<br>$R_2$ = Rk<br>$R_3$ = Rm<br>i, j, k and m are each independently an integer from 1 to 50 | 125000(i − 1) + 2500(j − 1) + 50(k − 1) + m + 1800000 | Compound 1800001-8050000 |
| (structure) | Ar = Ai<br>$R_1$ = Rj<br>$R_2$ = Rk<br>$R_3$ = Rm<br>i, j, k and m are each independently an integer from 1 to 50 | 125000(i − 1) + 2500(j − 1) + 50(k − 1) + m + 8050000 | Compound 8050001-14300000 |

-continued

| Structure | R₁, R₂, Ar | x equal to | Compound x |
|---|---|---|---|
| (structure) | Ar = Ai<br>R₁ = Rj<br>R₂ = Rk<br>i, j, and k are each independently an integer from 1 to 50 | 2500(i − 1) + 50(j − 1) + k + 14300000 | Compound 14300001-14425000 |
| (structure) | Ar = Ai<br>R₁ = Rj<br>R₂ = Rk<br>i, j, and k are each independently an integer from 1 to 50 | 2500(i − 1) + 50(j − 1) + k + 14425000 | Compound 14425001-14550000 |
| (structure) | Ar = Ai<br>R₁ = Rj<br>R₂ = Rk<br>i, j, and k are each independently an integer from 1 to 50 | 2500(i − 1) + 50(j − 1) + k + 14550000 | Compound 14550001-14675000 |
| (structure) | Ar = Ai<br>R₁ = Rj<br>R₂ = Rk<br>R₃ = Rm<br>i, j, k and m are each independently an integer from 1 to 50 | 125000(i − 1) + 2500(j − 1) + 50(k − 1) + m + 14675000 | Compound 14675001-20925000 |
| (structure) | Ar = Ai<br>R₁ = Rj<br>R₂ = Rk<br>R₃ = Rm<br>i, j, k and m are each independently an integer from 1 to 50 | 125000(i − 1) + 2500(j − 1) + 50(k − 1) + m + 20925000 | Compound 20925001-27175000 |
| (structure) | Ar = Ai<br>R₁ = Rj<br>R₂ = Rk<br>i, j, and k are each independently an integer from 1 to 50 | 2500(i − 1) + 50(j − 1) + k + 27175000 | Compound 27175001-27300000 |

-continued

| Structure | R₁, R₂, Ar | x equal to | Compound x |
|---|---|---|---|
| (structure) | Ar = Ai<br>R₁ = Rj<br>R₂ = Rk<br>i, j, and k are each independently an integer from 1 to 50 | 2500(i − 1) + 50(j − 1) + k + 27300000 | Compound 27300001-27425000 |
| (structure) | Ar = Ai<br>R₁ = Rj<br>R₂ = Rk<br>i, j, and k are each independently an integer from 1 to 50 | 2500(i − 1) + 50(j − 1) + k + 27425000 | Compound 27425001-27550000 |
| (structure) | Ar = Ai<br>R₁ = Rj<br>R₂ = Rk<br>R₃ = Rm<br>i, j, k and m are each independently an integer from 1 to 50 | 125000(i − 1) + 2500(j − 1) + 50(k − 1) + m + 27550000 | Compound 27550001-33800000 |
| (structure) | Ar = Ai<br>R₁ = Rj<br>R₂ = Rk<br>R₃ = Rm<br>i, j, k and m are each independently an integer from 1 to 50 | 125000(i − 1) + 2500(j − 1) + 50(k − 1) + m + 33800000 | Compound 33800001-40050000 |
| (structure) | Ar = Ai<br>R₁ = Rj<br>R₂ = Rk<br>i, j, and k are each independently an integer from 1 to 50 | 2500(i − 1) + 50(j − 1) + k + 40050000 | Compound 40050001-40175000 |
| (structure) | Ar = Ai<br>R₁ = Rj<br>R₂ = Rk<br>i, j, and k are each independently an integer from 1 to 50 | 2500(i − 1) + 50(j − 1) + k + 40175000 | Compound 40175001-40300000 |

| Structure | $R_1$, $R_2$, Ar | x equal to | Compound x |
|---|---|---|---|
| (structure) | Ar = Ai<br>$R_1$ = Rj<br>$R_2$ = Rk<br>i, j, and k are each independently an integer from 1 to 50 | 2500(i − 1) + 50(j − 1) + k + 40300000 | Compound 40300001-40425000 |
| (structure) | Ar = Ai<br>$R_1$ = Rj<br>$R_2$ = Rk<br>$R_3$ = Rm<br>i, j, k and m are each independently an integer from 1 to 50 | 125000(i − 1) + 2500(j − 1) + 50(k − 1) + m + 40425000 | Compound 40425001-46675000 |
| (structure) | Ar = Ai<br>$R_1$ = Rj<br>$R_2$ = Rk<br>$R_3$ = Rm<br>i, j, k and m are each independently an integer from 1 to 50 | 125000(i − 1) + 2500(j − 1) + 50(k − 1) + m + 46675000 | Compound 46675001-52925000 |
| (structure) | Ar = Ai<br>$R_1$ = Rj<br>$R_2$ = Rk<br>$R_3$ = Rm<br>i, j, k and m are each independently an integer from 1 to 50 | 125000(i − 1) + 2500(j − 1) + 50(k − 1) + m + 52925000 | Compound 52925001-53050000 |
| (structure) | Ar = Ai<br>$R_1$ = Rj<br>$R_2$ = Rk<br>$R_3$ = Rm<br>i, j, k and m are each independently an integer from 1 to 50 | 125000(i − 1) + 2500(j − 1) + 50(k − 1) + m + 53050000 | Compound 53050001-53175000 |
| (structure) | Ar = Ai<br>$R_1$ = Rj<br>$R_2$ = Rk<br>$R_3$ = Rm<br>i, j, k and m are each independently an integer from 1 to 50 | 125000(i − 1) + 2500(j − 1) + 50(k − 1) + m + 53175000 | Compound 53175001-53300000 |

-continued

| Structure | R₁, R₂, Ar | x equal to | Compound x |
|---|---|---|---|
| (structure) | Ar = Ai<br>R₁ = Rj<br>R₂ = Rk<br>R₃ = Rm<br>i, j, k and m are each independently an integer from 1 to 50 | 125000(i − 1) + 2500(j − 1) + 50(k − 1) + m + 53300000 | Compound 53300001-59550000 |
| (structure) | Ar = Ai<br>R₁ = Rj<br>R₂ = Rk<br>R₃ = Rm<br>i, j, k and m are each independently an integer from 1 to 50 | 125000(i − 1) + 2500(j − 1) + 50(k − 1) + m + 59550000 | Compound 59550001-65800000 |
| (structure) | Ar = Ai<br>R₁ = Rj<br>R₂ = Rk<br>i, j, and k are each independently an integer from 1 to 50 | 2500(i − 1) + 50(j − 1) + k + 65800000 | Compound 65800001-65925000 |
| (structure) | Ar = Ai<br>R₁ = Rj<br>R₂ = Rk<br>i, j, and k are each independently an integer from 1 to 50 | 2500(i − 1) + 50(j − 1) + k + 65925000 | Compound 65925001-66050000 |
| (structure) | Ar = Ai<br>R₁ = Rj<br>R₂ = Rk<br>i, j, and k are each independently an integer from 1 to 50 | 2500(i − 1) + 50(j − 1) + k + 66050000 | Compound 66050001-66175000 |
| (structure) | Ar = Ai<br>R₁ = Rj<br>R₂ = Rk<br>R₃ = Rm<br>i, j, k and m are each independently an integer from 1 to 50 | 125000(i − 1) + 2500(j − 1) + 50(k − 1) + m + 66175000 | Compound 66175001-72425000 |

| Structure | $R_1$, $R_2$, Ar | x equal to | Compound x |
|---|---|---|---|
| (structure) | Ar = Ai<br>$R_1$ = Rj<br>$R_2$ = Rk<br>$R_3$ = Rm<br>i, j, k and m are each independently an integer from 1 to 50 | 125000(i − 1) + 2500(j − 1) + 50(k − 1) + m + 72425000 | Compound 72425001-78675000 |
| (structure) | Ar = Ai<br>$R_1$ = Rj<br>$R_2$ = Rk<br>i, j, and k are each independently an integer from 1 to 50 | 2500(i − 1) + 50(j − 1) + k + 78675000 | Compound 78675001-78800000 |
| (structure) | Ar = Ai<br>$R_1$ = Rj<br>$R_2$ = Rk<br>i, j, and k are each independently an integer from 1 to 50 | 2500(i − 1) + 50(j − 1) + k + 78800000 | Compound 78800001-78925000 |
| (structure) | Ar = Ai<br>$R_1$ = Rj<br>$R_2$ = Rk<br>i, j, and k are each independently an integer from 1 to 50 | 2500(i − 1) + 50(j − 1) + k + 78925000 | Compound 78925001-79050000 |
| (structure) | Ar = Ai<br>$R_1$ = Rj<br>$R_2$ = Rk<br>i, j, and k are each independently an integer from 1 to 50 | 2500(i − 1) + 50(j − 1) + k + 79050000 | Compound 79050001-79175000 |
| (structure) | Ar = Ai<br>$R_1$ = Rj<br>$R_2$ = Rk<br>$R_3$ = Rm<br>i, j, k and m are each independently an integer from 1 to 50 | 125000(i − 1) + 2500(j − 1) + 50(k − 1) + m + 79175000 | Compound 79175001-85425000 |

-continued

| Structure | $R_1$, $R_2$, Ar | x equal to | Compound x |
|---|---|---|---|
| (structure) | Ar = Ai<br>$R_1$ = Rj<br>$R_2$ = Rk<br>$R_3$ = Rm<br>i, j, k and m are each independently an integer from 1 to 50 | 125000(i − 1) + 2500(j − 1) + 50(k − 1) + m + 85425000 | Compound 85425001-91675000 |
| (structure) | Ar = Ai<br>$R_1$ = Rj<br>$R_2$ = Rk<br>$R_3$ = Rm<br>i, j, k and m are each independently an integer from 1 to 50 | 125000(i − 1) + 2500(j − 1) + 50(k − 1) + m + 91675000 | Compound 91675001-97925000 |
| (structure) | Ar = Ai<br>$R_1$ = Rj<br>$R_2$ = Rk<br>$R_3$ = Rm<br>i, j, k and m are each independently an integer from 1 to 50 | 125000(i − 1) + 2500(j − 1) + 50(k − 1) + m + 97925000 | Compound 97925001-104175000 |
| (structure) | Ar = Ai<br>$R_1$ = Rj<br>$R_2$ = Rk<br>i, j, and k are each independently an integer from 1 to 50 | 2500(i − 1) + 50(j − 1) + k + 104175000 | Compound 104175001-104300000 |
| (structure) | Ar = Ai<br>$R_1$ = Rj<br>$R_2$ = Rk<br>i, j, and k are each independently an integer from 1 to 50 | 2500(i − 1) + 50(j − 1) + k + 104300000 | Compound 104300001-104425000 |
| (structure) | Ar = Ai<br>$R_1$ = Rj<br>$R_2$ = Rk<br>i, j, and k are each independently an integer from 1 to 50 | 2500(i − 1) + 50(j − 1) + k + 104425000 | Compound 104425001-104550000 |

-continued

| Structure | R₁, R₂, Ar | x equal to | Compound x |
|---|---|---|---|
| (structure) | Ar = Ai<br>R₁ = Rj<br>R₂ = Rk<br>i, j, and k are each independently an integer from 1 to 50 | 2500(i − 1) + 50(j − 1) + k + 104550000 | Compound 104550001-104675000 |
| (structure) | Ar = Ai<br>R₁ = Rj<br>R₂ = Rk<br>R₃ = Rm<br>i, j, k and m are each independently an integer from 1 to 50 | 125000(i − 1) + 2500(j − 1) + 50(k − 1) + m + 104675000 | Compound 104675001-110925000 |
| (structure) | Ar = Ai<br>R₁ = Rj<br>R₂ = Rk<br>R₃ = Rm<br>i, j, k and m are each independently an integer from 1 to 50 | 125000(i − 1) + 2500(j − 1) + 50(k − 1) + m + 110925000 | Compound 110925001-117175000 |
| (structure) | Ar = Ai<br>R₁ = Rj<br>R₂ = Rk<br>R₃ = Rm<br>i, j, k and m are each independently an integer from 1 to 50 | 125000(i − 1) + 2500(j − 1) + 50(k − 1) + m + 117175000 | Compound 117175001-123425000 |
| (structure) | Ar = Ai<br>R₁ = Rj<br>R₂ = Rk<br>R₃ = Rm<br>i, j, k and m are each independently an integer from 1 to 50 | 125000(i − 1) + 2500(j − 1) + 50(k − 1) + m + 123425000 | Compound 123425001-129675000 |

-continued

| Structure | R₁, R₂, Ar | x equal to | Compound x |
|---|---|---|---|
| | Ar = Ai<br>R₁ = Rj<br>R₂ = Rk<br>i, j, and k are each independently an integer from 1 to 50 | 2500(i − 1) + 50(j − 1) + k + 129675000 | Compound 129675001-129800000 |
| | Ar = Ai<br>R₁ = Rj<br>R₂ = Rk<br>i, j, and k are each independently an integer from 1 to 50 | 2500(i − 1) + 50(j − 1) + k + 129800000 | Compound 129800001-129925000 |
| | Ar = Ai<br>R₁ = Rj<br>R₂ = Rk<br>i, j, and k are each independently an integer from 1 to 50 | 2500(i − 1) + 50(j − 1) + k + 129925000 | Compound 129925001-130050000 |
| | Ar = Ai<br>R₁ = Rj<br>R₂ = Rk<br>i, j, and k are each independently an integer from 1 to 50 | 2500(i − 1) + 50(j − 1) + k + 130050000 | Compound 130050001-130175000 | wherein A1 to A50 have the following structures:
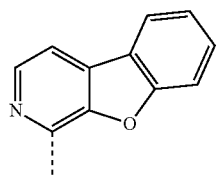
A1
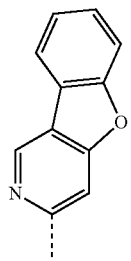
A2
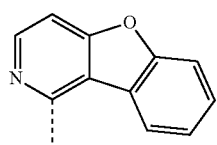
A3
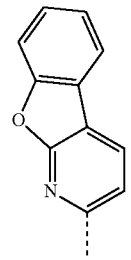
A4
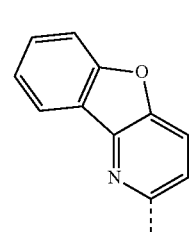
A5
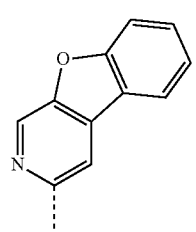
A6
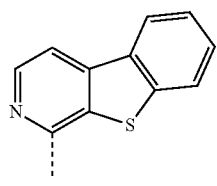
A7
-continued
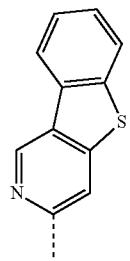
A8
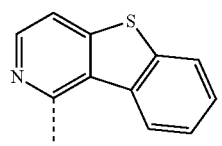
A9
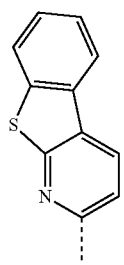
A10
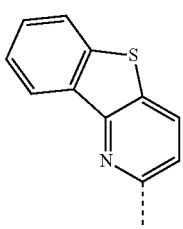
A11
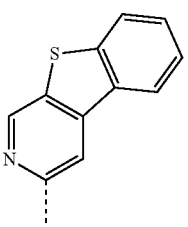
A12
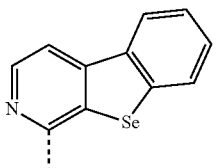
A13
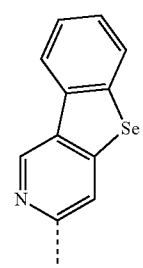
A14

A15 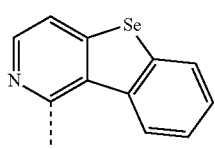
A16 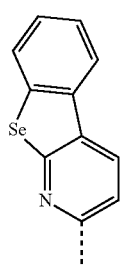
A17 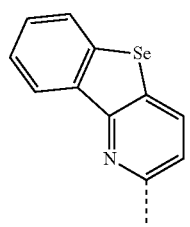
A18 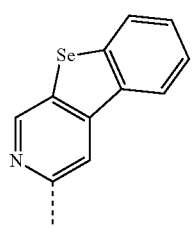
A19 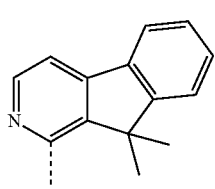
A20 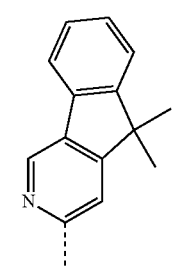
A21 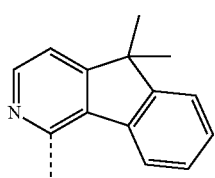
A22 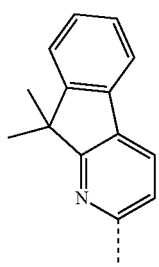
A23 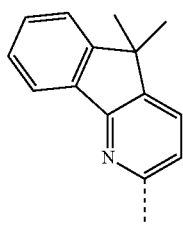
A24 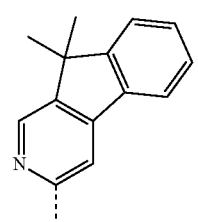
A25 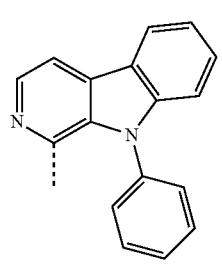
A26 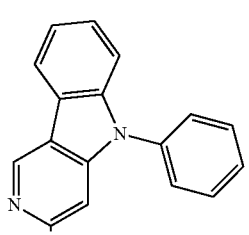
A27 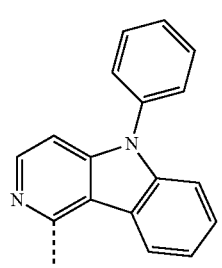

-continued
A28
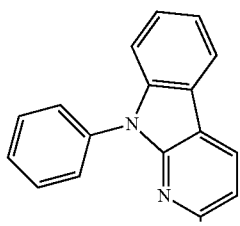
A29
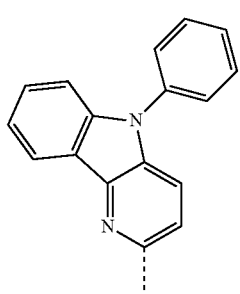
A30
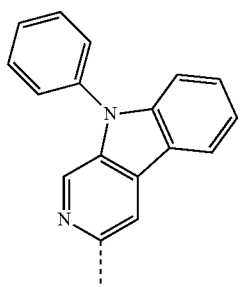
A31
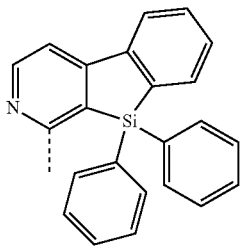
A32
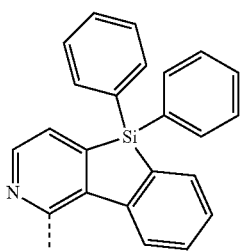
A33
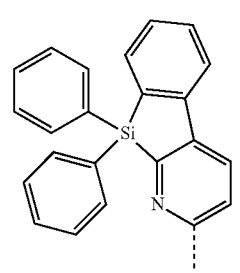
-continued
A34
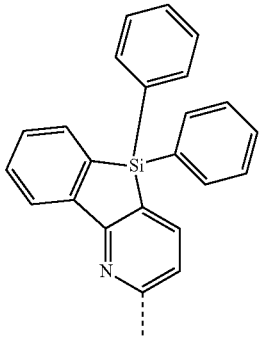
A35
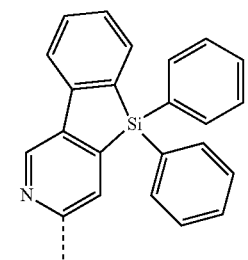
A36
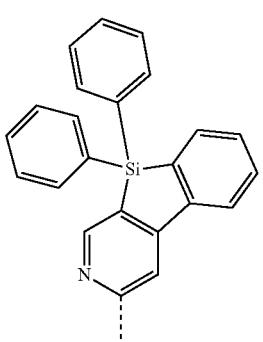
A37
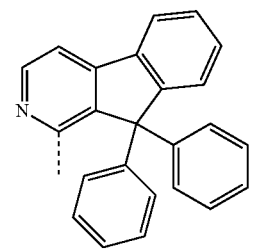
A38
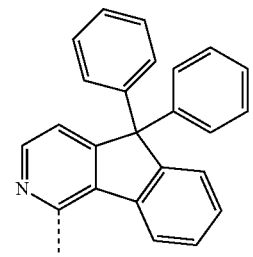

-continued
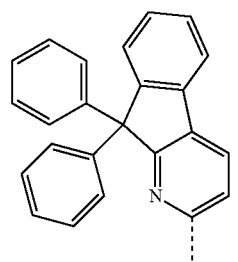
A39
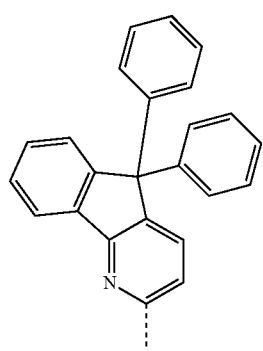
A40
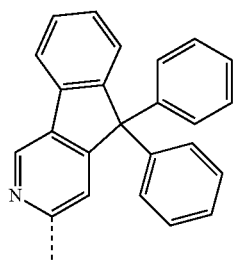
A41
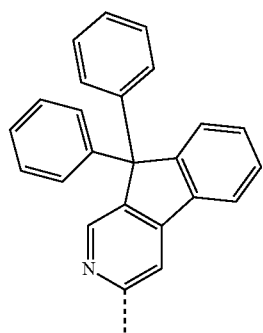
A42
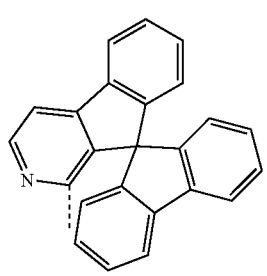
A43
-continued
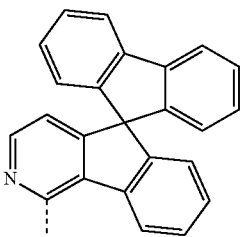
A44
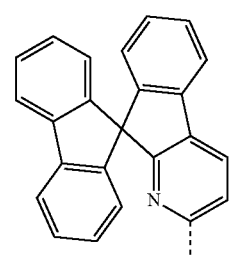
A45
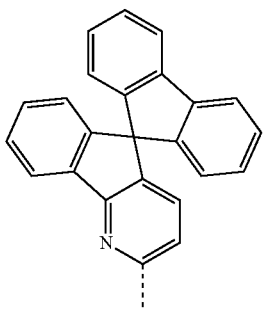
A46
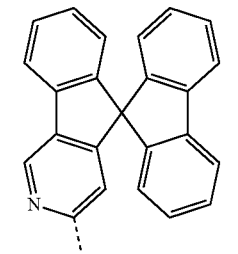
A47
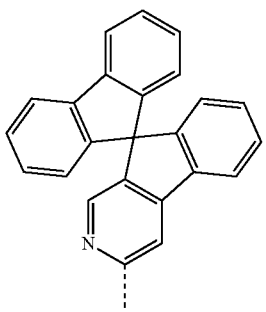
A48
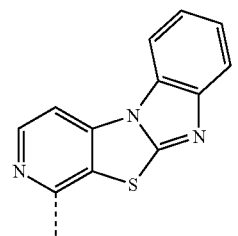
A49

A50
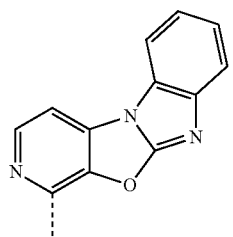
and wherein R1 to R50 have the following structures:
R: CH₃  R1
CD₃    R2
 R3
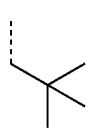 R4
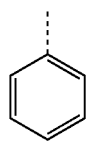 R5
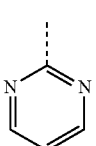 R6
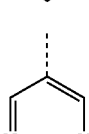 R7
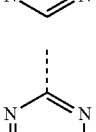 R8
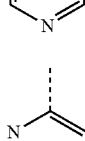 R9
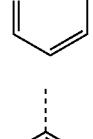 R10
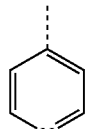 R11
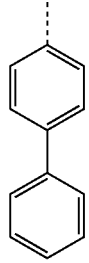 R12
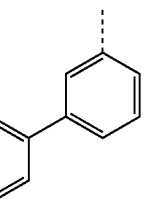 R13
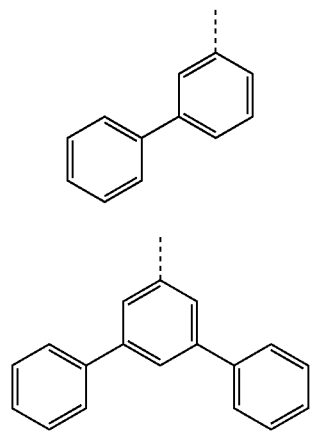 R14
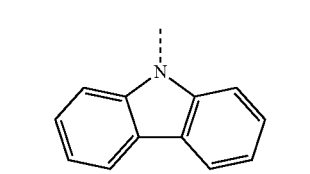 R15
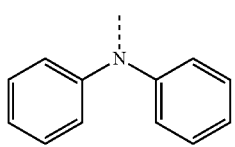 R16
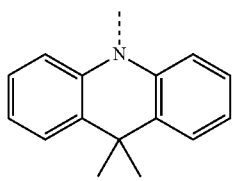 R17
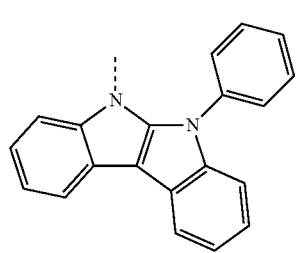 R18

R19 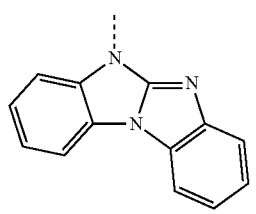
R20 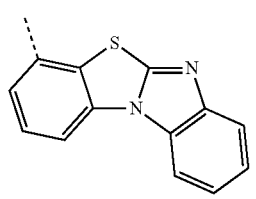
R21 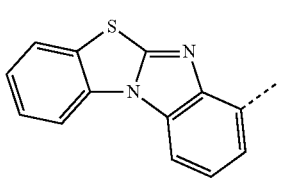
R22 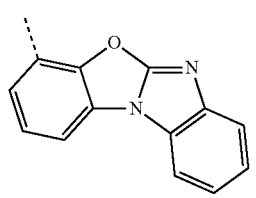
R23 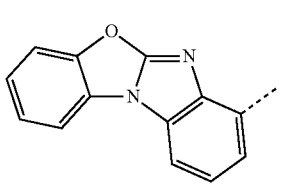
R24 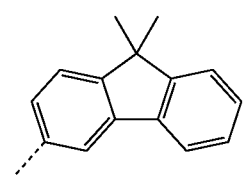
R25 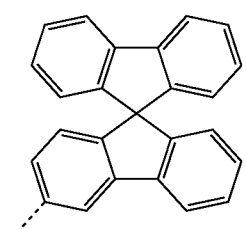
R26 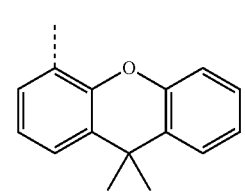
R27 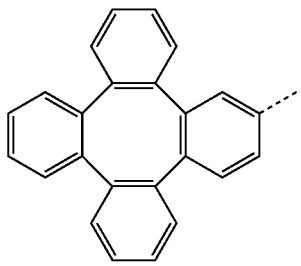
R28 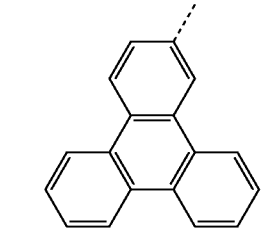
R29 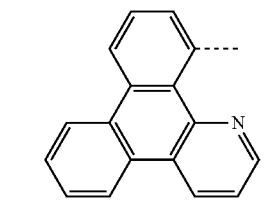
R30 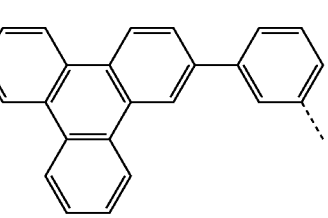
R31 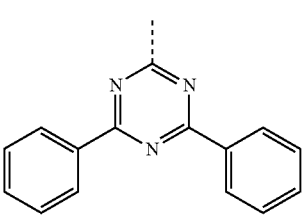
R32 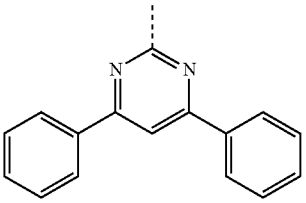
R33 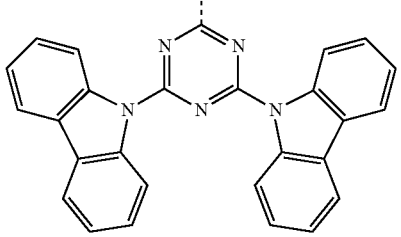

R34 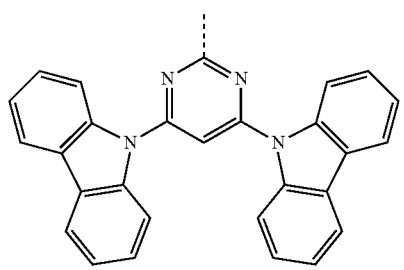
R35 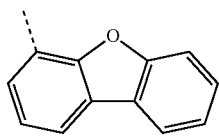
R36 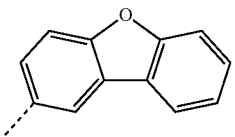
R37 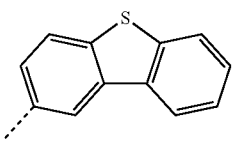
R38 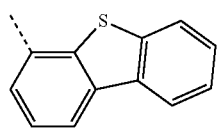
R39 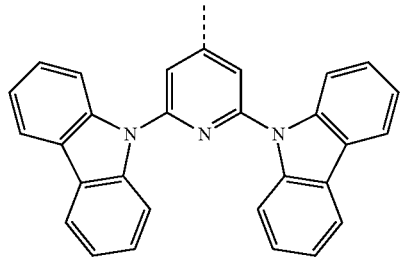
R40 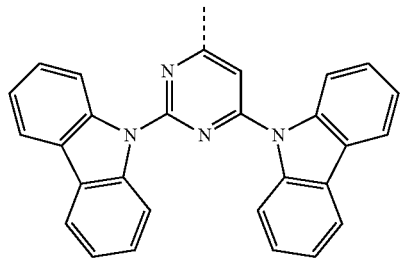
R41 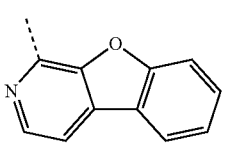
R42 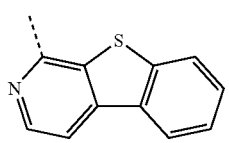
R43 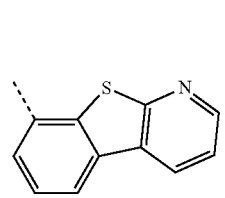
R44 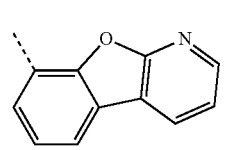
R45 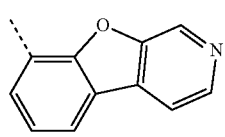
R46 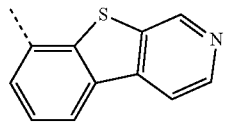
R47 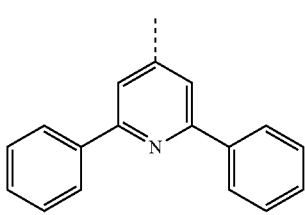
R48 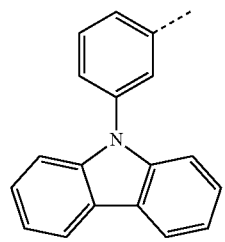
R49 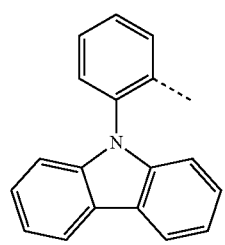

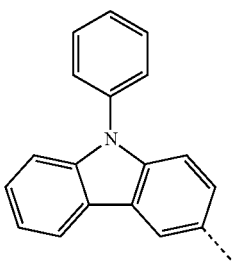
Preferred Ar groups include A1, A3, A7, A9, and A25.
Preferred R groups include R5, R14, R15, R19, R31, R32, R33, R34, R39, R40 R42, and R49.
In one embodiment, the compound is selected from the group consisting of:
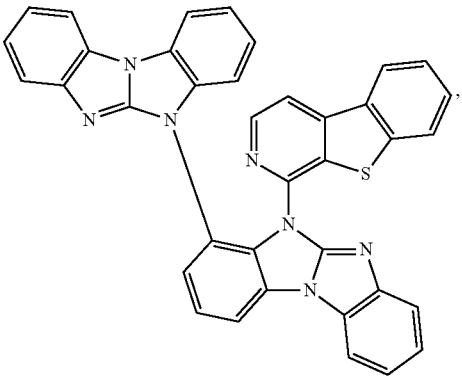
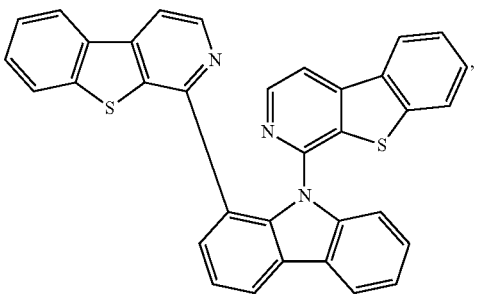
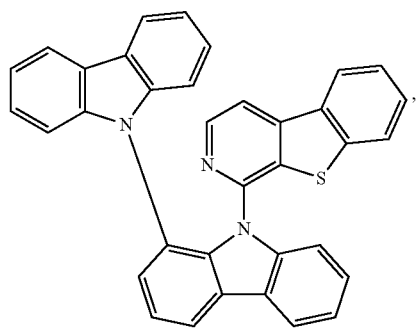
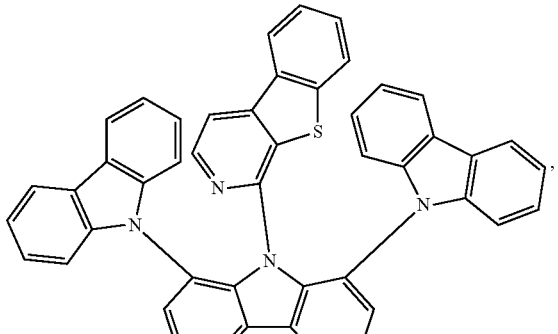
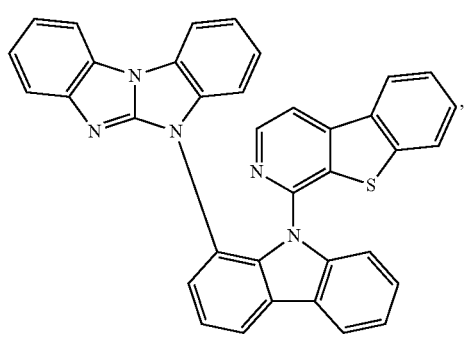
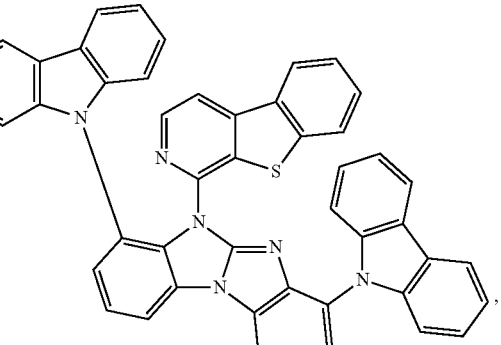
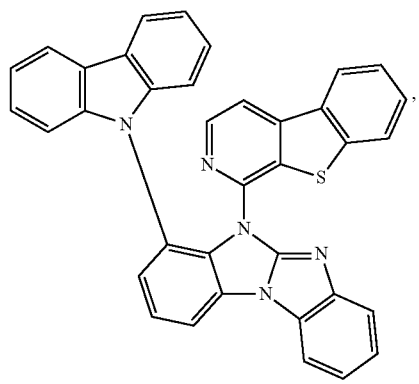
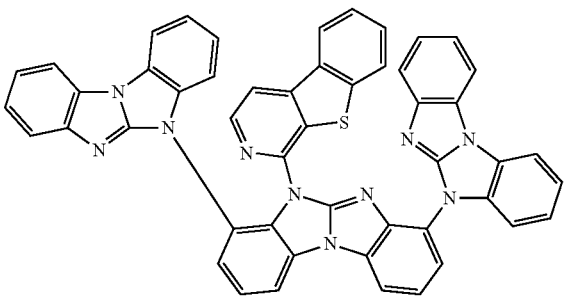

-continued
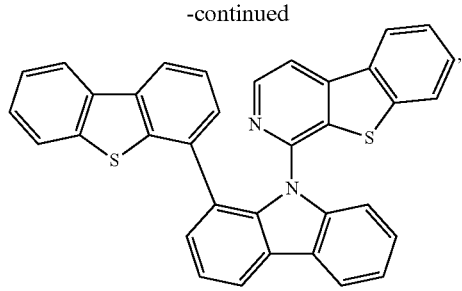
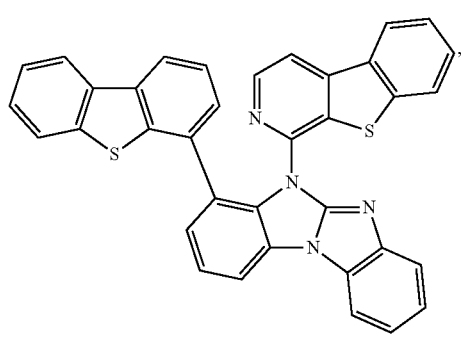
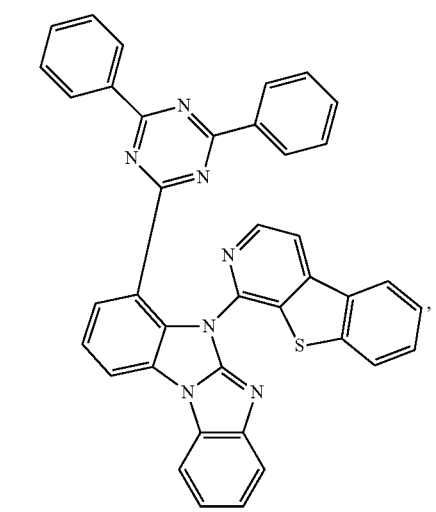
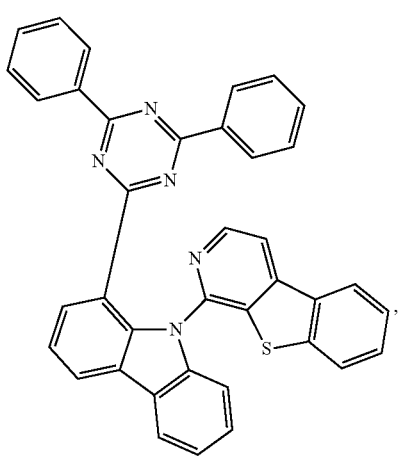
-continued
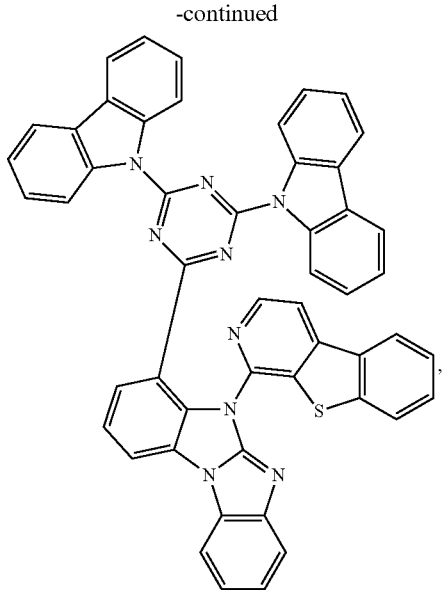
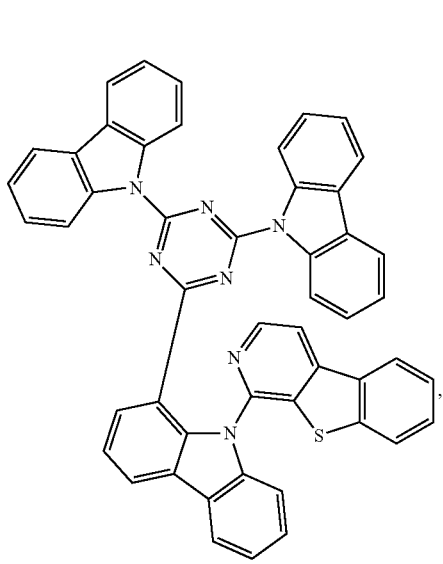
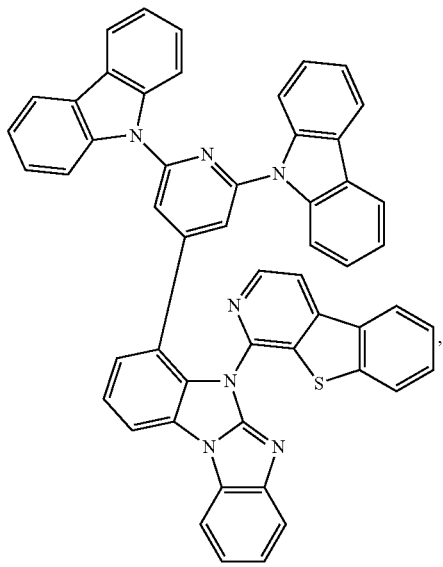

63
-continued
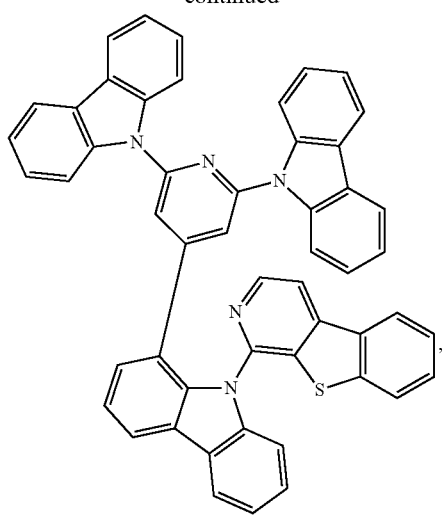
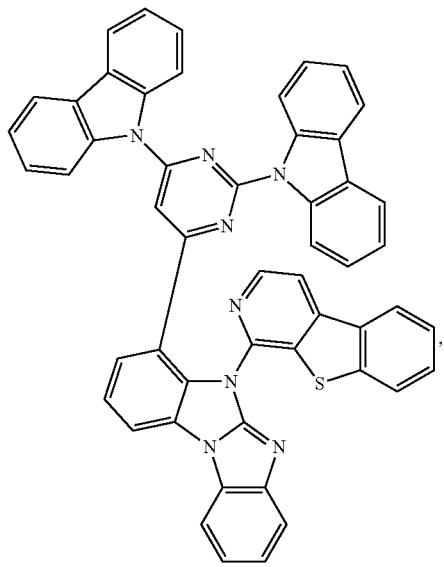
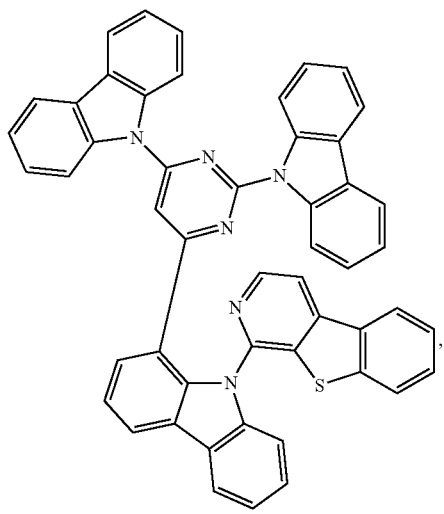
64
-continued
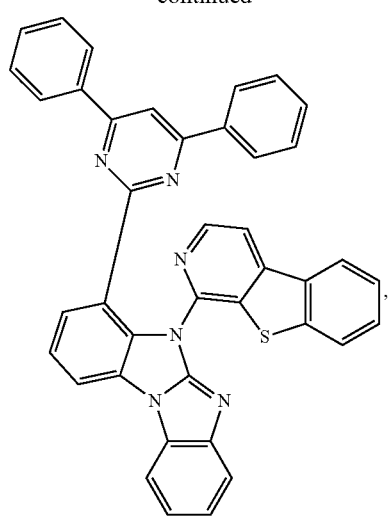
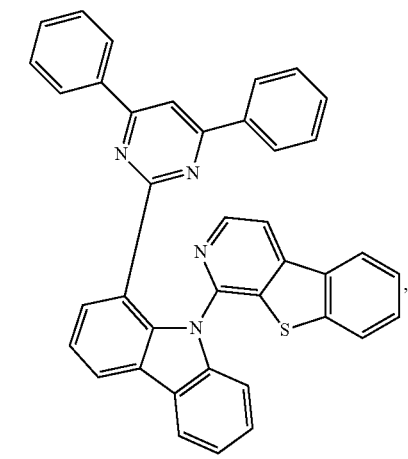
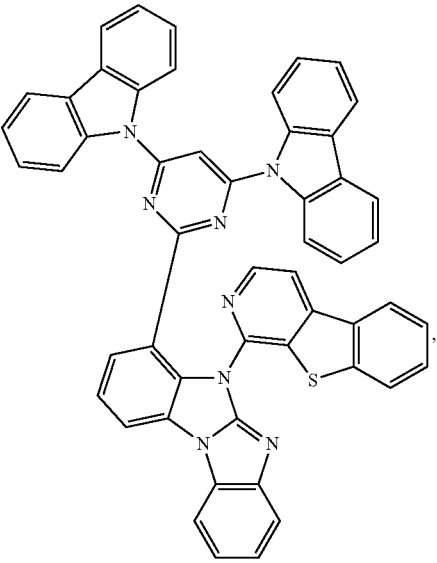

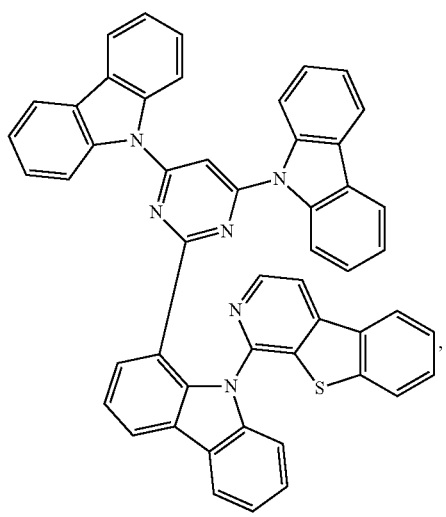
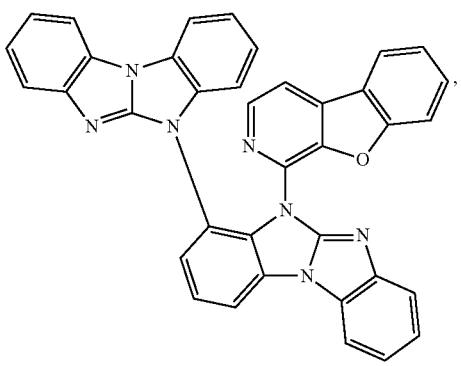
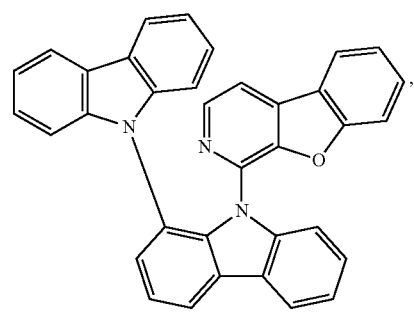
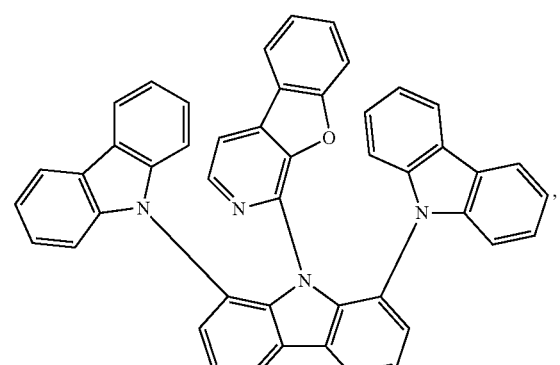
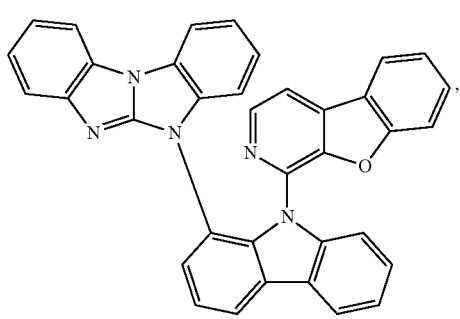
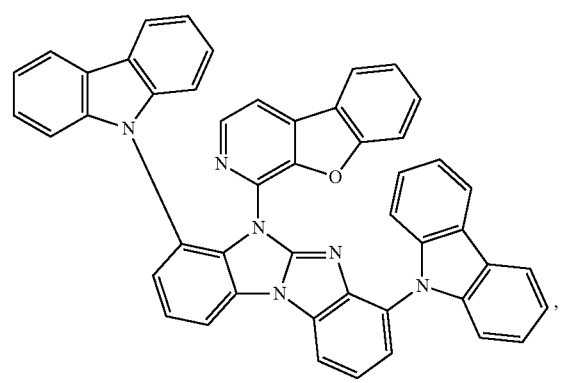
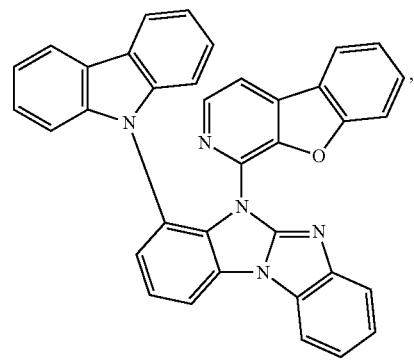
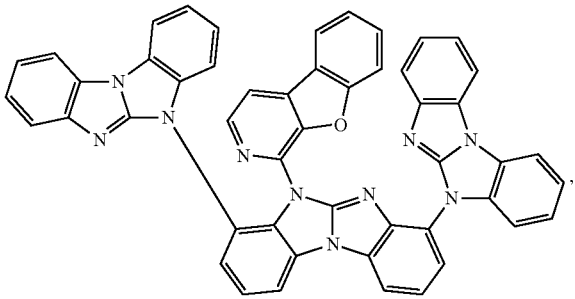

67
-continued
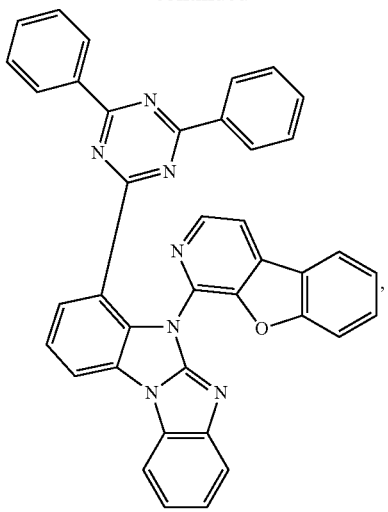
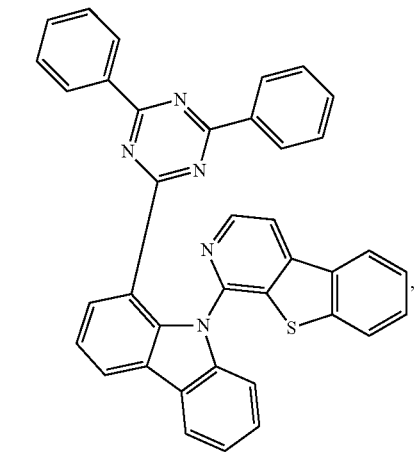
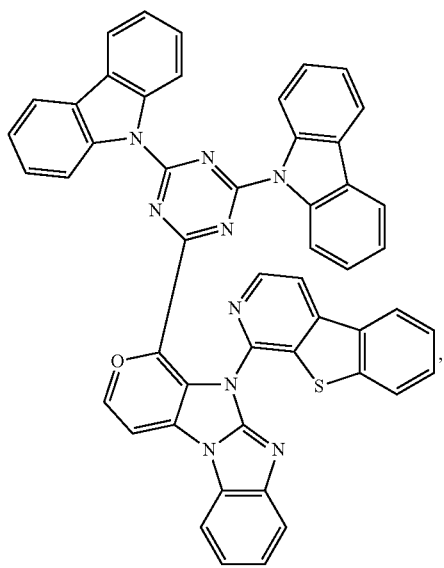
68
-continued
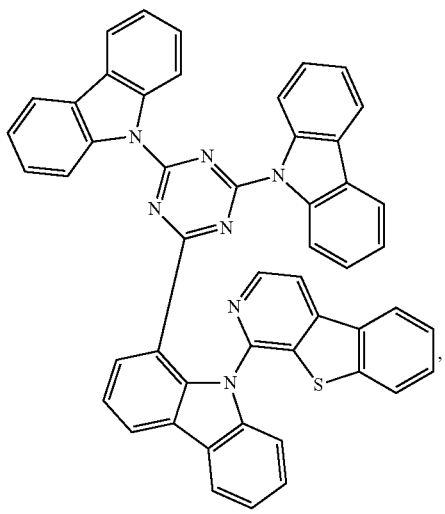
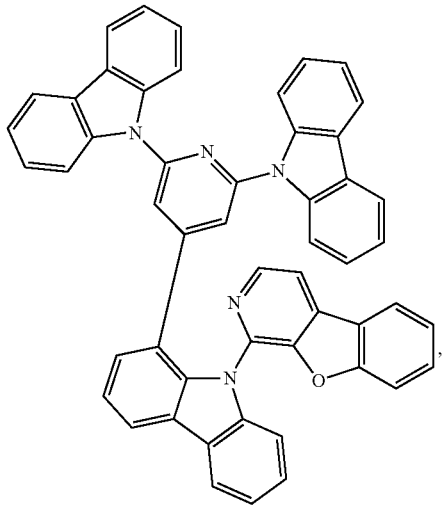
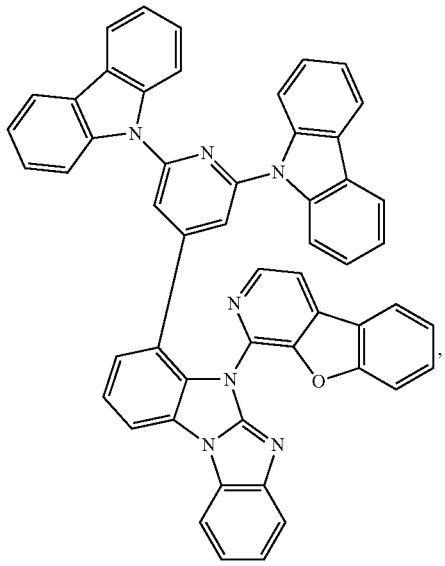

69
-continued
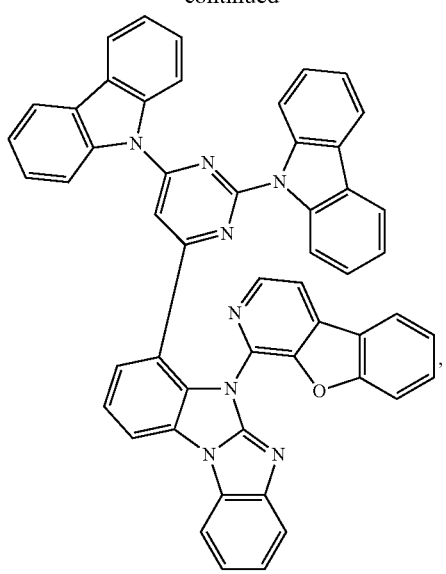
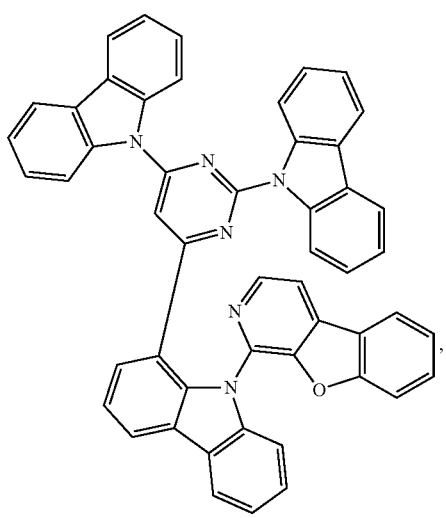
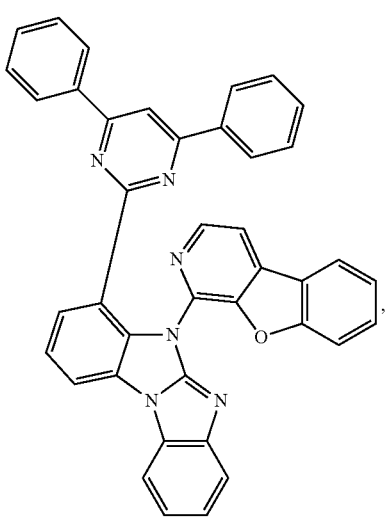
70
-continued
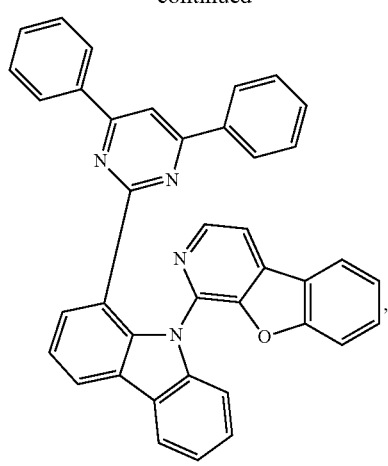
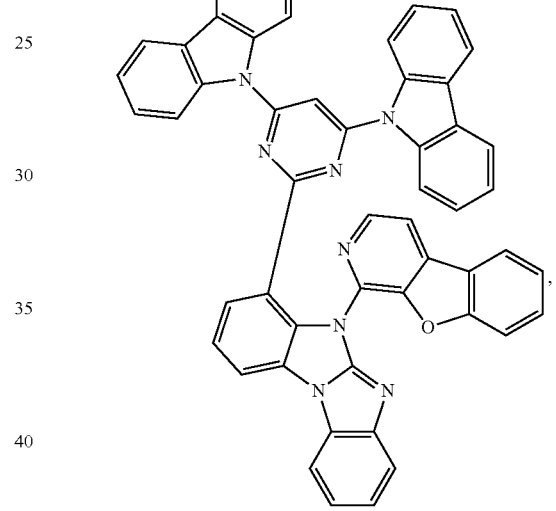
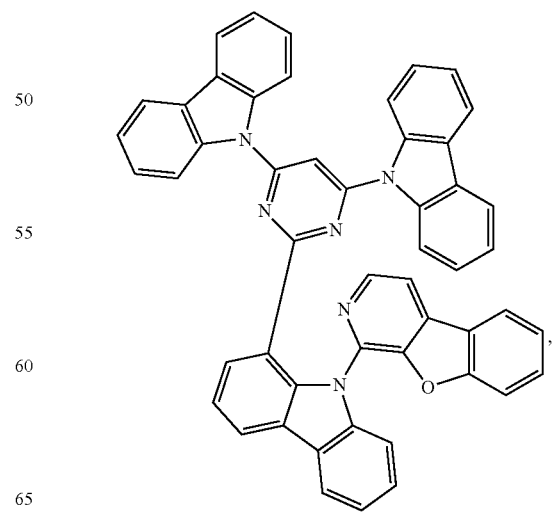

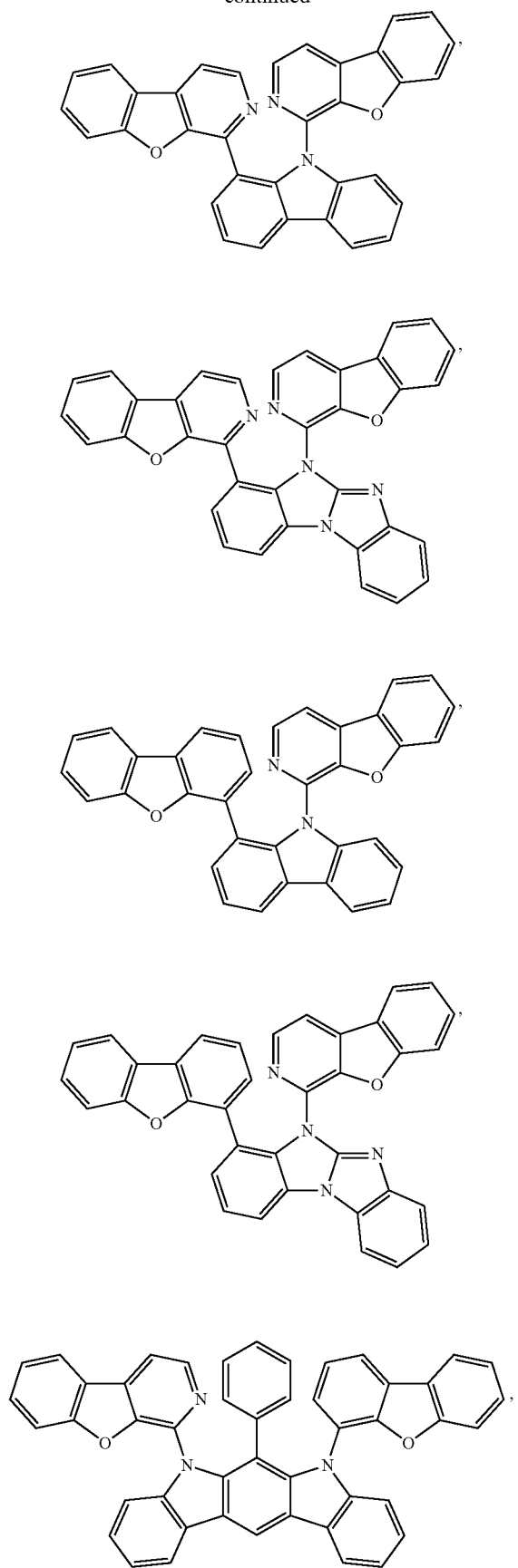
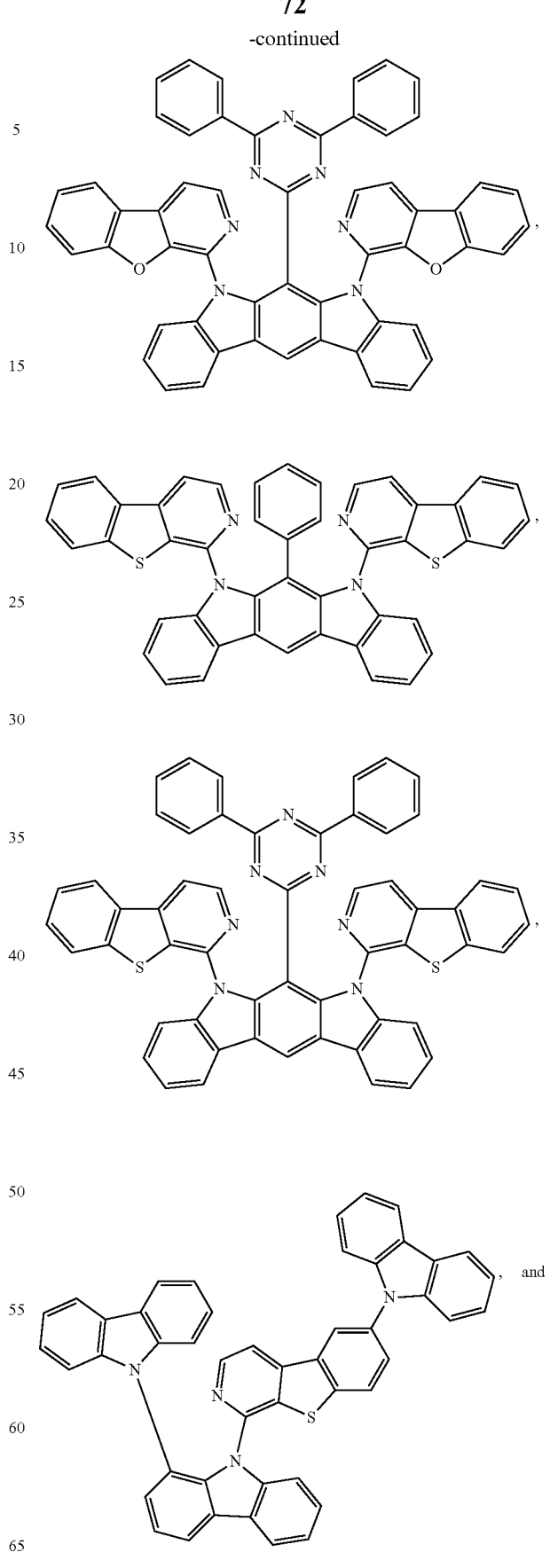

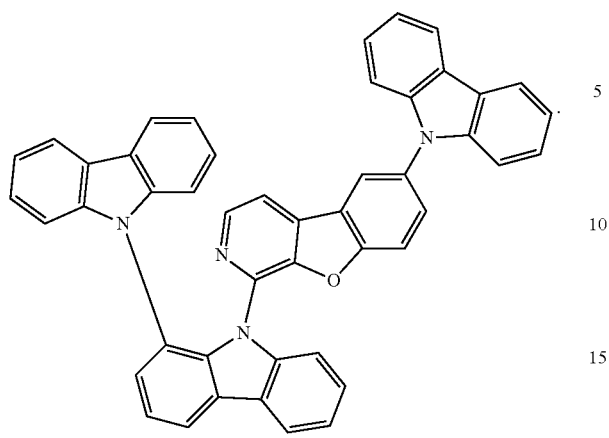

In another aspect, the present invention includes an organic light emitting device (OLED) comprising an anode, a cathode, and an organic layer disposed between the anode and the cathode, the organic layer comprising a compound according to Formula I.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

The emitter dopants can be phosphorescent dopants. The organic layer can include a compound according to Formula I, and its variations as described herein as a host.

In one embodiment, the organic layer further comprises a phosphorescent emissive dopant; wherein the emissive dopant is a transition metal complex having at least one ligand or part of the ligand if the ligand is more than bidentate selected from the group consisting of:

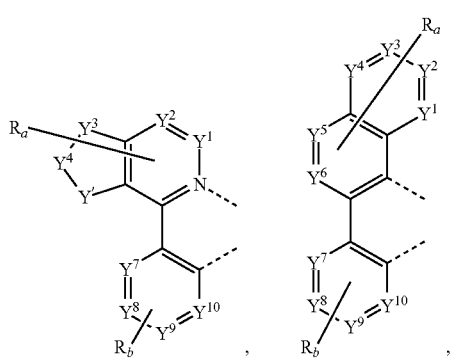

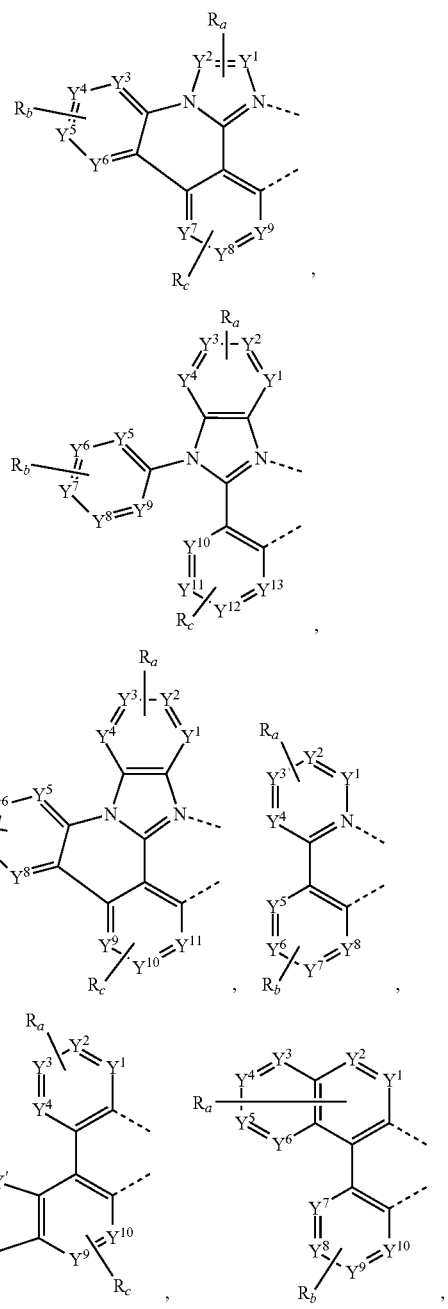

-continued

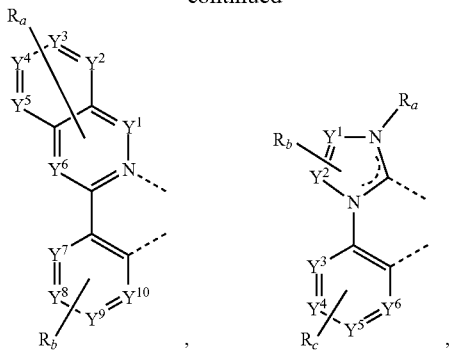

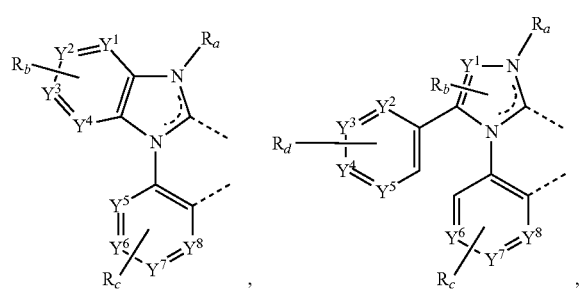

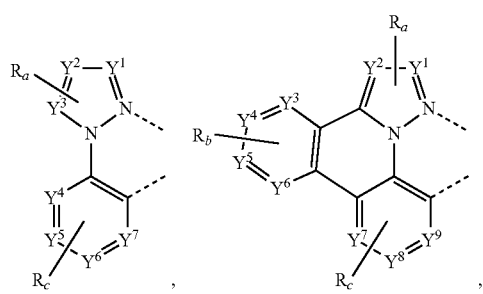

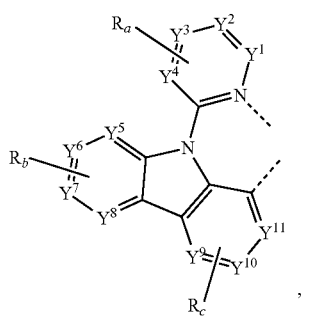

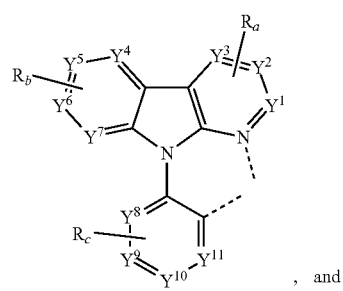

, and

-continued

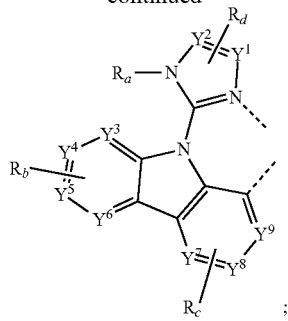

;

wherein
each $Y^1$ to $Y^{13}$ is independently selected from C or N;
Y' is selected from the group consisting of $BR_e$, $NR_e$, $PR_e$, O, S, Se, C=O, S=O, $SO_2$, $CR_eR_f$, $SiR_eR_f$, and $GeR_eR_f$;
$R_a$, $R_b$, $R_c$, and $R_d$ independently represent from mono substitution to the maximum possible number of substitution, or no substitution; each $R_a$, $R_b$, $R_c$, $R_d$, $R_e$ and $R_f$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and any two adjacent substituents $R_a$, $R_b$, $R_c$, and $R_d$ may optionally be joined to form a ring or form a multidentate ligand; and $R_e$ and $R_f$ may optionally be joined to form a ring.

In one embodiment, the organic layer is an emissive layer and includes a compound according to Formula I, the compound being a host compound.

In one embodiment, the organic layer is a blocking layer and the compound according to Formula I is a blocking material in the organic layer.

In one embodiment, the organic layer is a transporting layer and the compound according to Formula I is a transporting material in the organic layer.

In another aspect, the present invention includes a consumer product comprising an organic light-emitting device (OLED) comprising an anode, a cathode, and an organic layer disposed between the anode and the cathode, the organic layer comprising a compound according to Formula I.

According to another aspect, a formulation comprising the compound described herein is also disclosed.

The OLED disclosed herein can be incorporated into one or more of a consumer product, an electronic component module, and a lighting panel.

In yet another aspect of the present disclosure, a formulation that comprises the novel compound disclosed herein is described. The formulation can include one or more components selected from the group consisting of a solvent, a host, a hole injection material, hole transport material, electron blocking material, hole blocking material, and an electron transport layer material, disclosed herein.

The present disclosure encompasses any chemical structure comprising the novel compound of the present disclosure, or a monovalent or polyvalent variant thereof. In other words, the inventive compound, or a monovalent or polyvalent variant thereof, can be a part of a larger chemical structure. Such chemical structure can be selected from the group consisting of a monomer, a polymer, a macromolecule, and a supramolecule (also known as supermolecule). As used herein, a "monovalent variant of a compound" refers to a moiety that is identical to the compound except that one hydrogen has been removed and replaced with a bond to the rest of the chemical structure. As used herein, a "polyvalent variant of a compound" refers to a moiety that is identical to the compound except that more than one hydrogen has been removed and replaced with a bond or bonds to the rest of the chemical structure. In the instance of a supramolecule, the inventive compound can also be incorporated into the supramolecule complex without covalent bonds.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

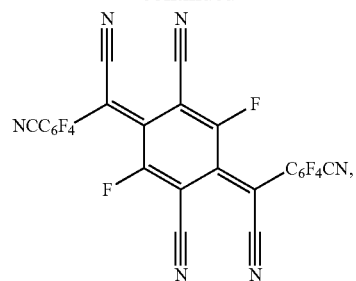

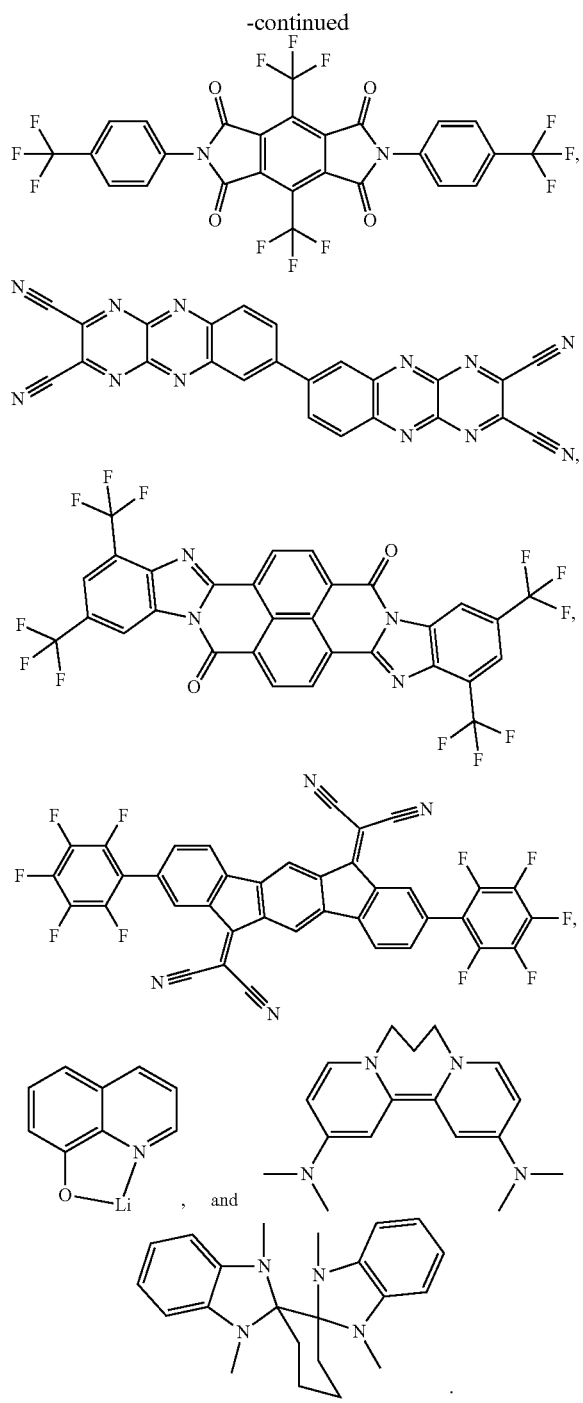

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5, 8,9,12-Hexaazatriphenylenehexacarbonitrile; a metal complex, and a cross-linkable compounds.

Examples of aromatic amine derivatives used in HIL or HTL include, but are not limited to the following general structures:

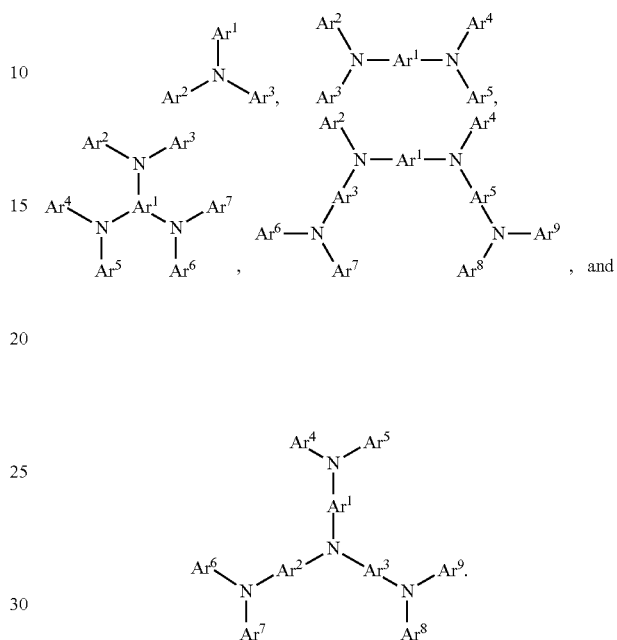

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, Ar¹ to Ar⁹ is independently selected from the group consisting of:

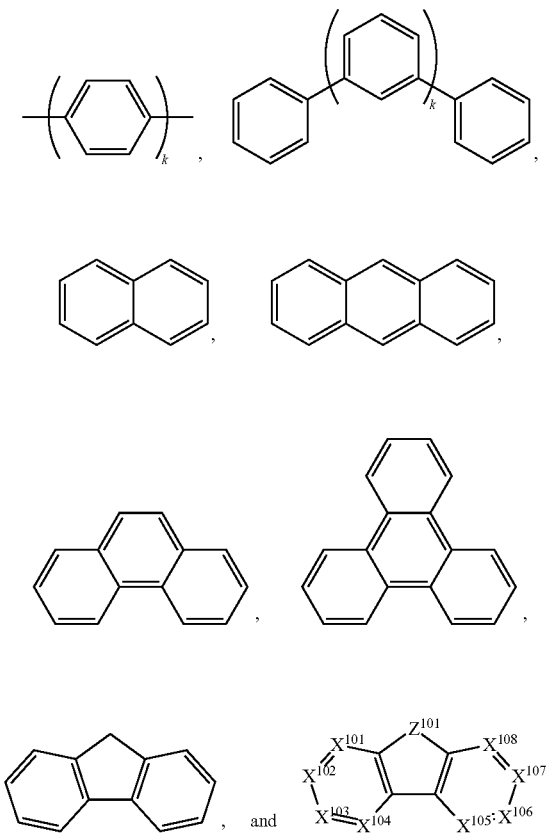

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

$$\left[ \left( \begin{matrix} Y^{101} \\ Y^{102} \end{matrix} \right)_{k'} Met - (L^{101})_{k''} \right]$$

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. Fc⁺/Fc couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO007125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018,

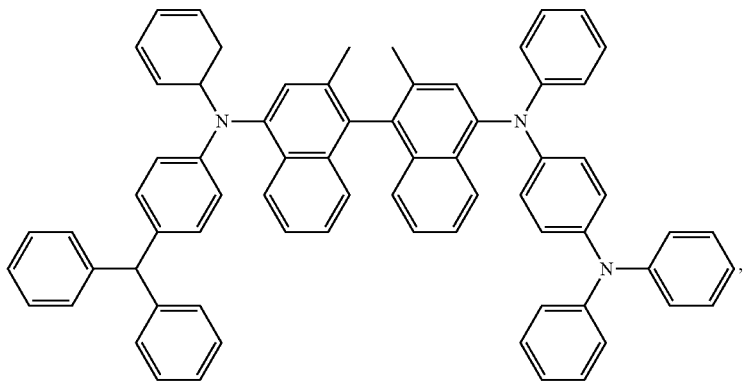

-continued
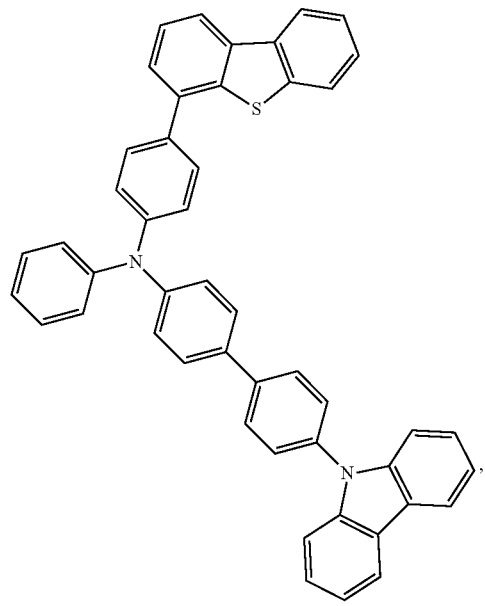
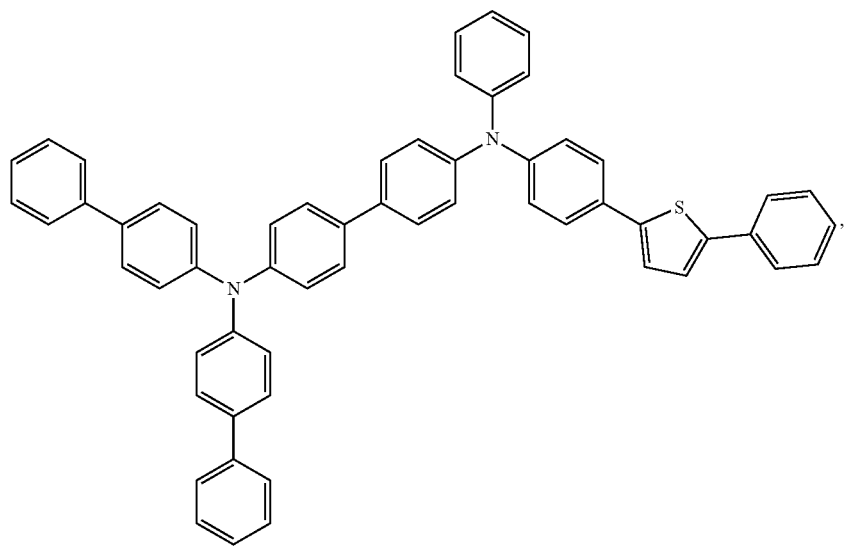
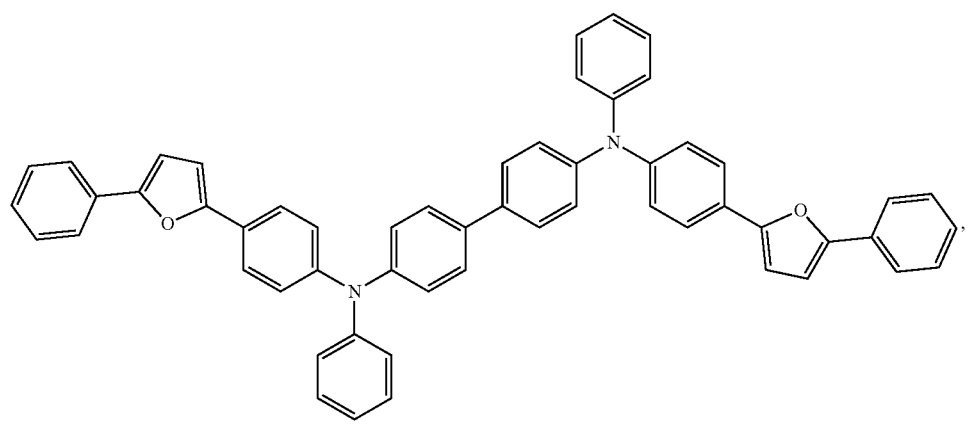

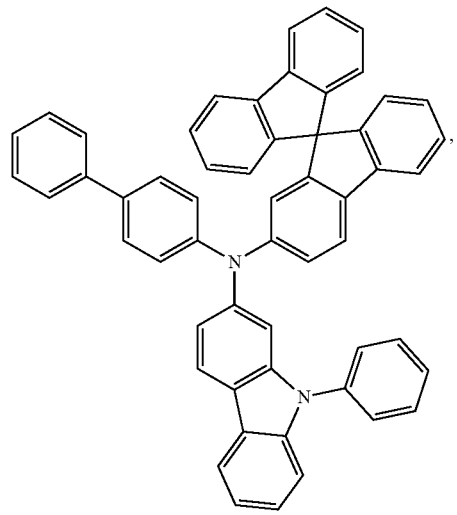
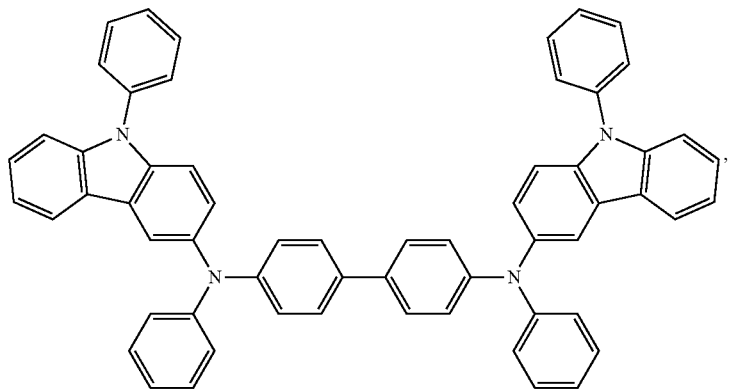
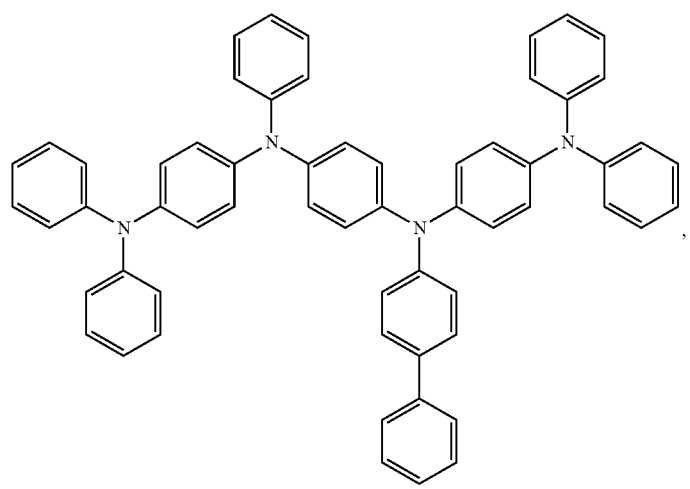
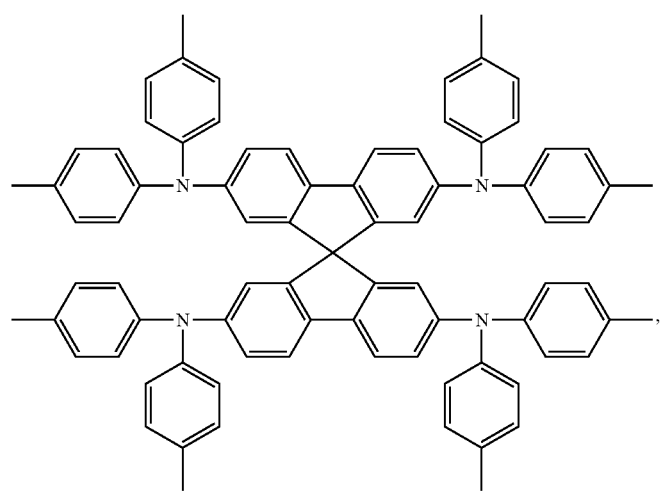

-continued
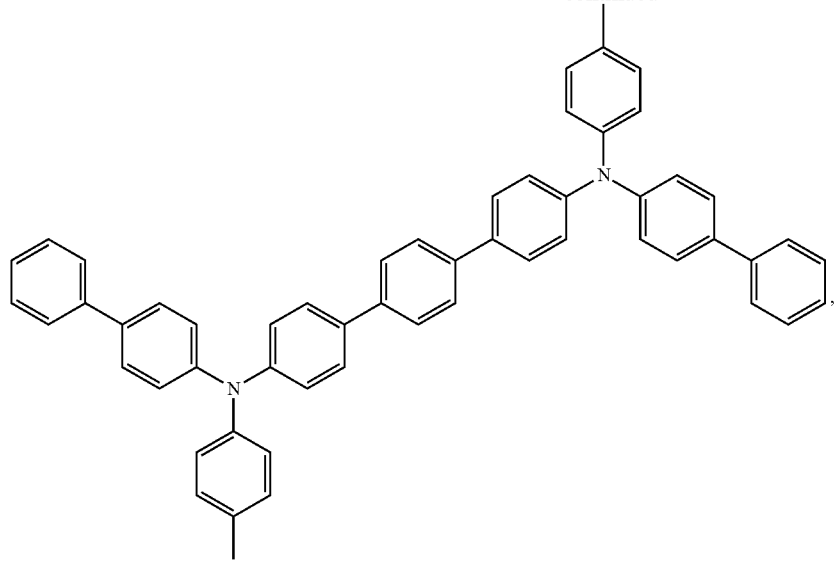
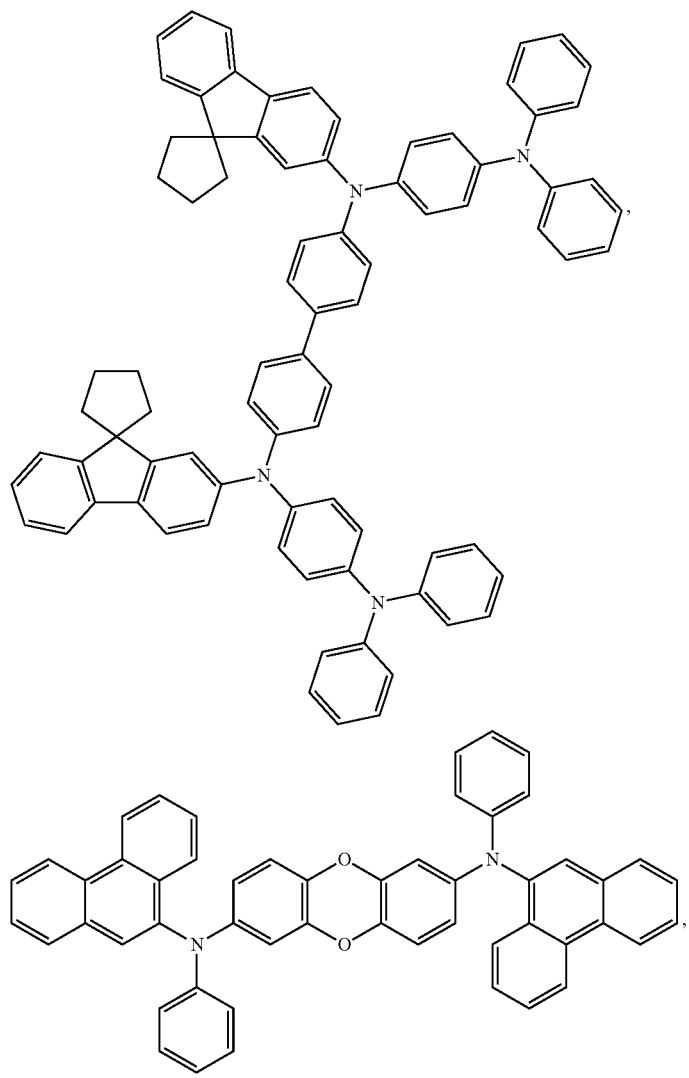

89
90
-continued
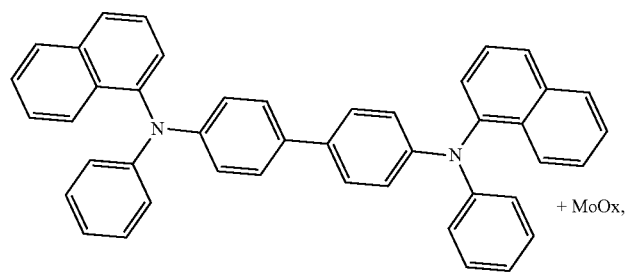
+ MoOx,
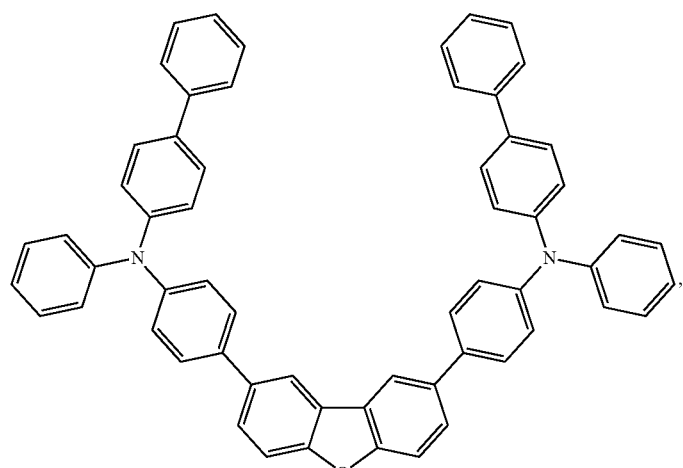
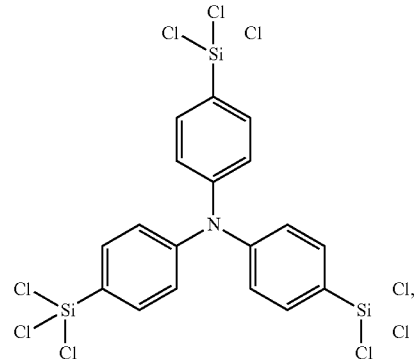
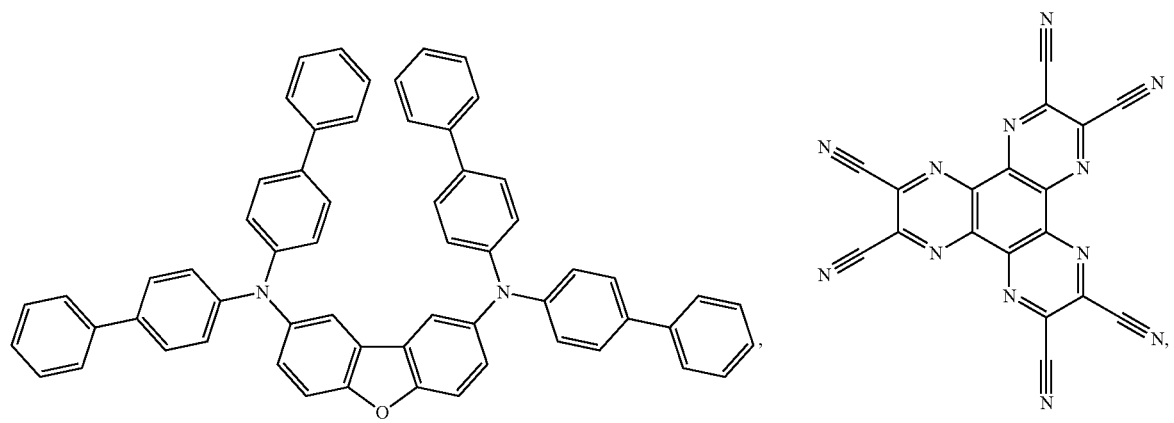
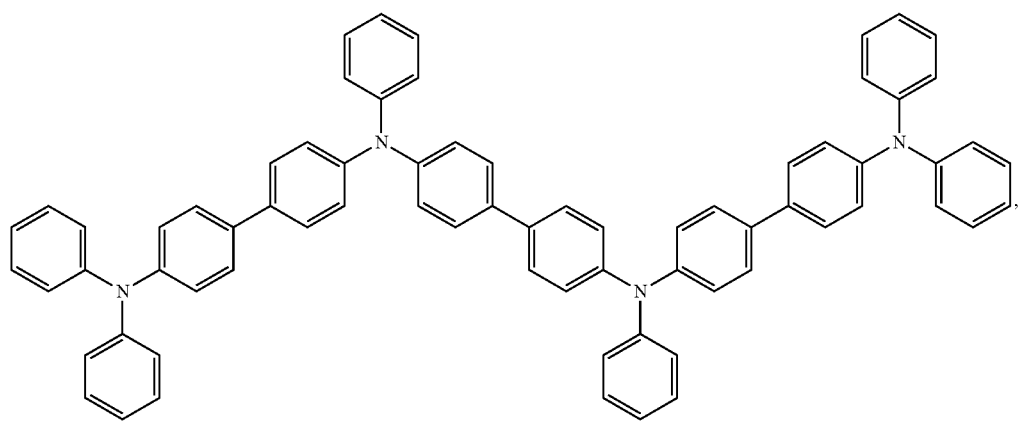

91
-continued
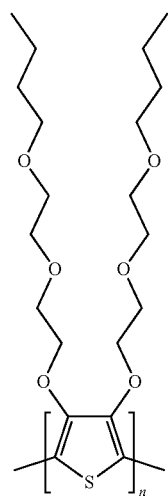 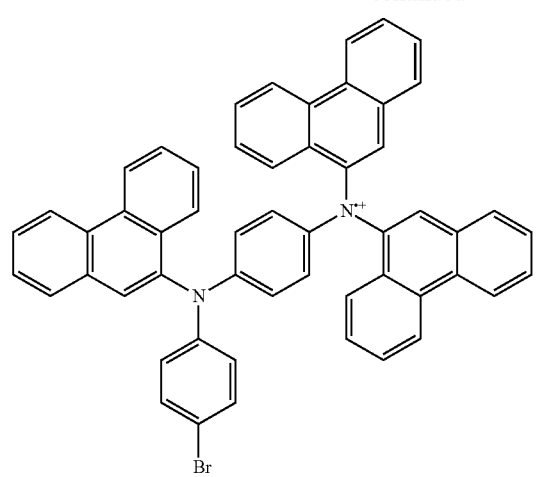 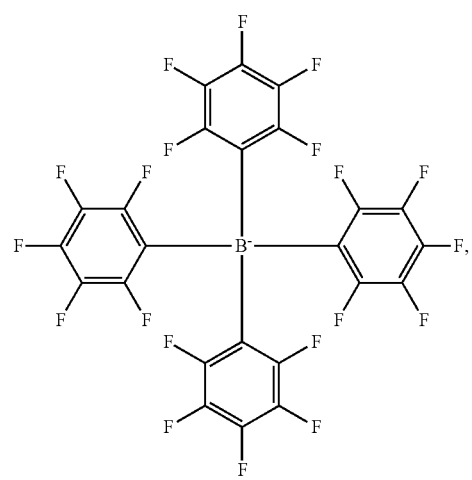
92
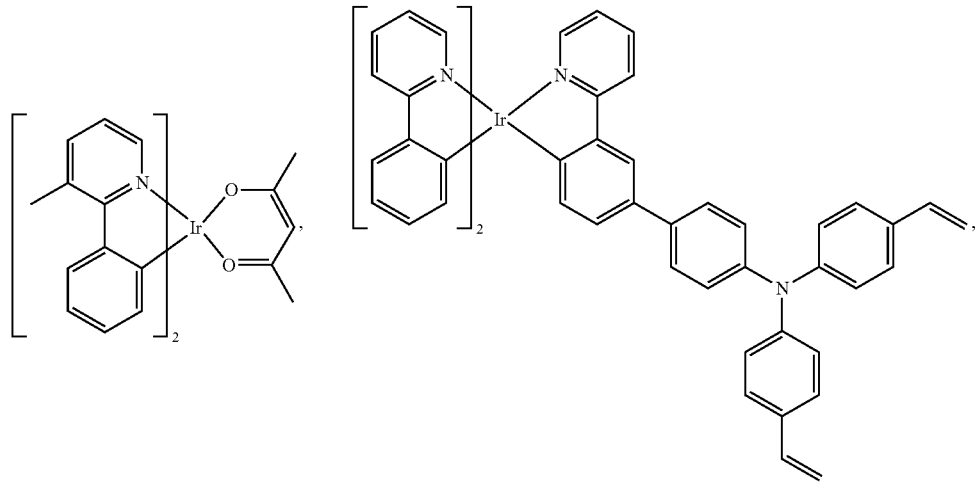
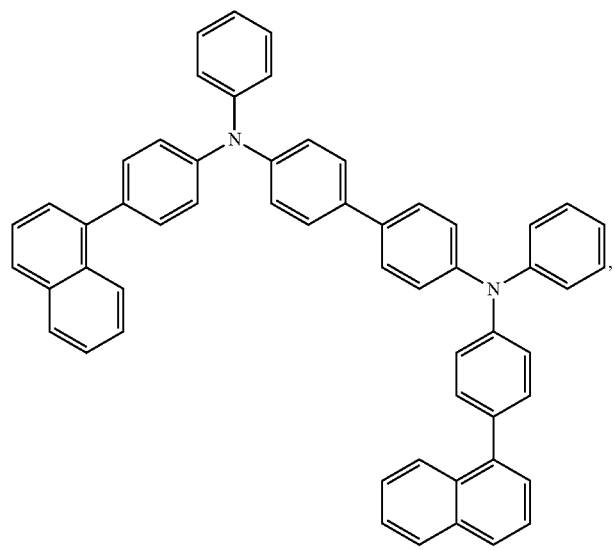

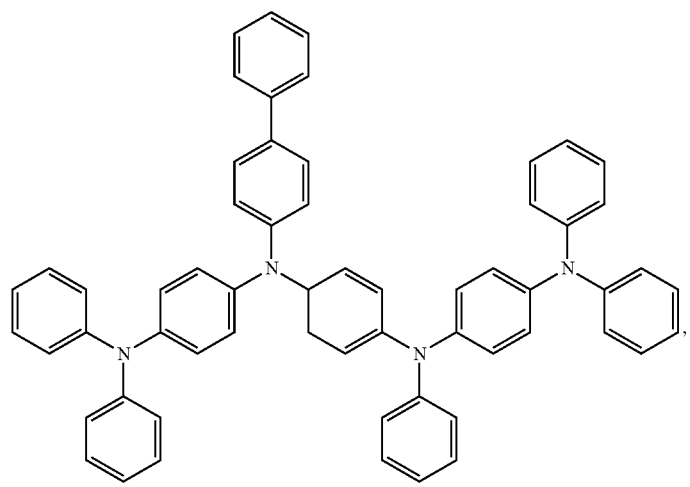
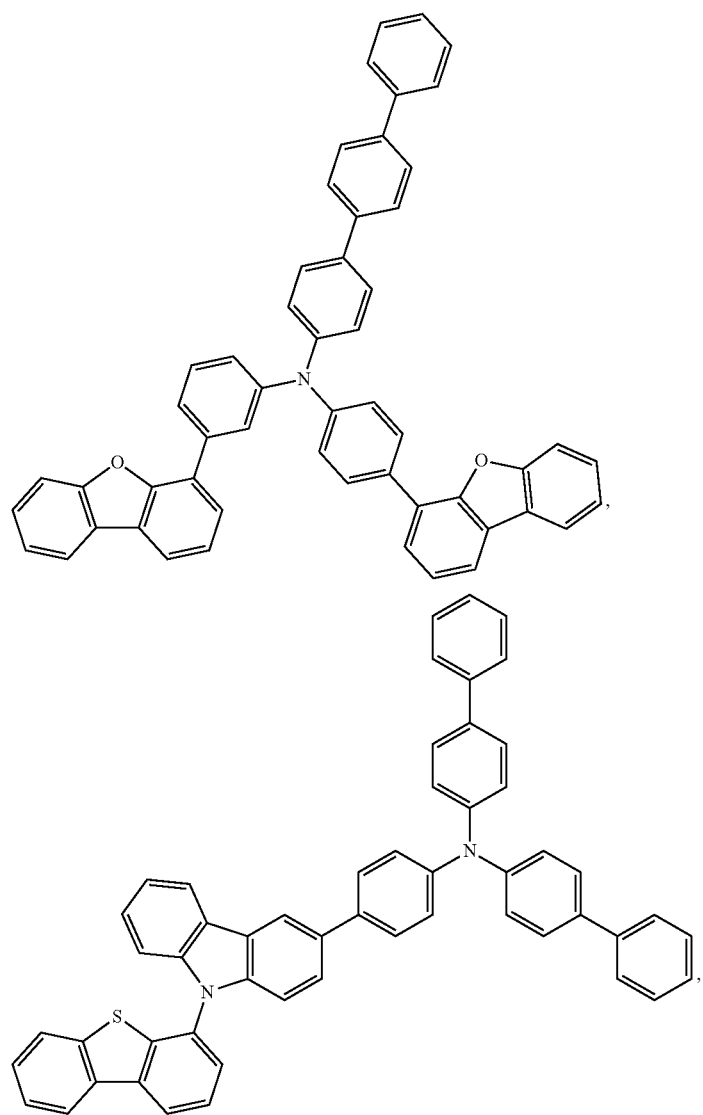

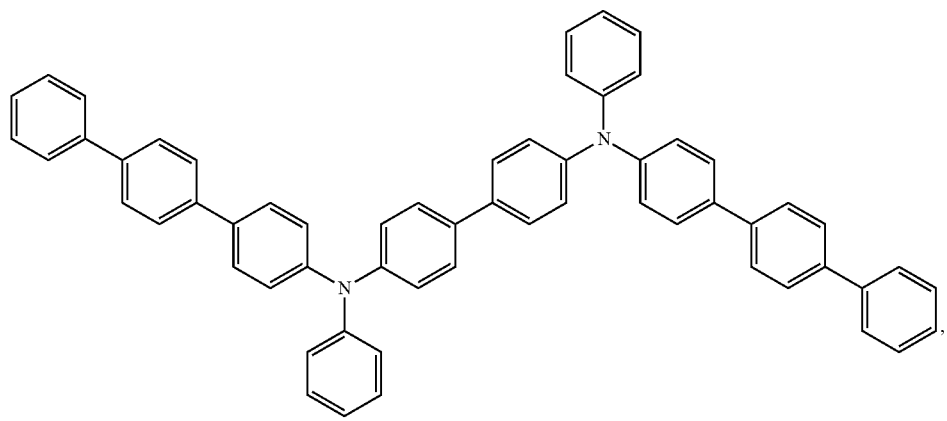
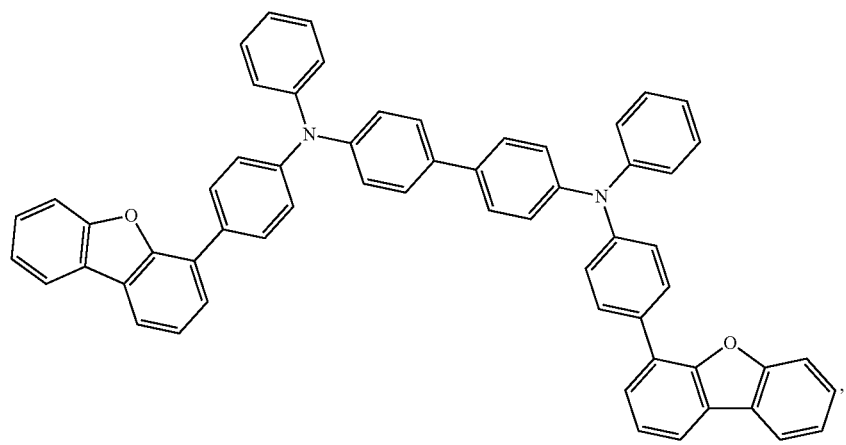
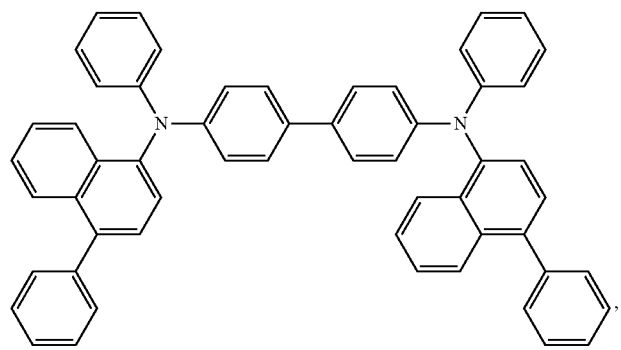

-continued
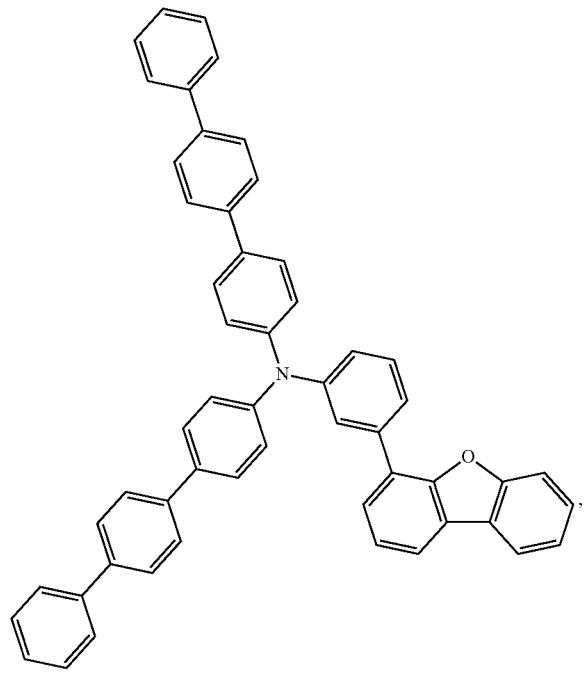
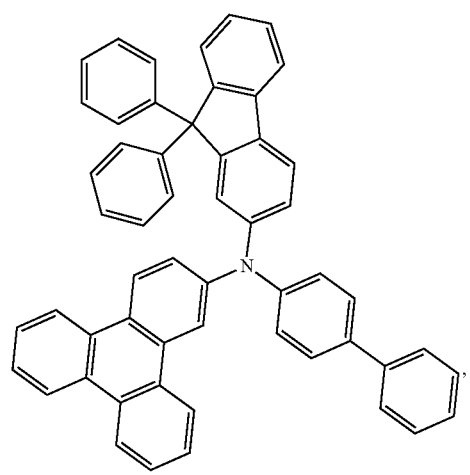
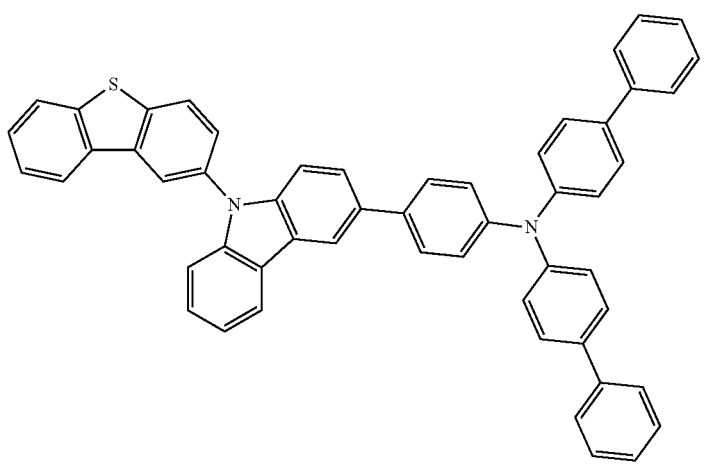
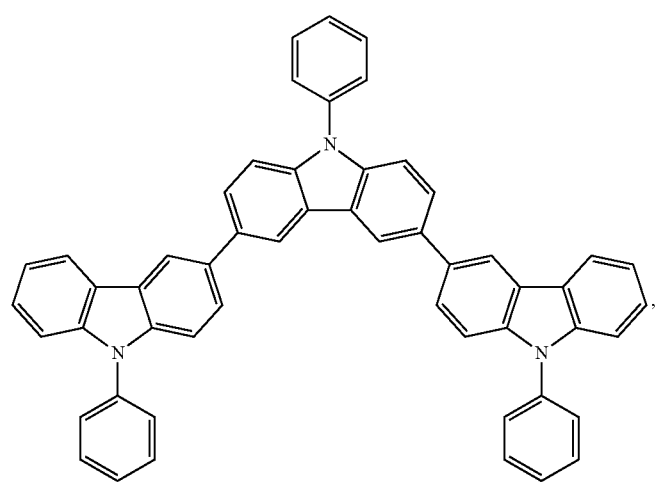
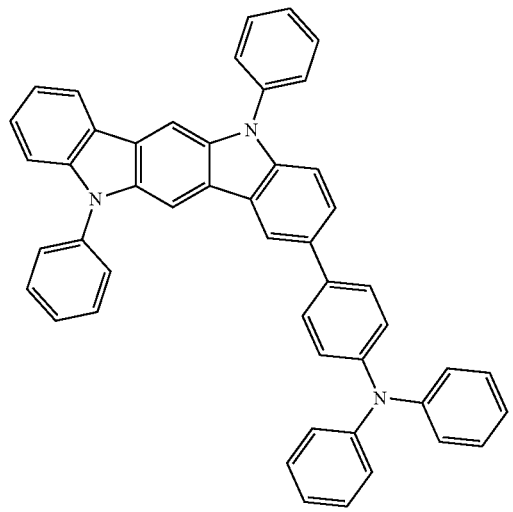

-continued
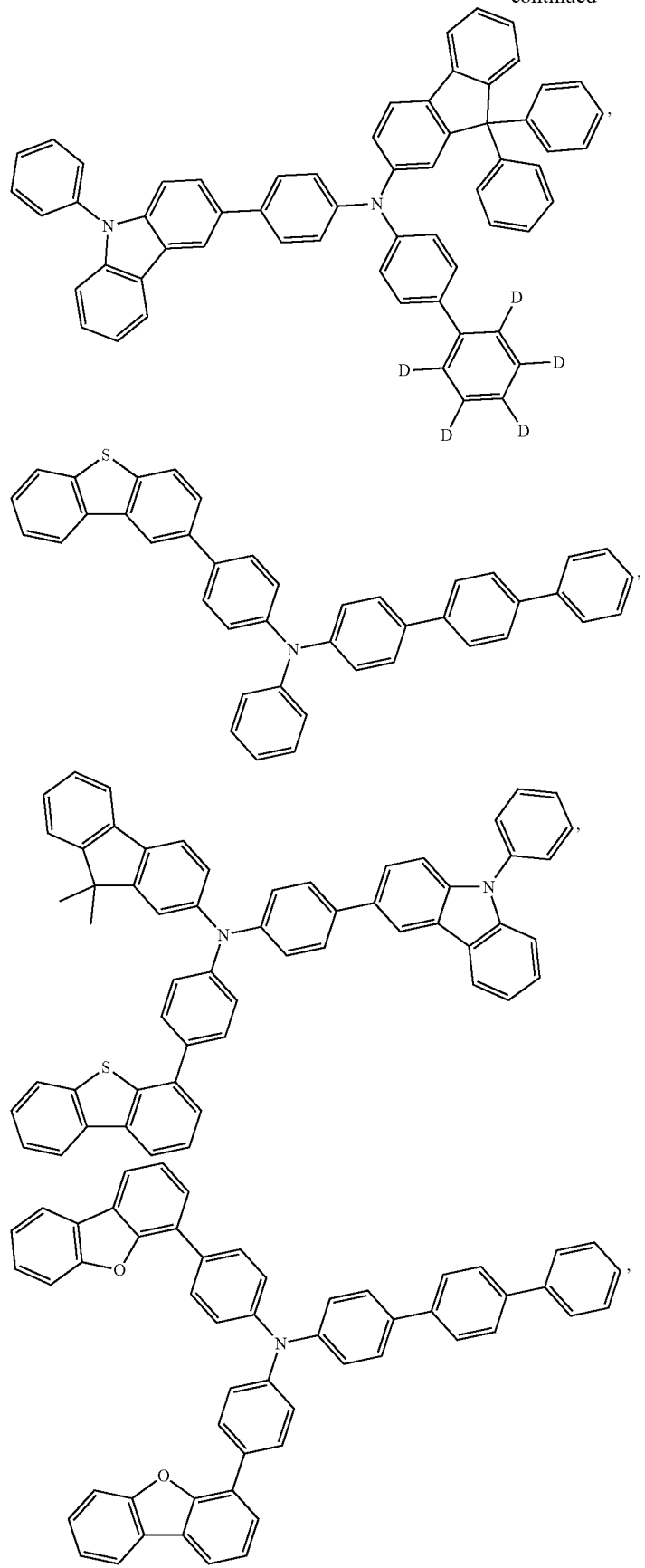

-continued
101
102
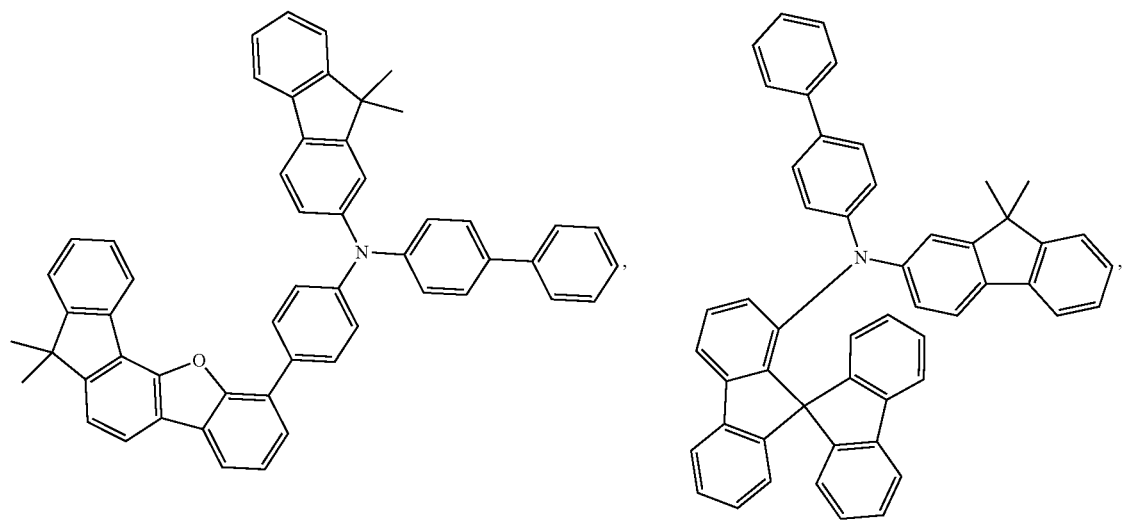
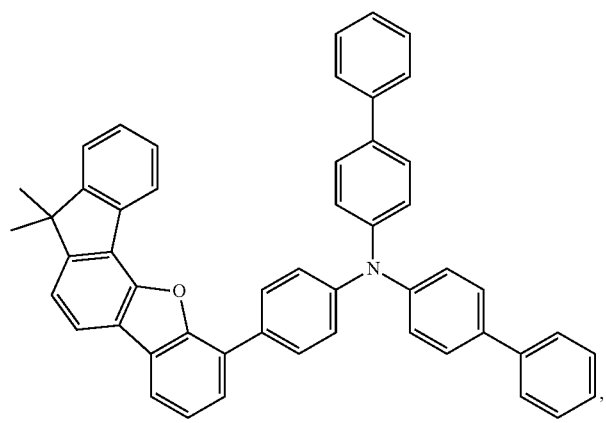
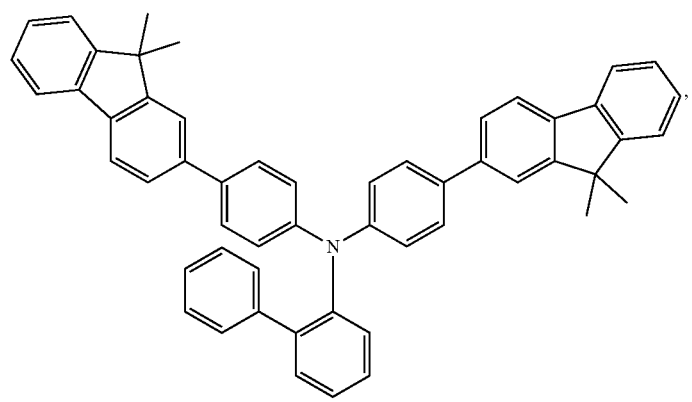

103 104
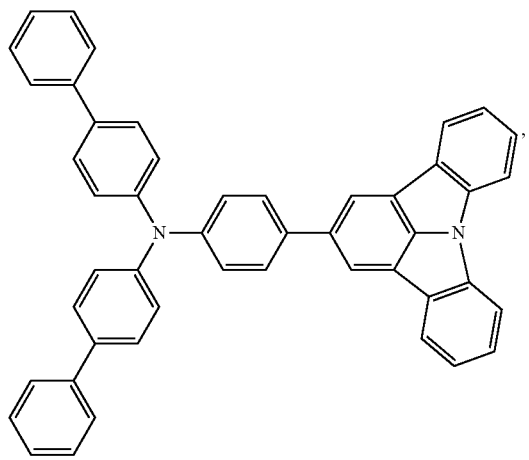
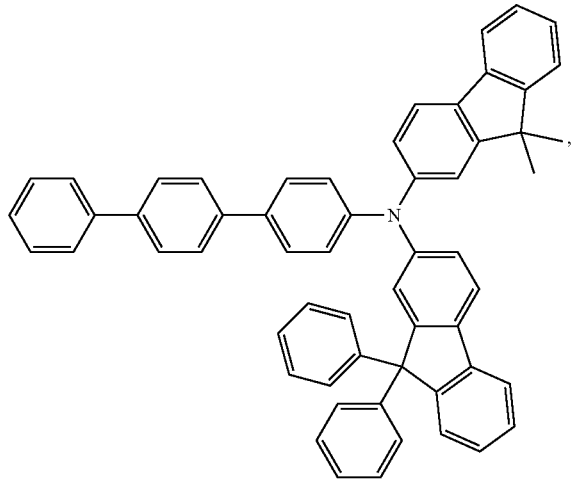
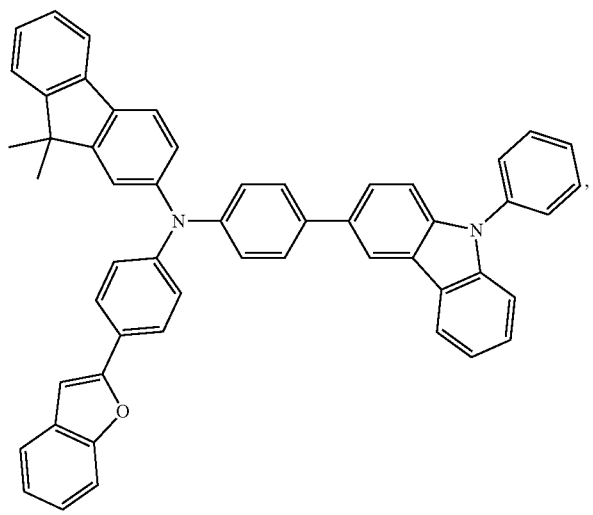
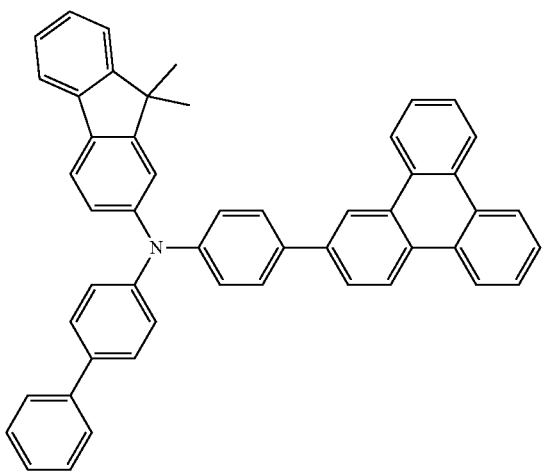
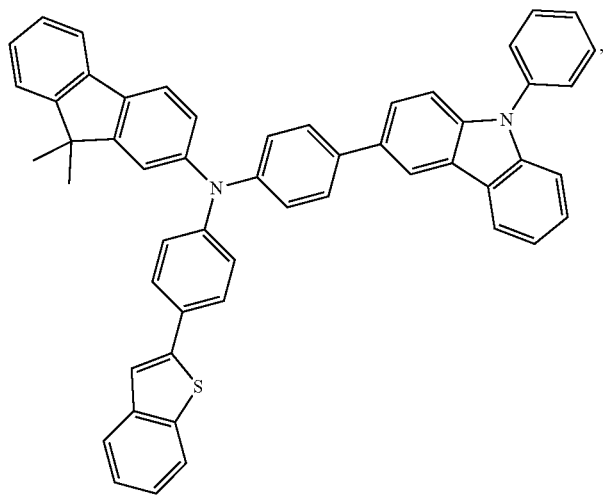

-continued
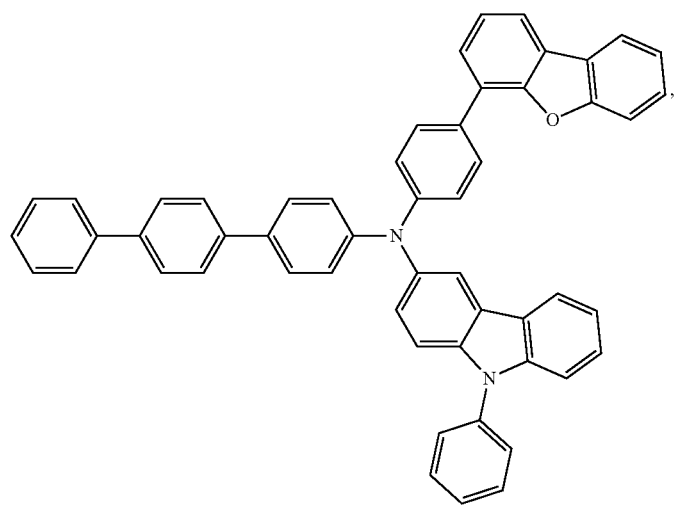
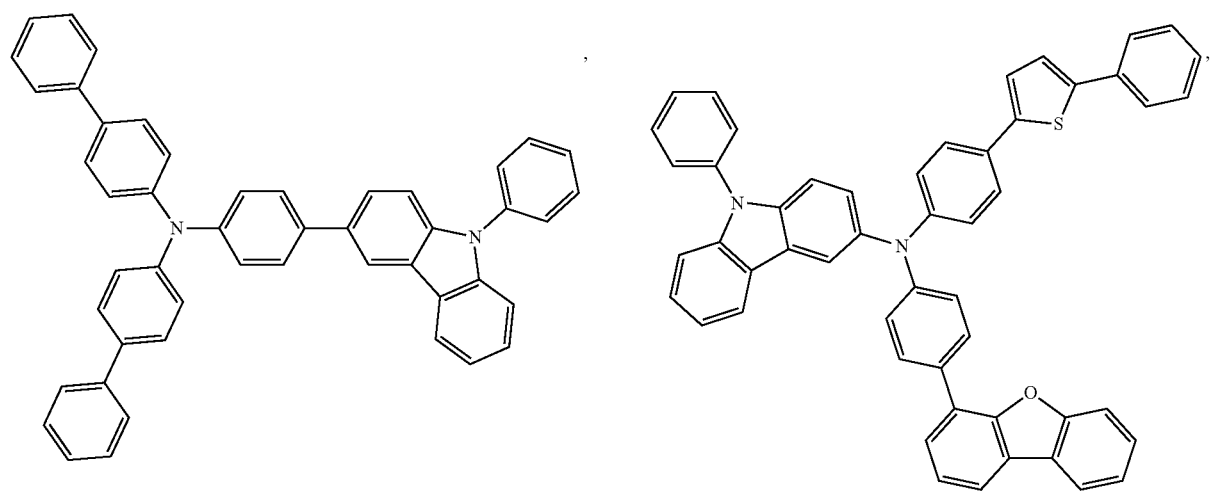
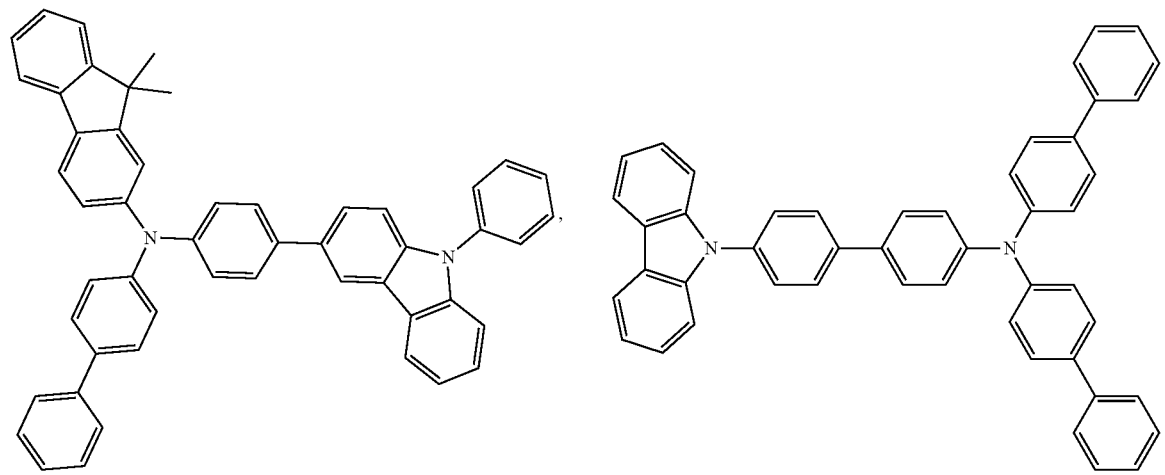

-continued
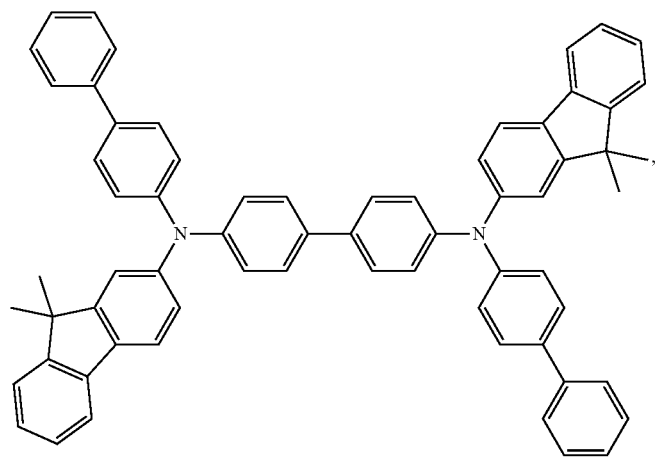
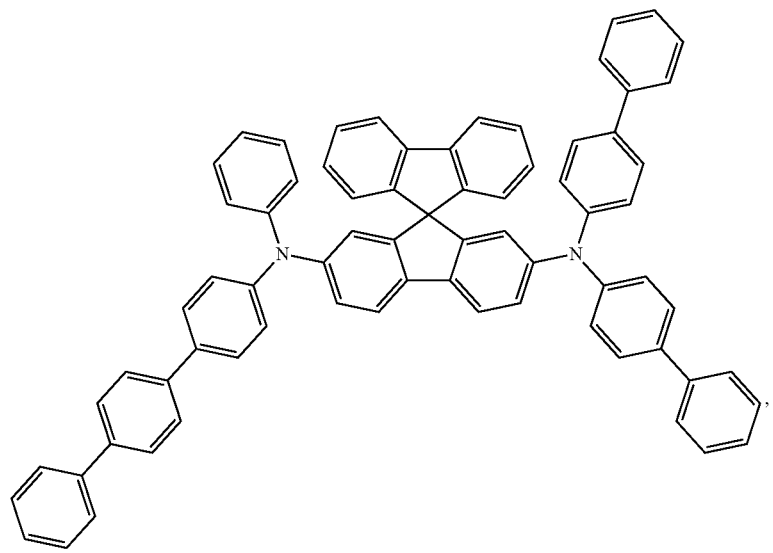
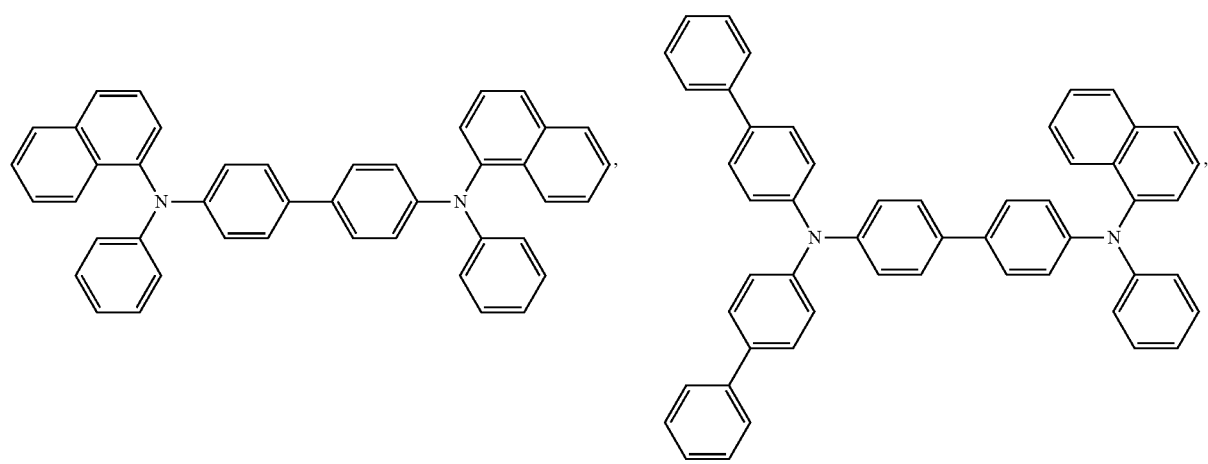

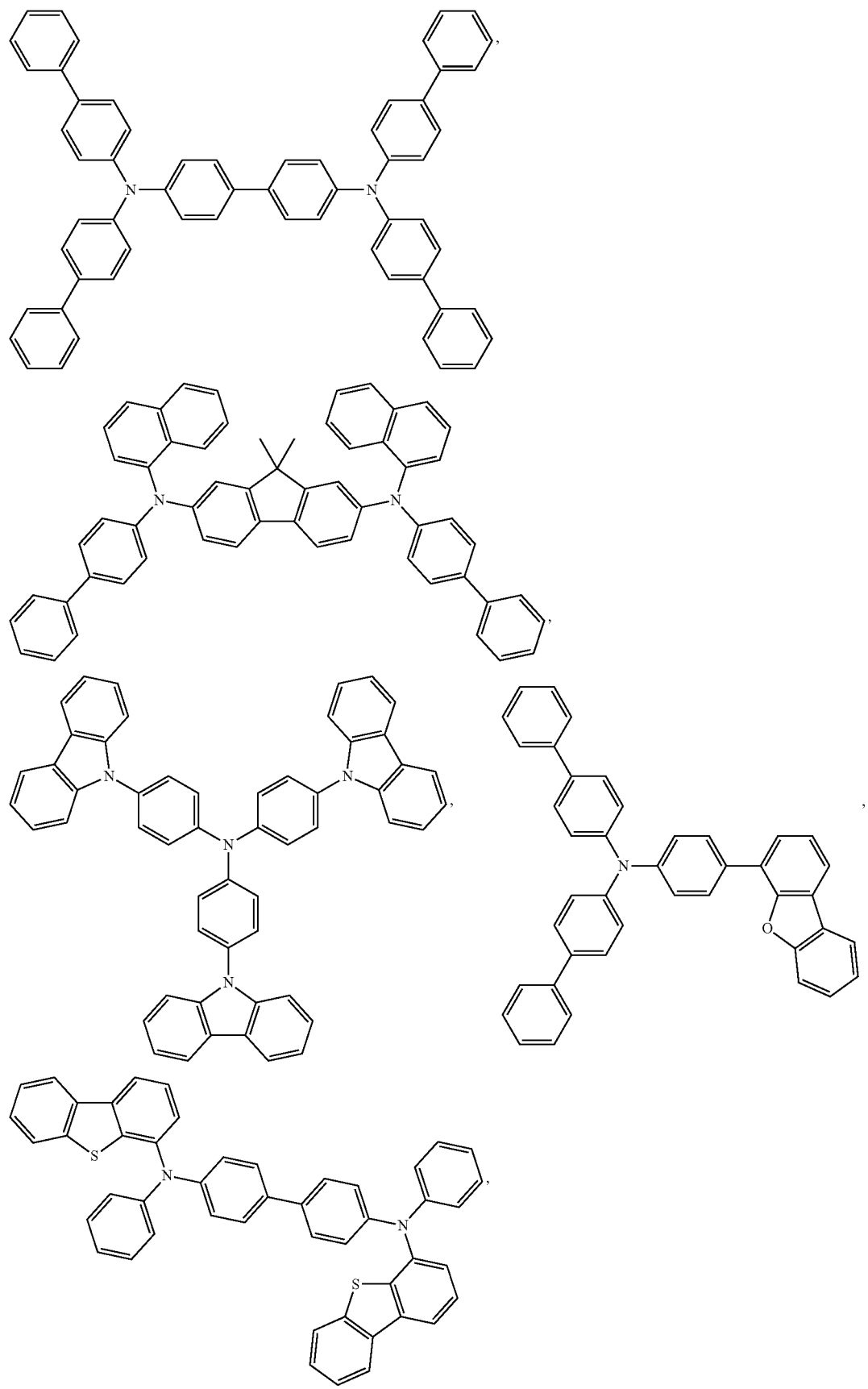

-continued

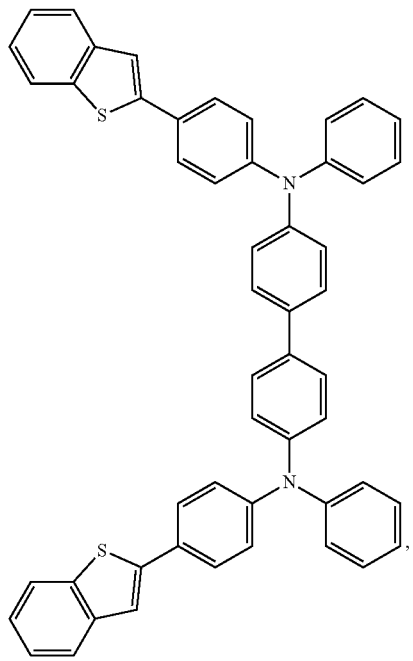

, and

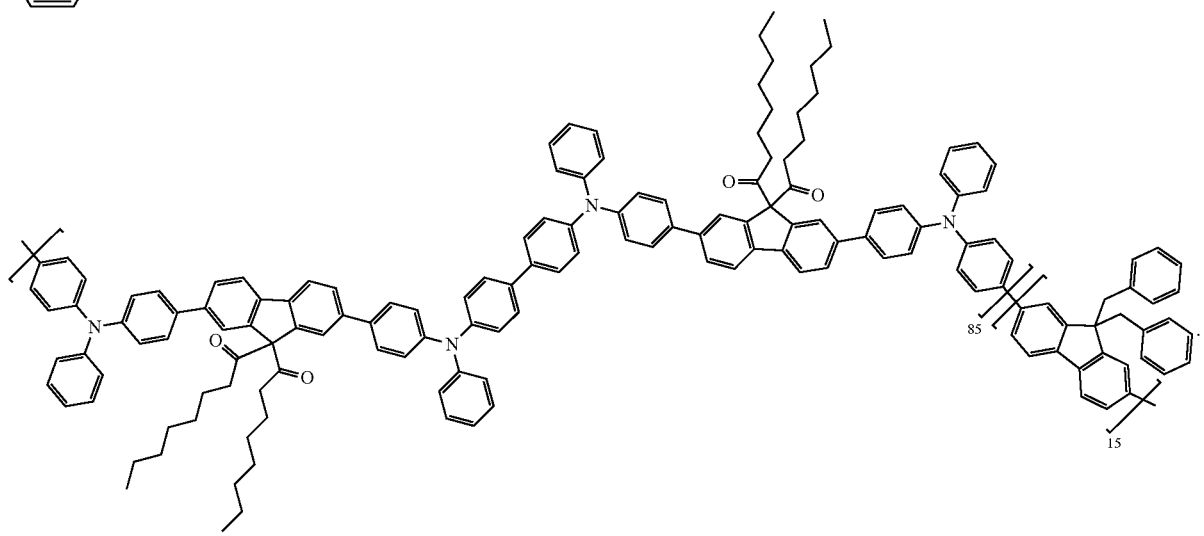

EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

Additional Hosts:

The light emitting layer of the organic EL device of the present invention preferably contains at least a metal complex as light emitting dopant material, and may contain one or more additional host materials using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

$$\left[\left(\begin{matrix}Y^{103}\\Y^{104}\end{matrix}\right)_{k'}\right] Met-(L^{101})_{k''}$$

wherein Met is a metal; $(Y^{103}-Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

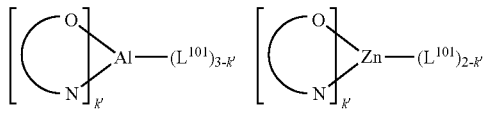

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

In one aspect, the host compound contains at least one of the following groups selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, host compound contains at least one of the following groups in the molecule:

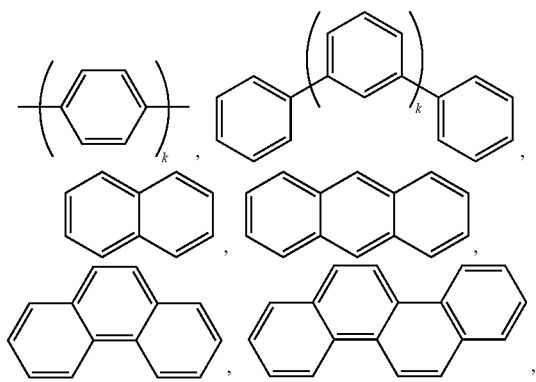

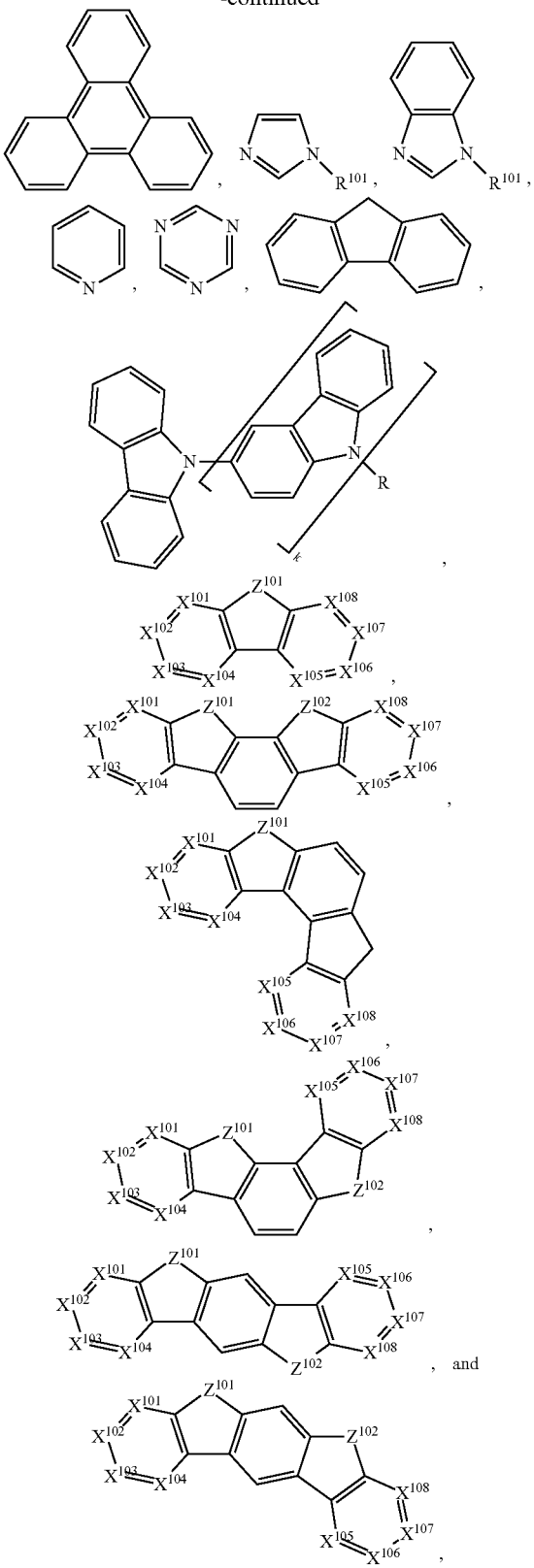

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20. $X^{101}$ to $X^{108}$ are independently selected from C (including CH) or N. $Z^{101}$ and $Z^{102}$ are independently selected from $NR^{101}$, O, or S.

Non-limiting examples of the additional host materials that may be used in an OLED in combination with the host compound disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803.

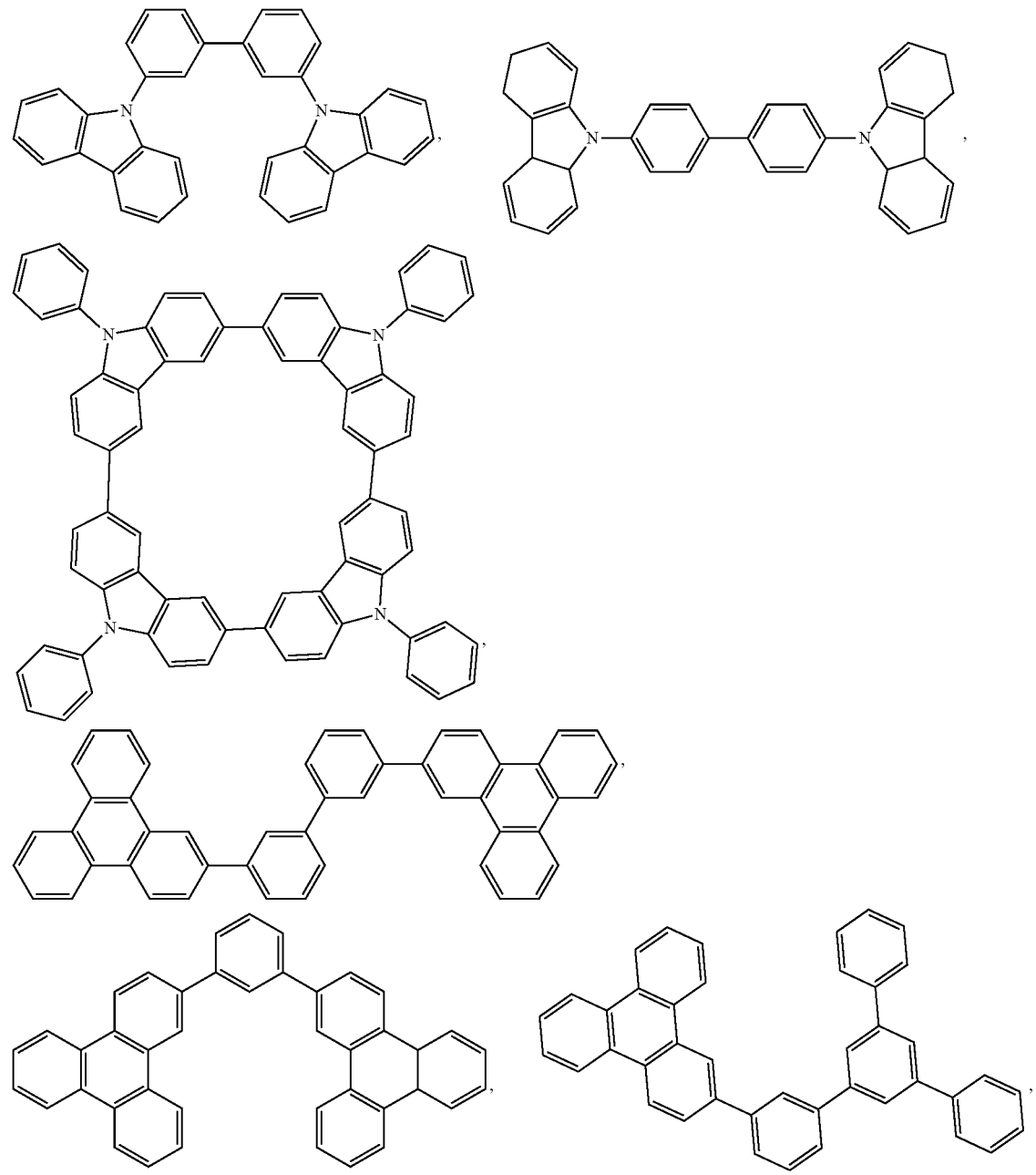

117
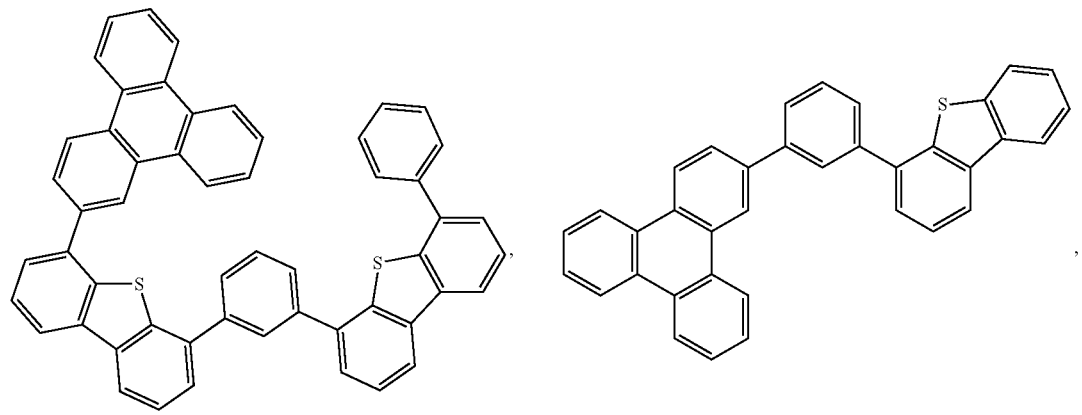
118
-continued
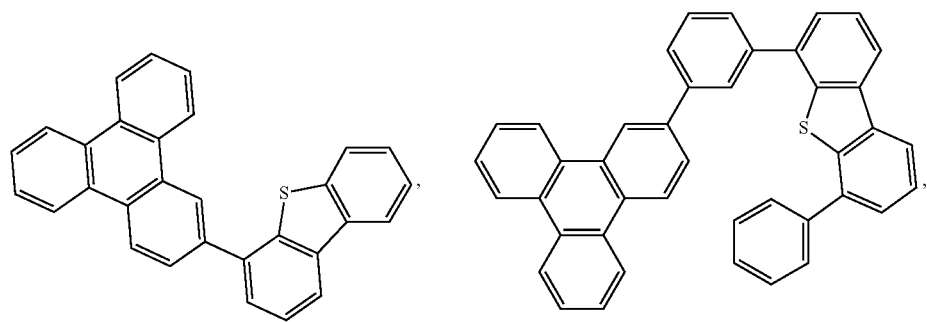
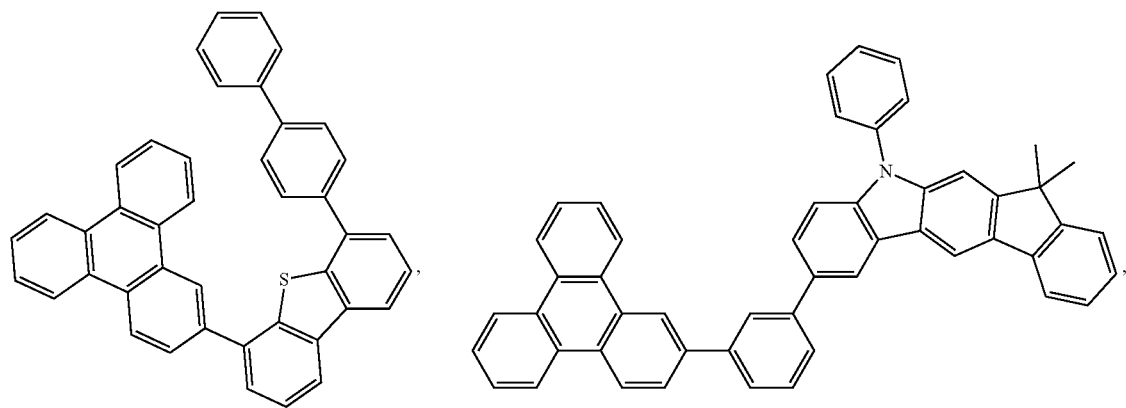
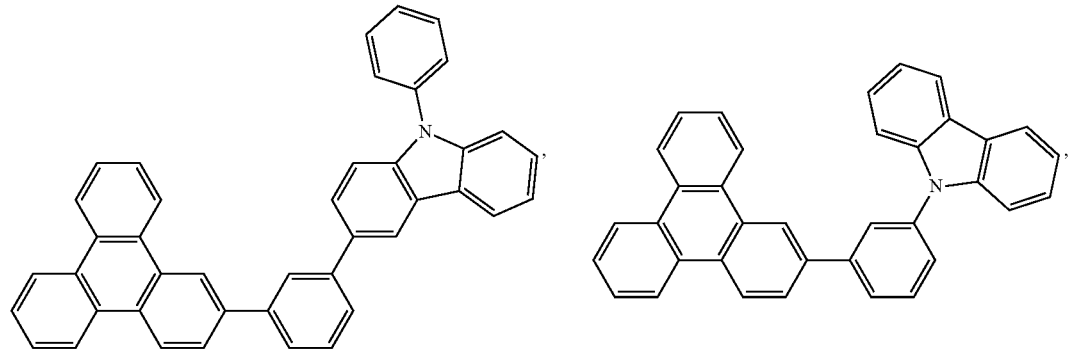

119 120
-continued
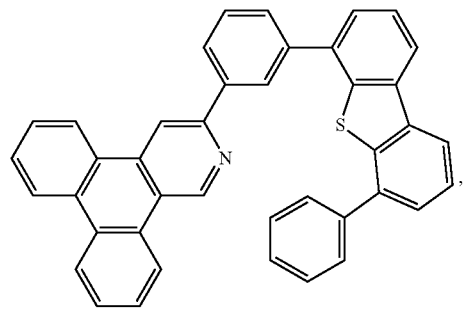,
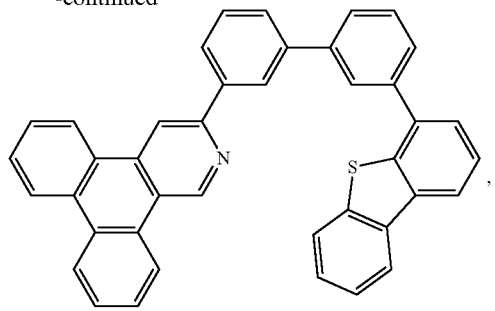,
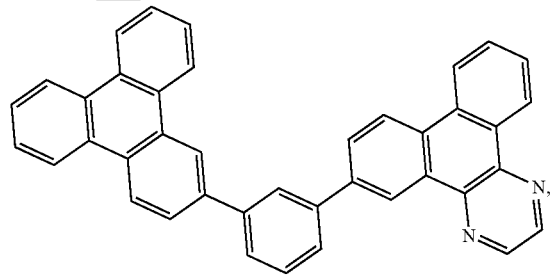,
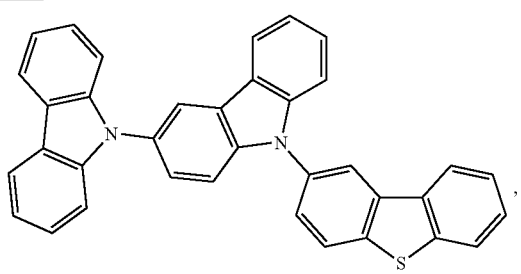,
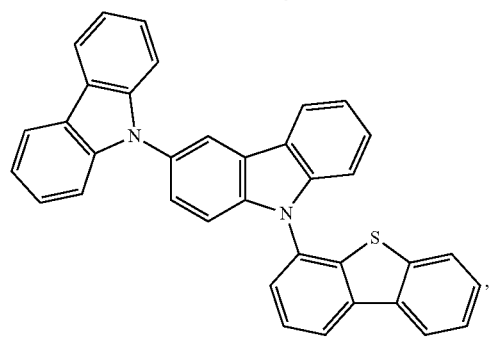,
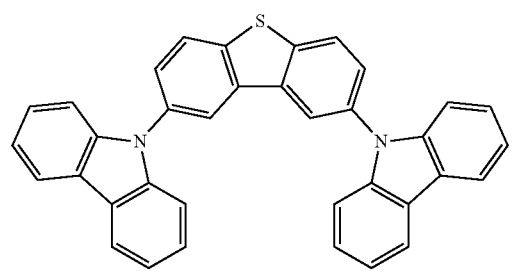,
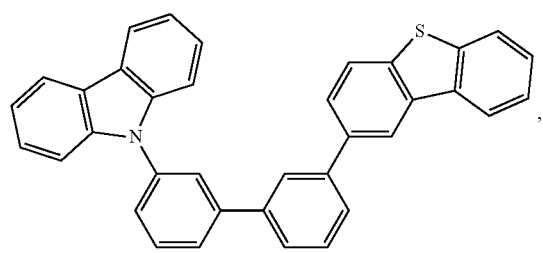,
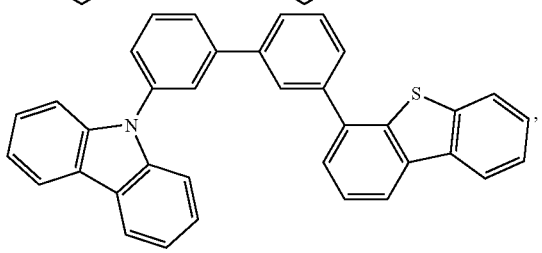,
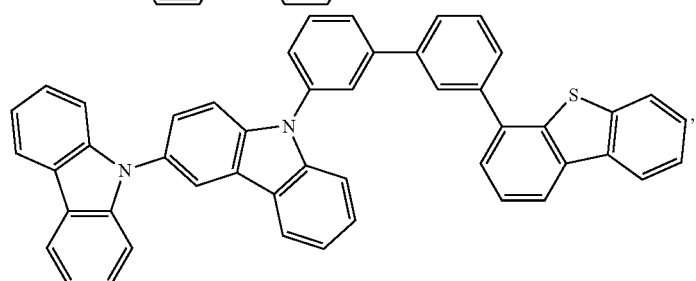,
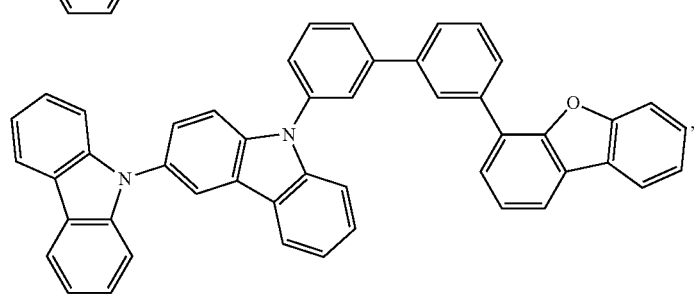,

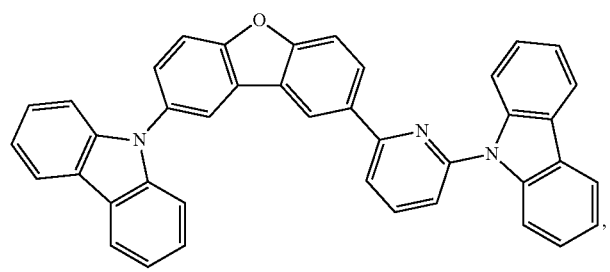
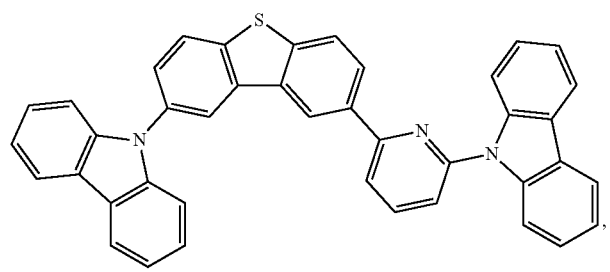
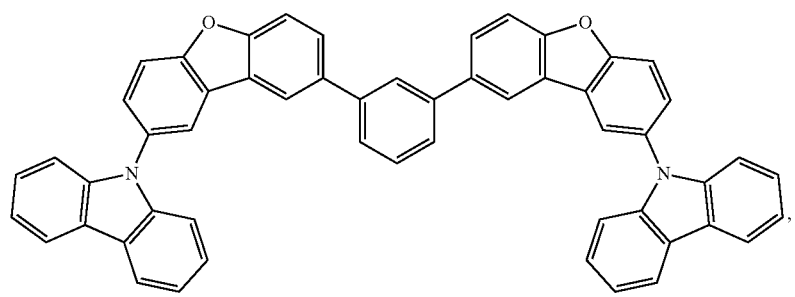
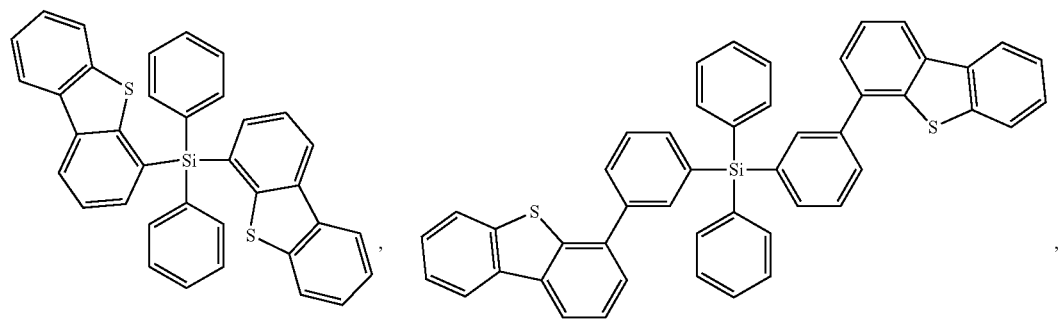
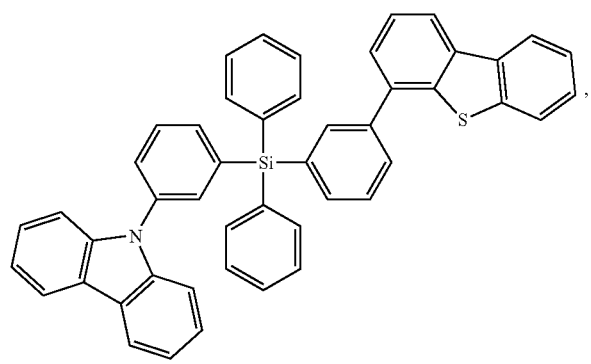

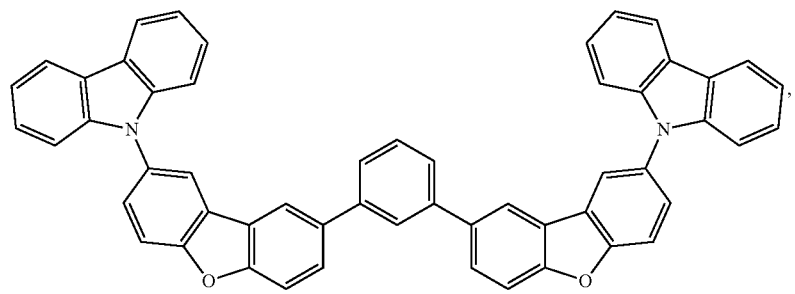
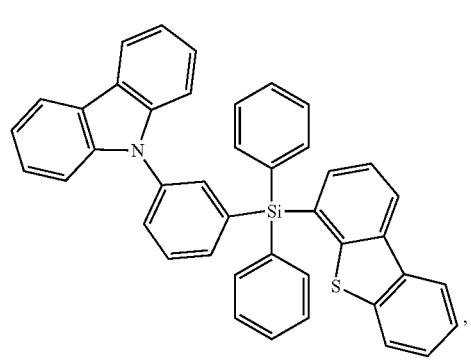
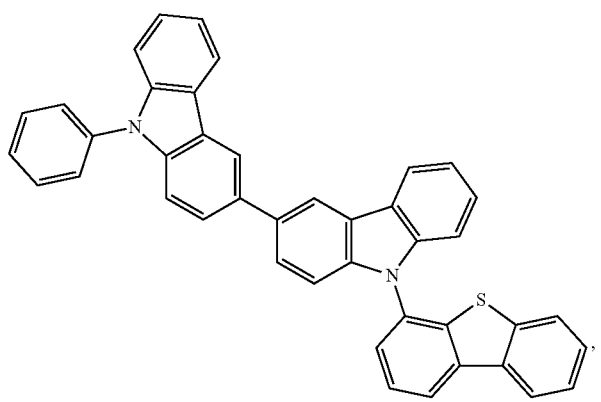
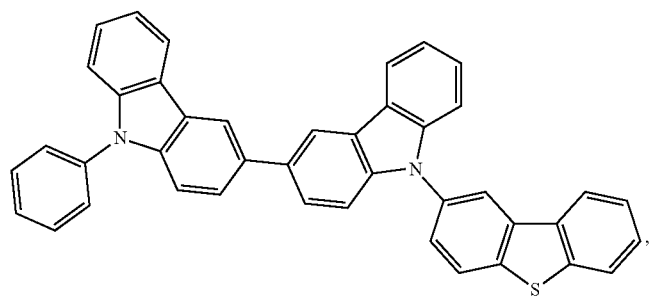
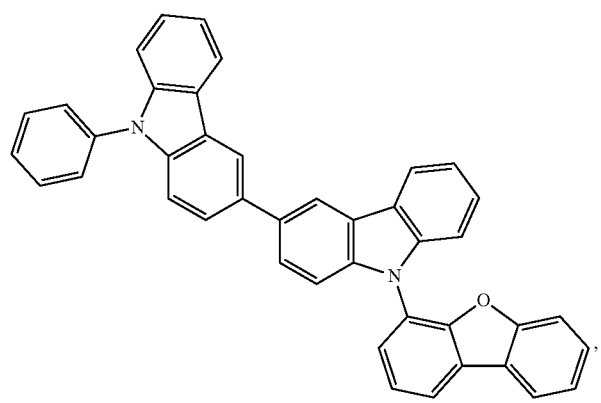

125
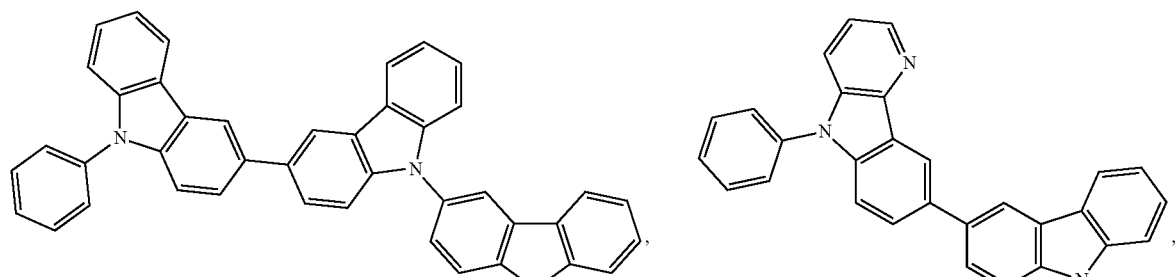
126
-continued
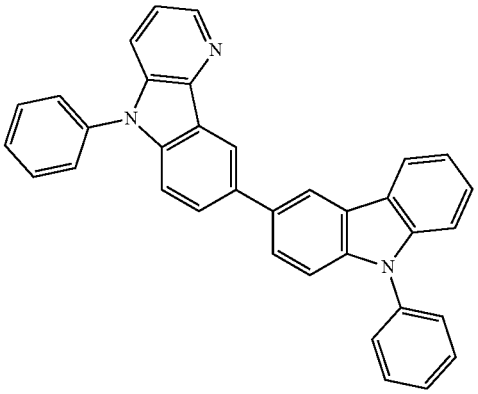
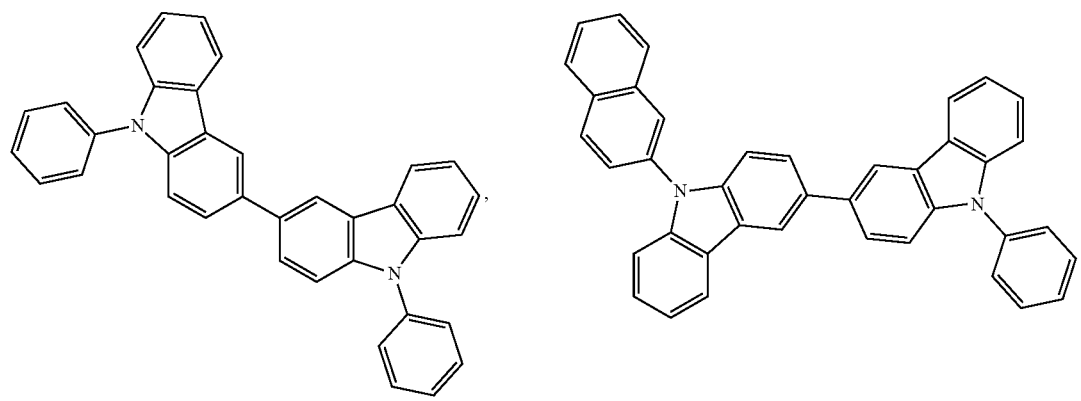
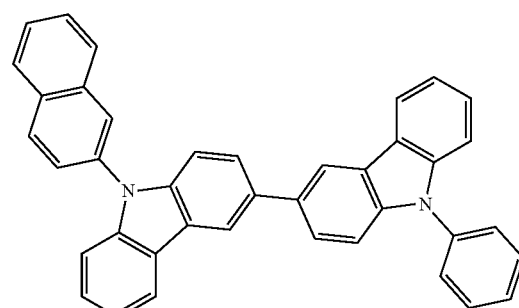
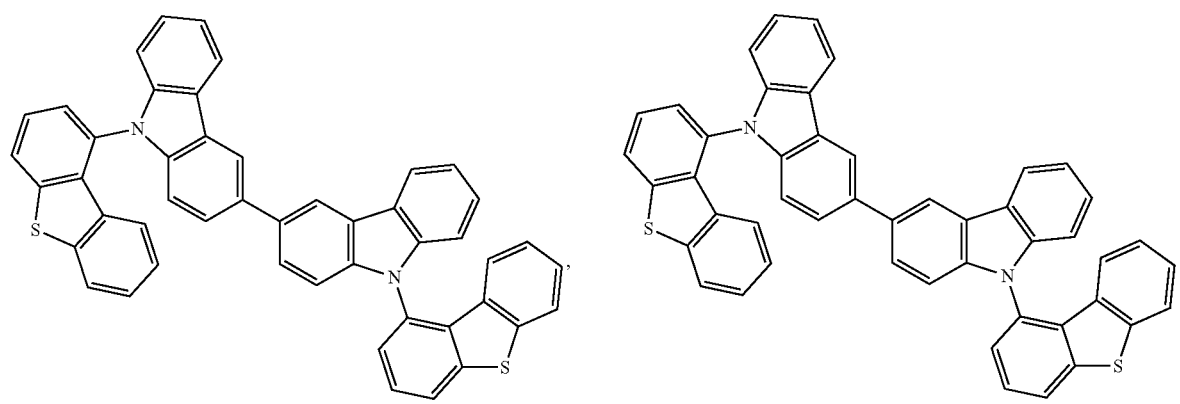
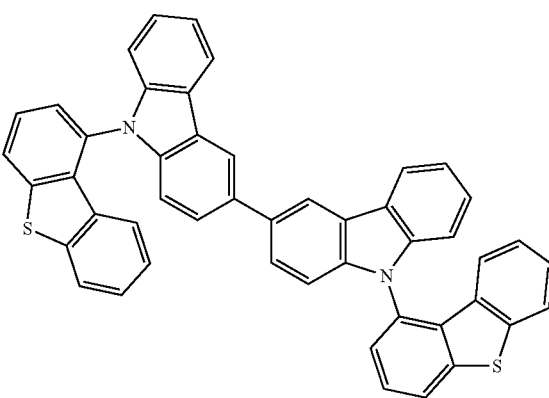
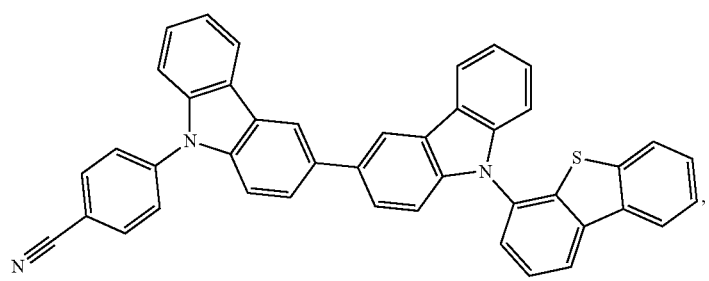

-continued
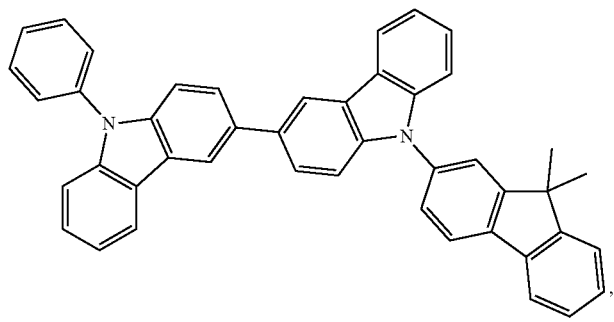
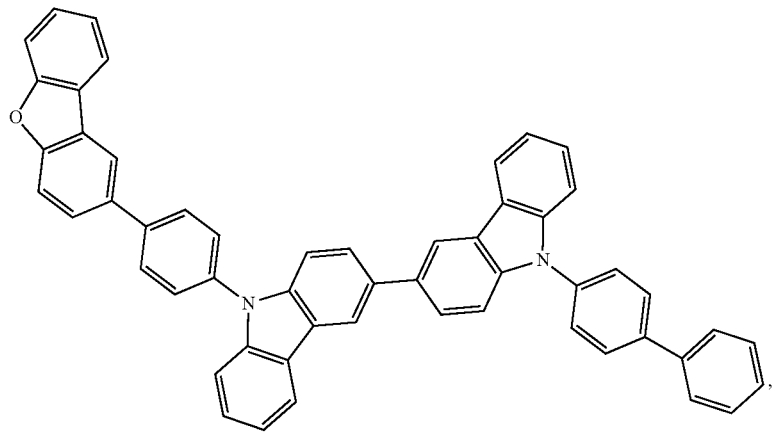
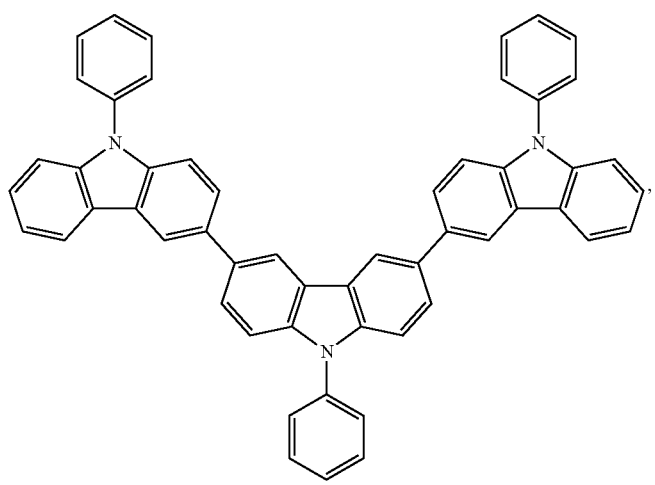
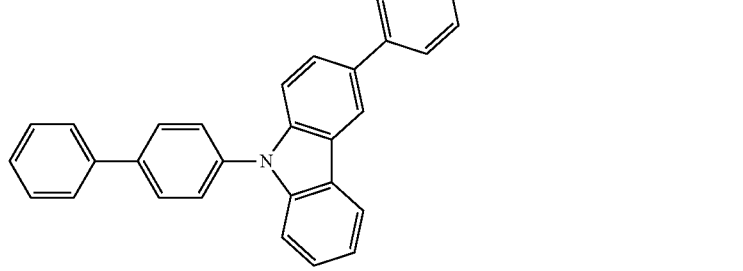

-continued
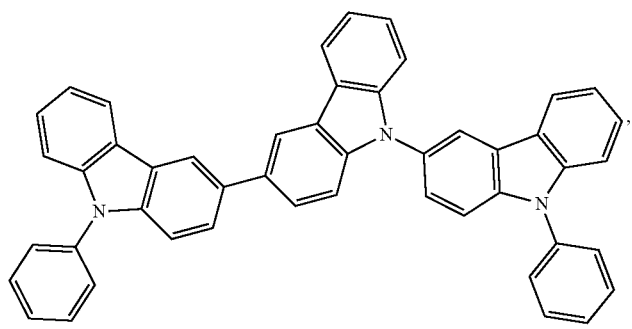
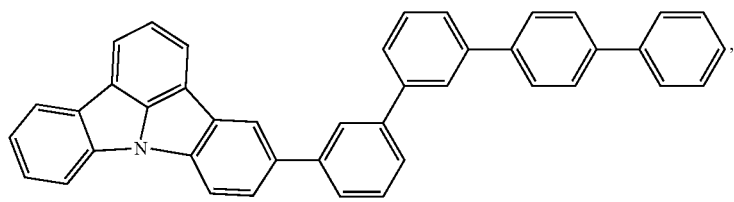
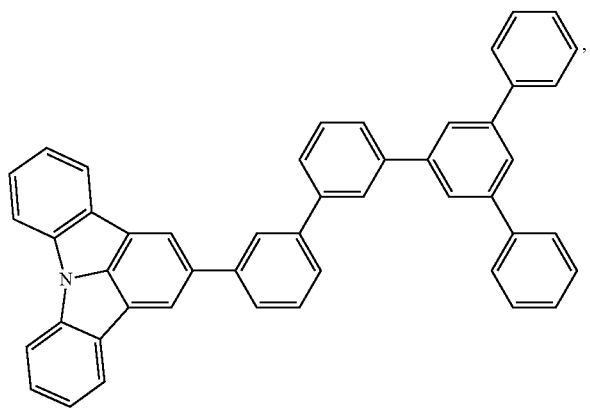
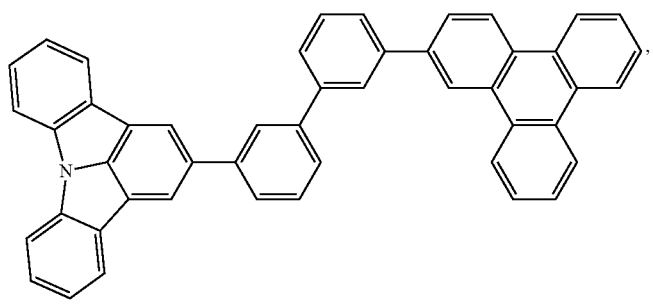
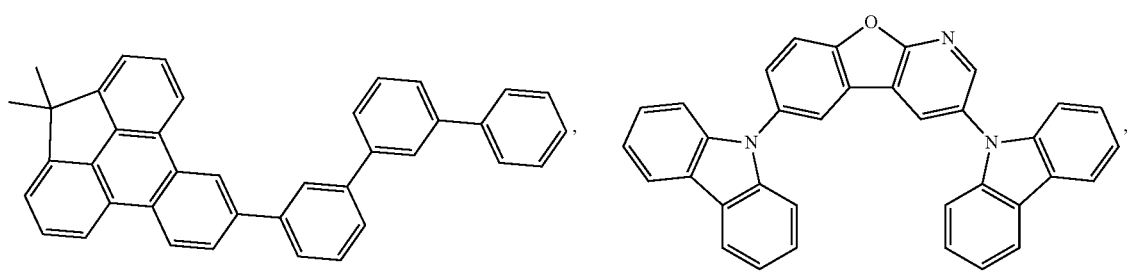

-continued
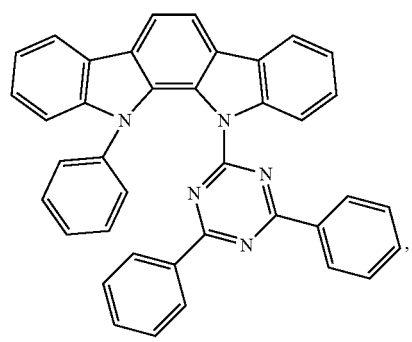
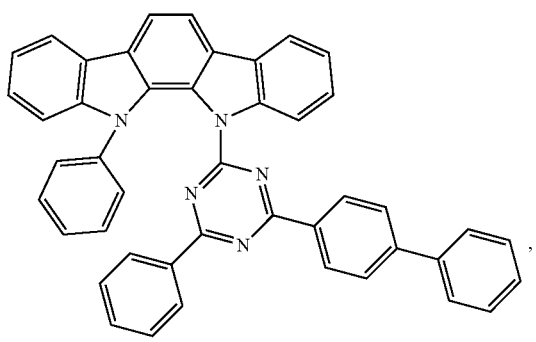
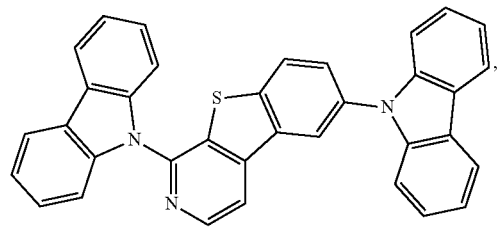
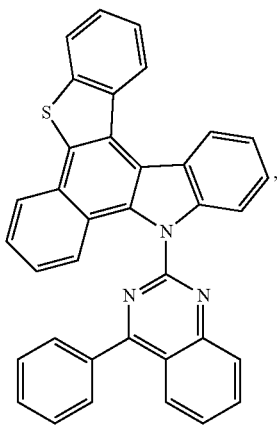
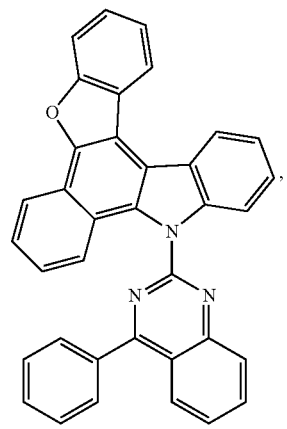
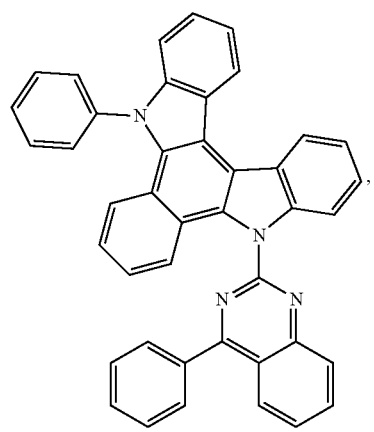
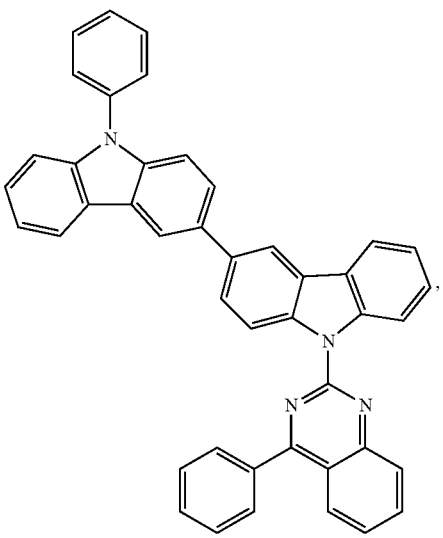
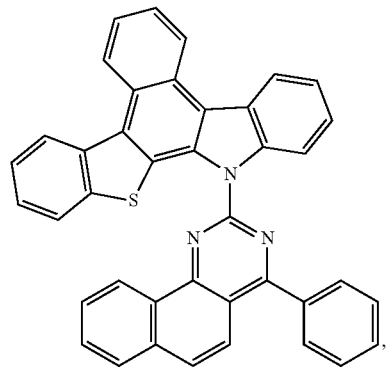
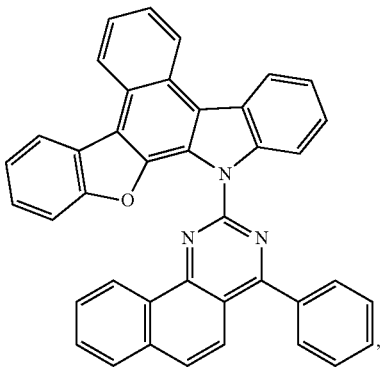

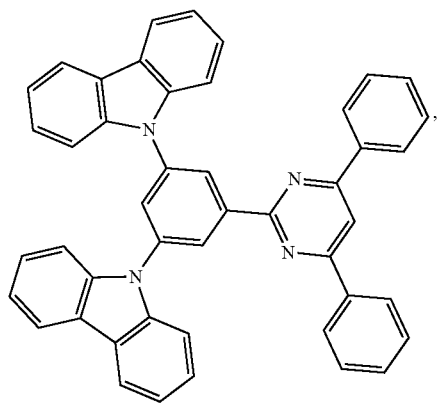,
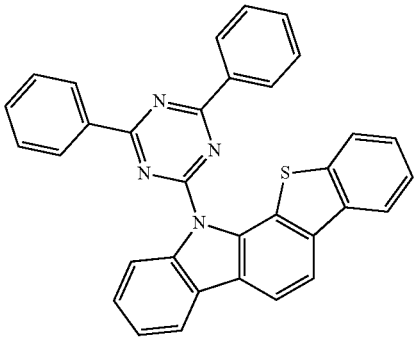,
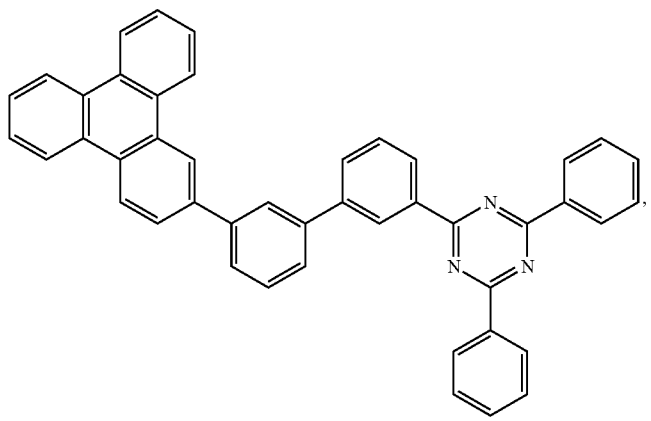,
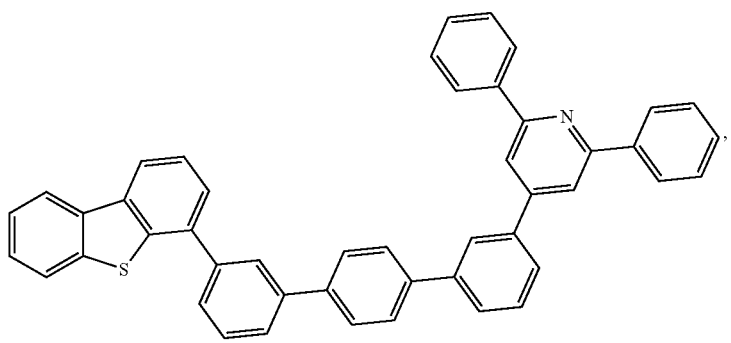,
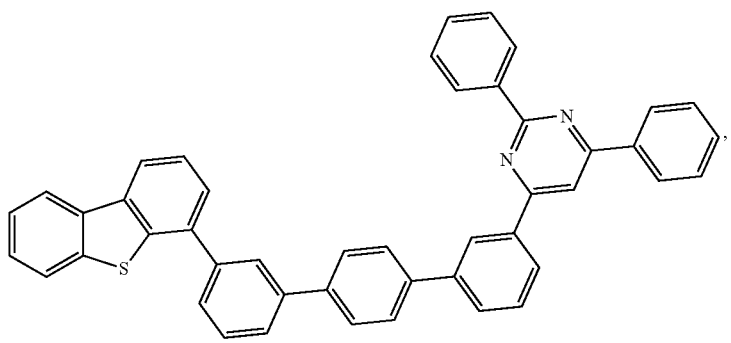,

-continued
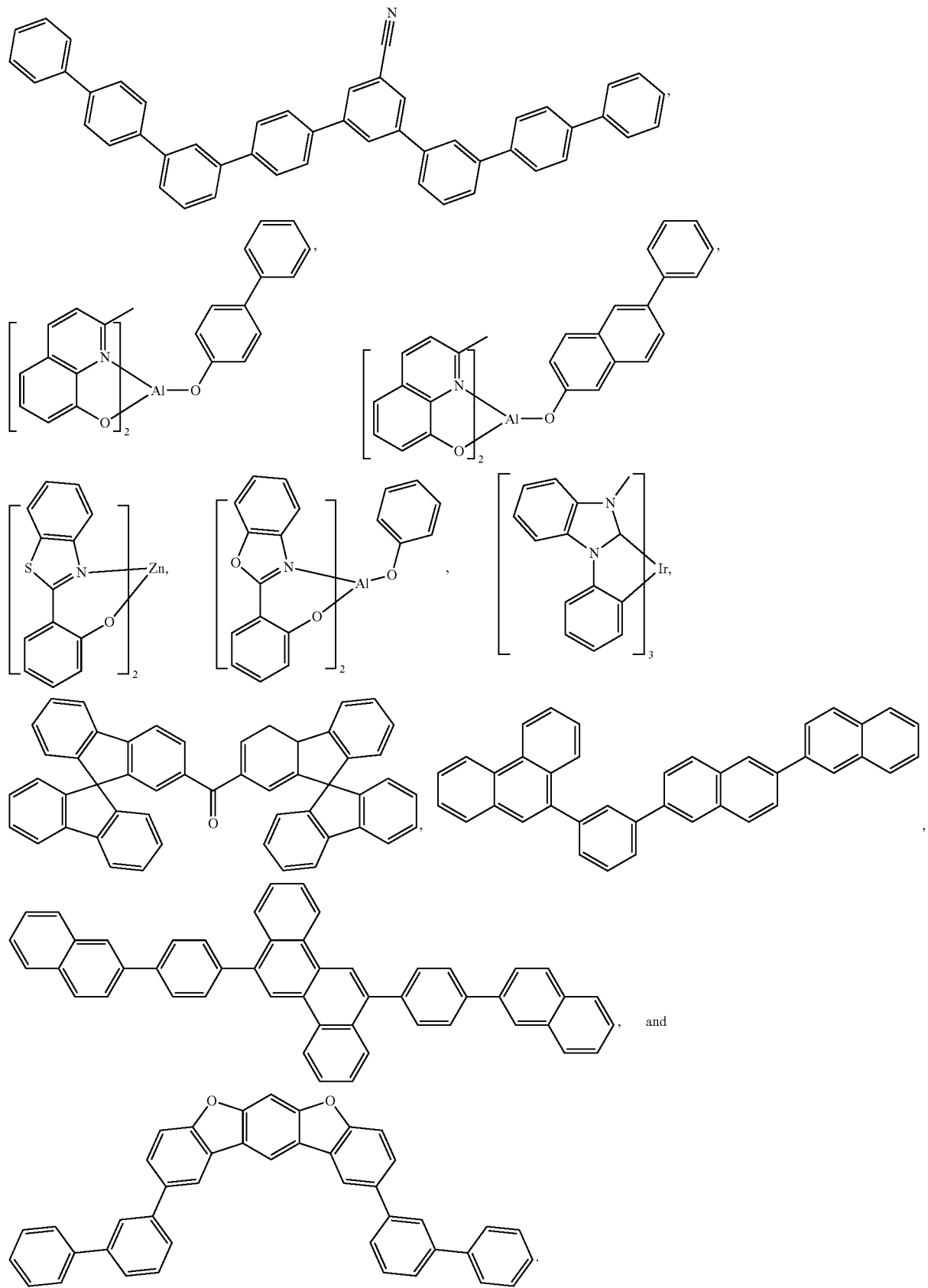

Emitter:

An emitter example is not particularly limited, and any compound may be used as long as the compound is typically used as an emitter material. Examples of suitable emitter materials include, but are not limited to, compounds which can produce emissions via phosphorescence, fluorescence, thermally activated delayed fluorescence, i.e., TADF (also referred to as E-type delayed fluorescence; see, e.g., U.S. application Ser. No. 15/700,352, which is hereby incorporated by reference in its entirety), triplet-triplet annihilation, or combinations of these processes. In some embodiments, the emissive dopant can be a racemic mixture, or can be enriched in one enantiomer.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450,

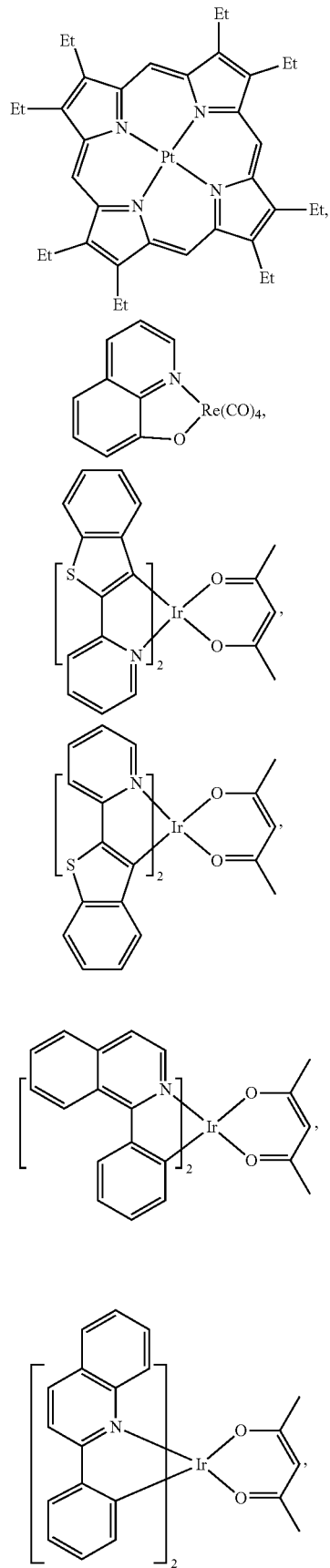

139
-continued
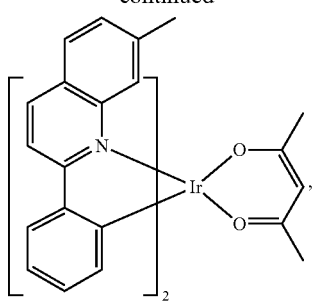
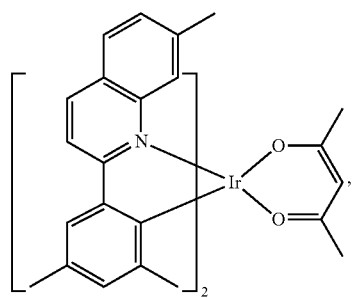
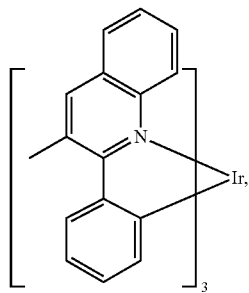
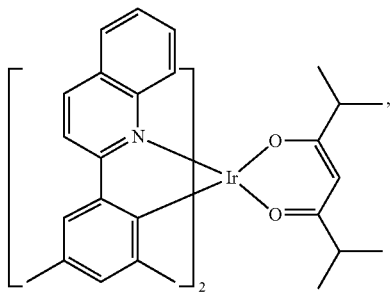
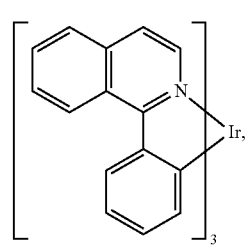
140
-continued
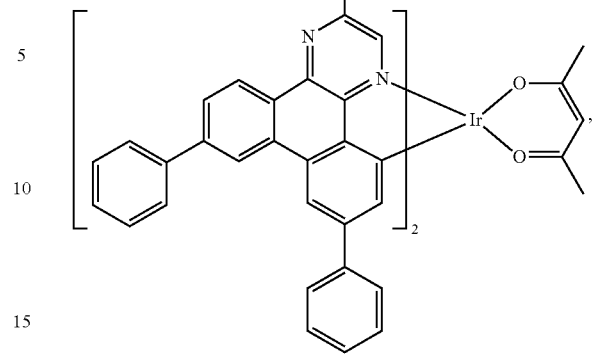
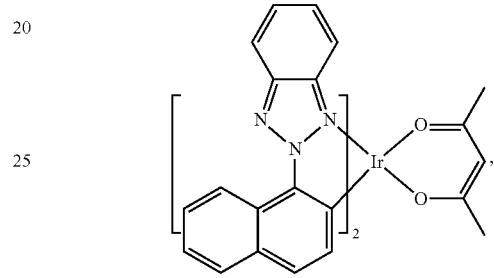
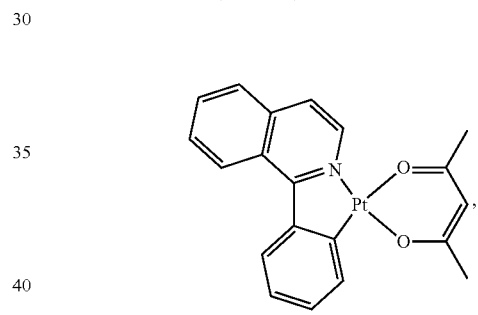
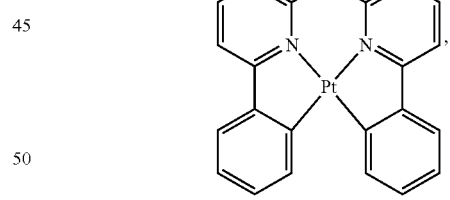
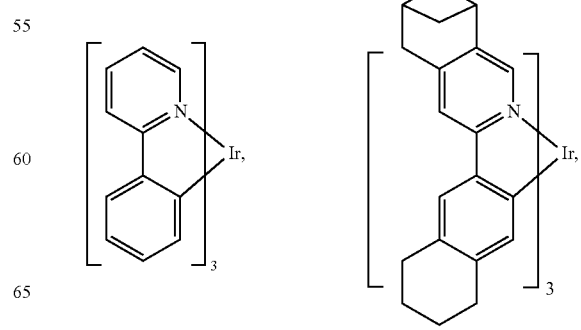

141
-continued
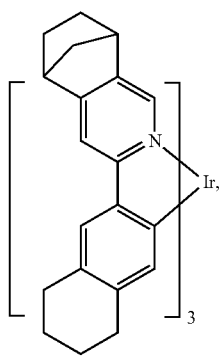
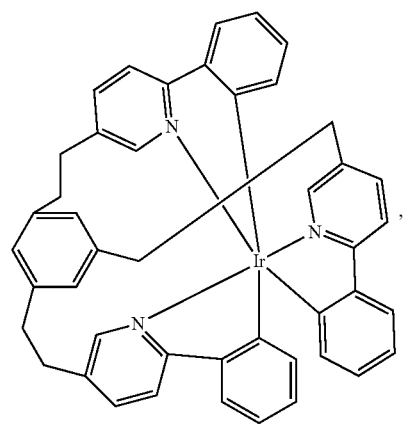
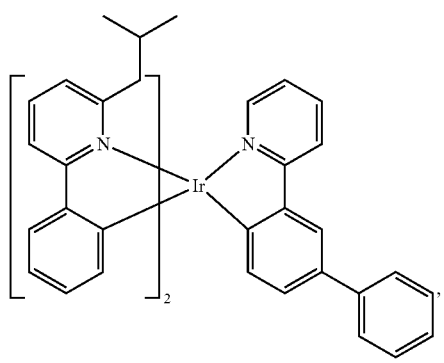
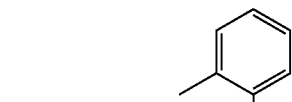
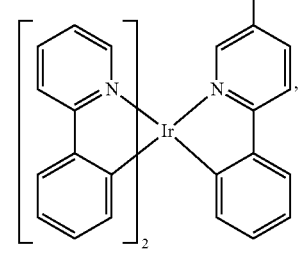
142
-continued
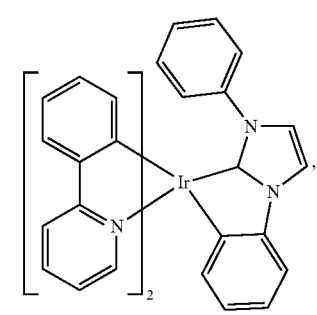
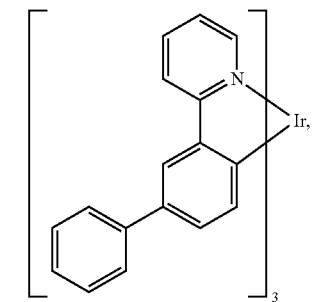
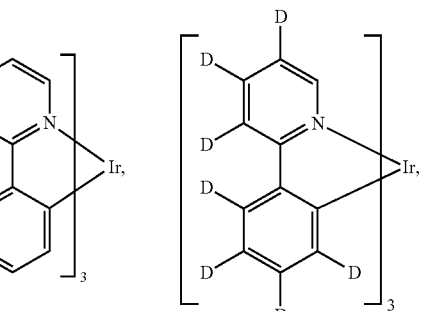
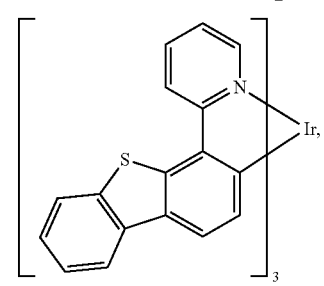
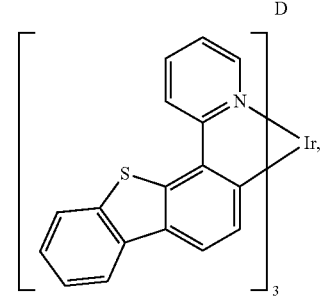

-continued
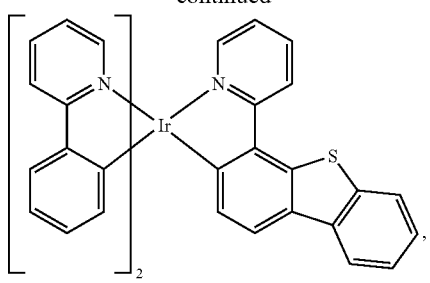
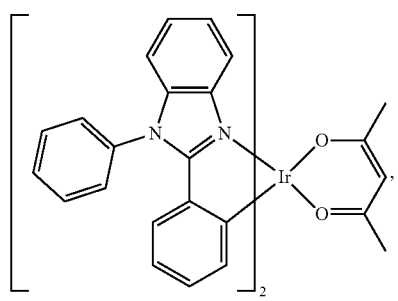
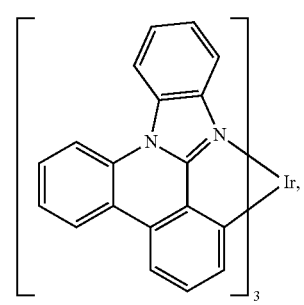
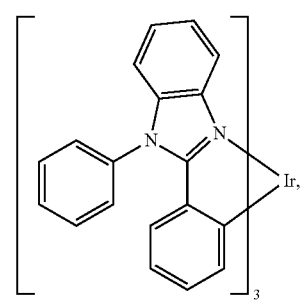
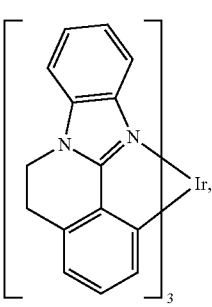
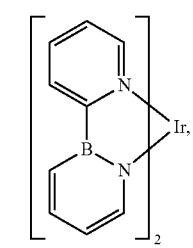
-continued
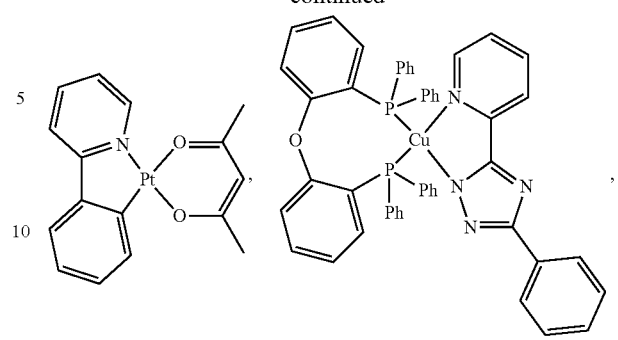
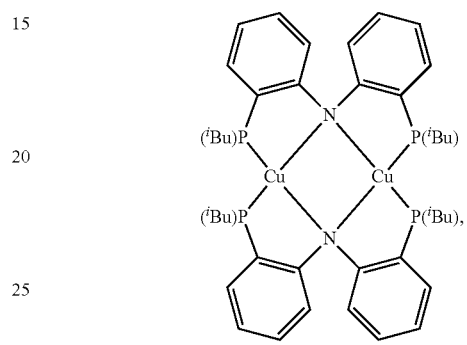
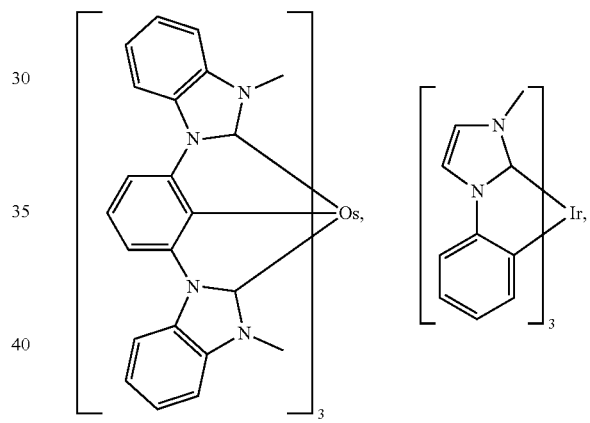
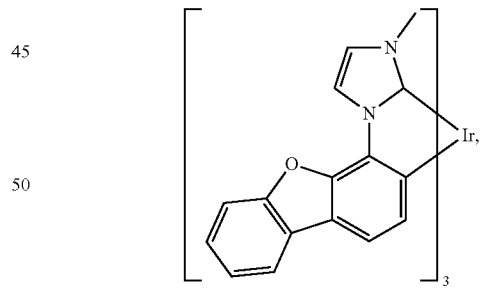
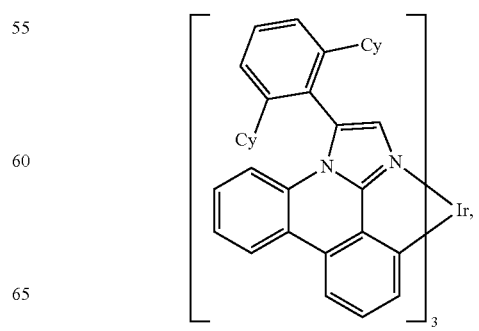

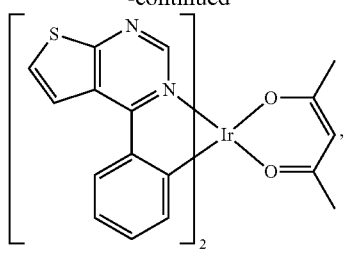
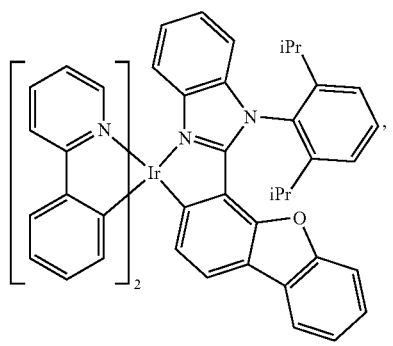
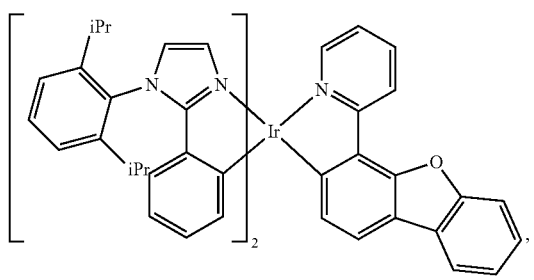
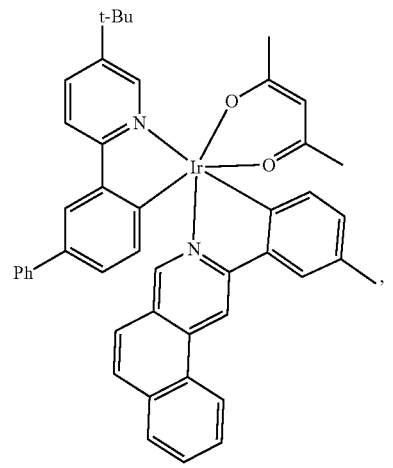
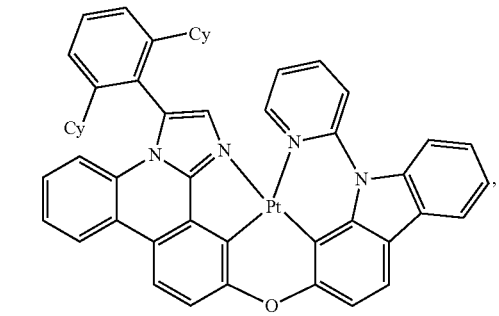
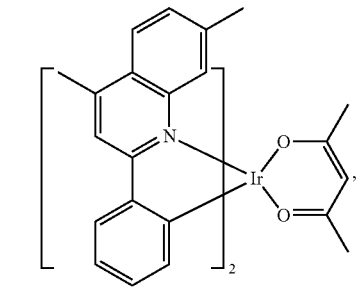
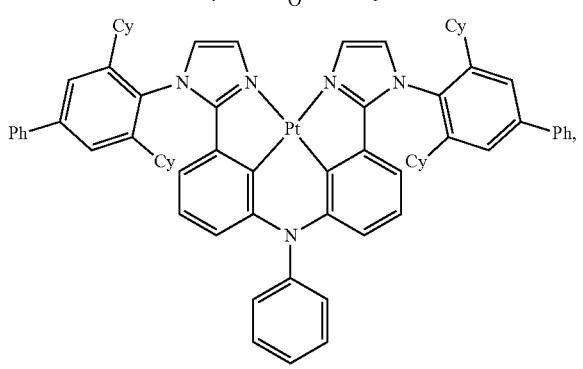
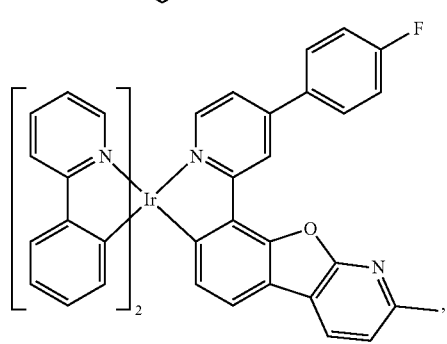
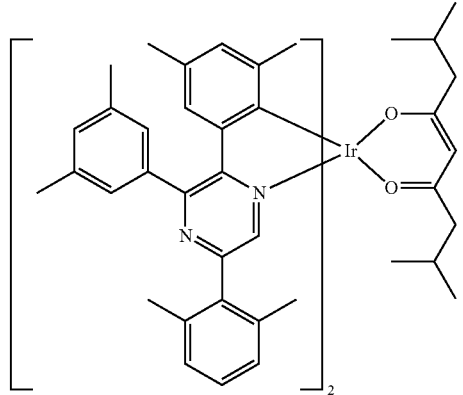
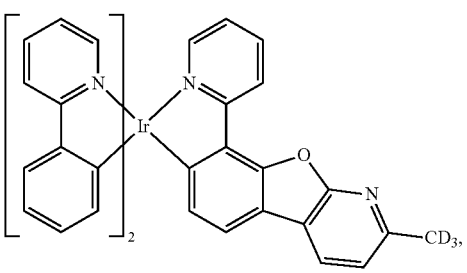

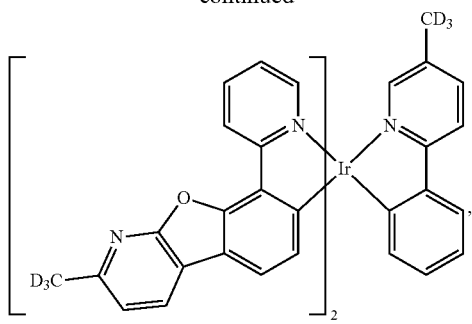
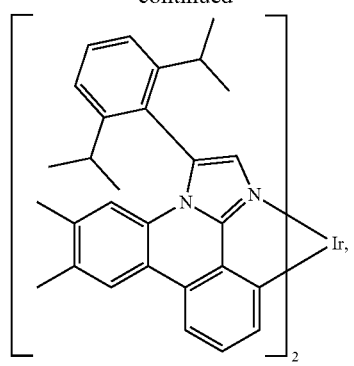
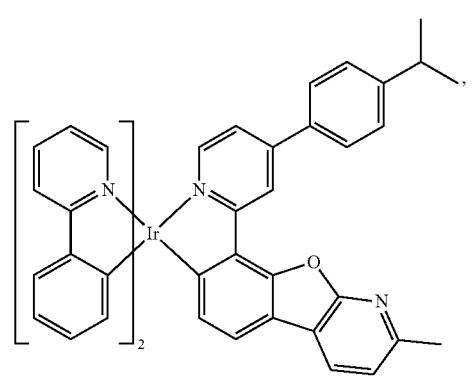
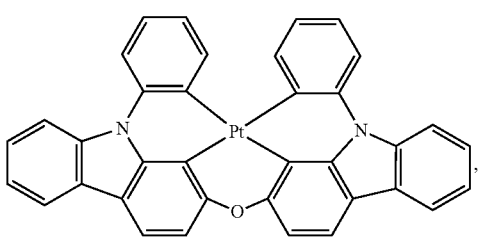
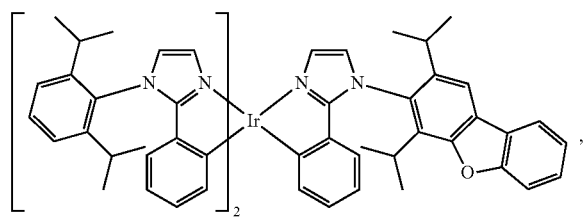
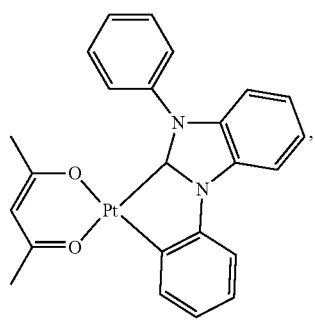
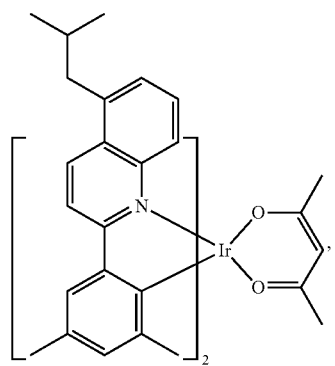
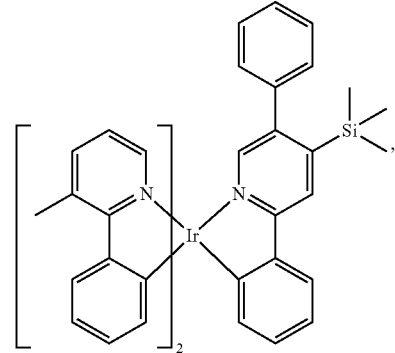
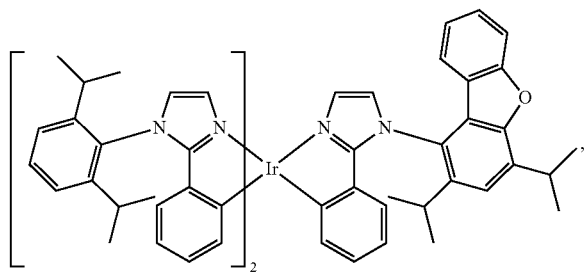
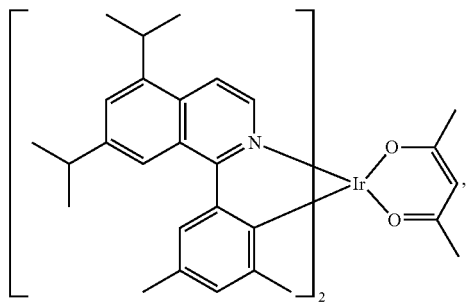

149
-continued
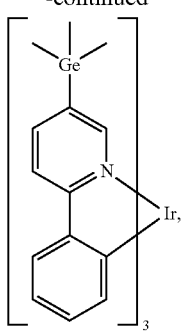
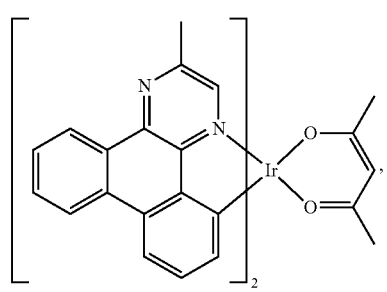
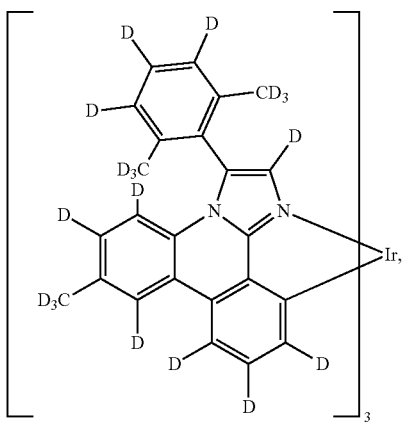
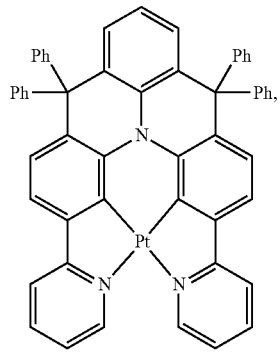
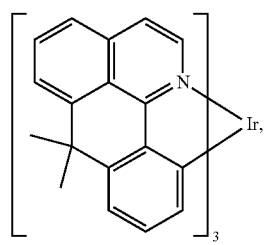
150
-continued
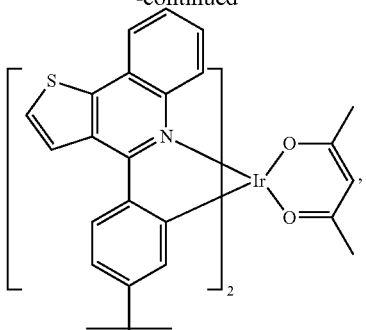
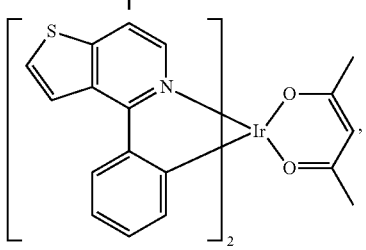
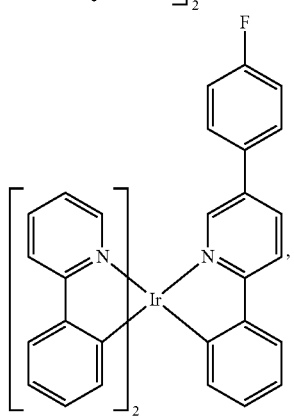
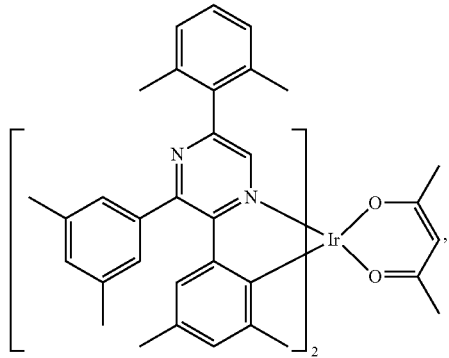
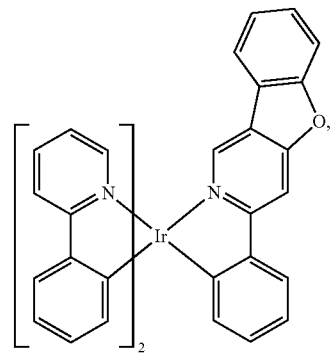

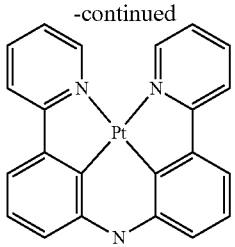
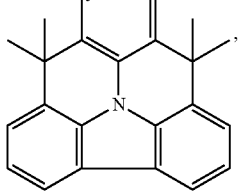
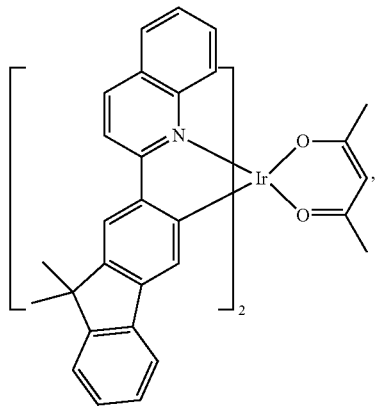
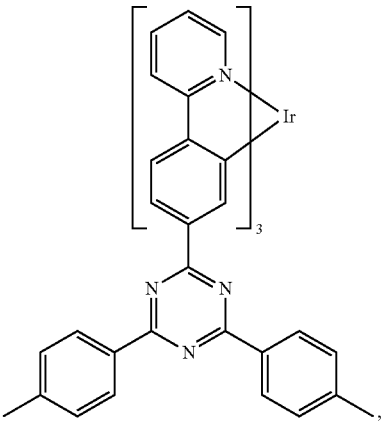
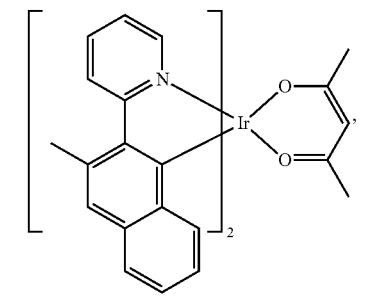
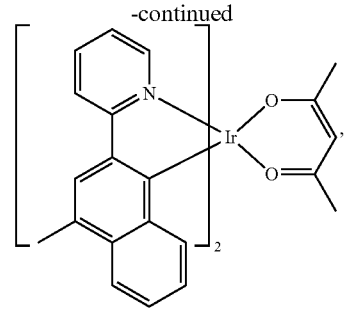
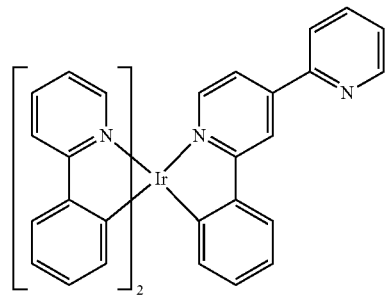
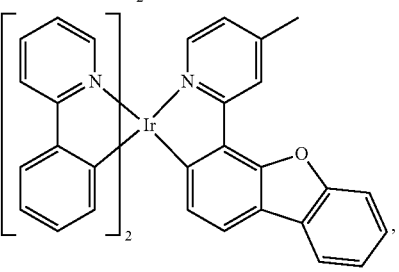
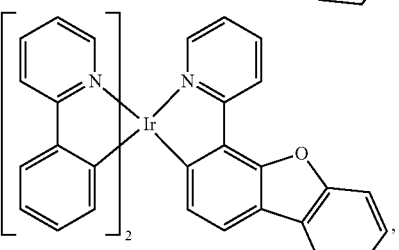
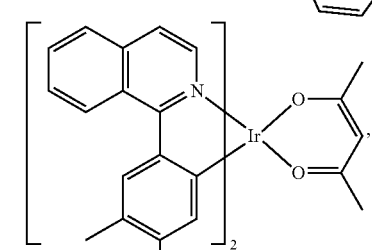
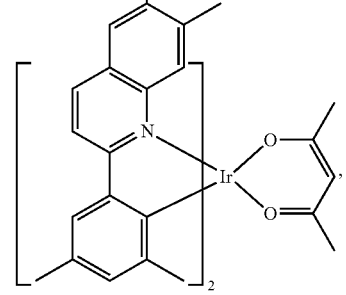

-continued
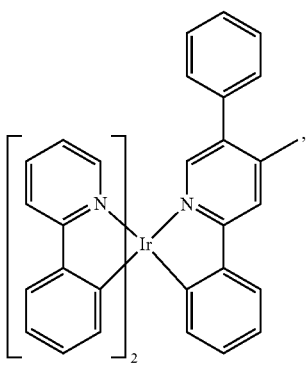
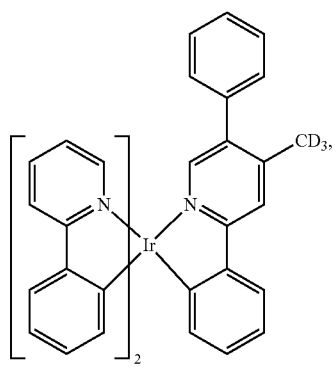
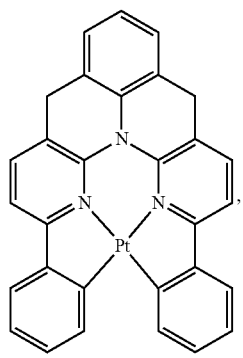
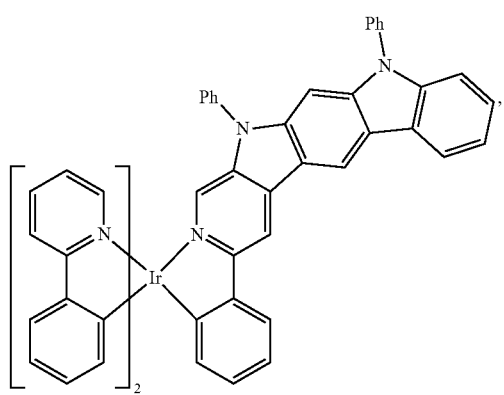
-continued
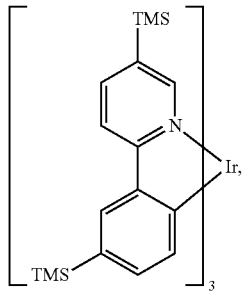
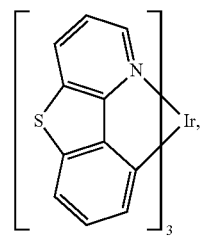
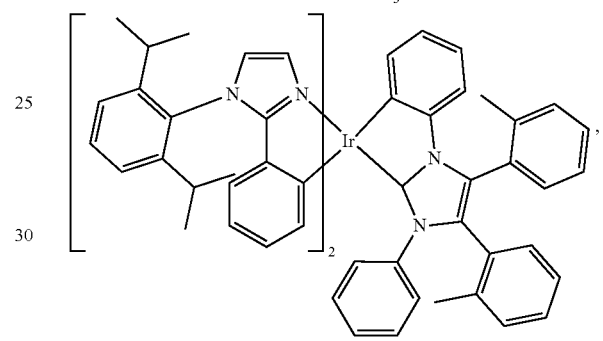
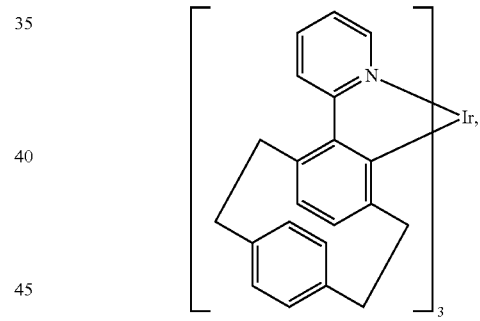
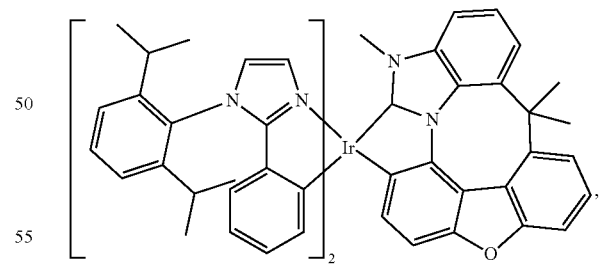
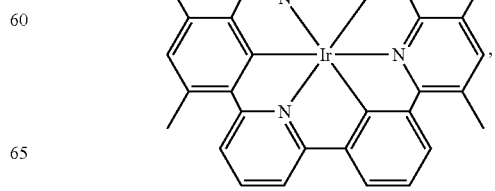

-continued
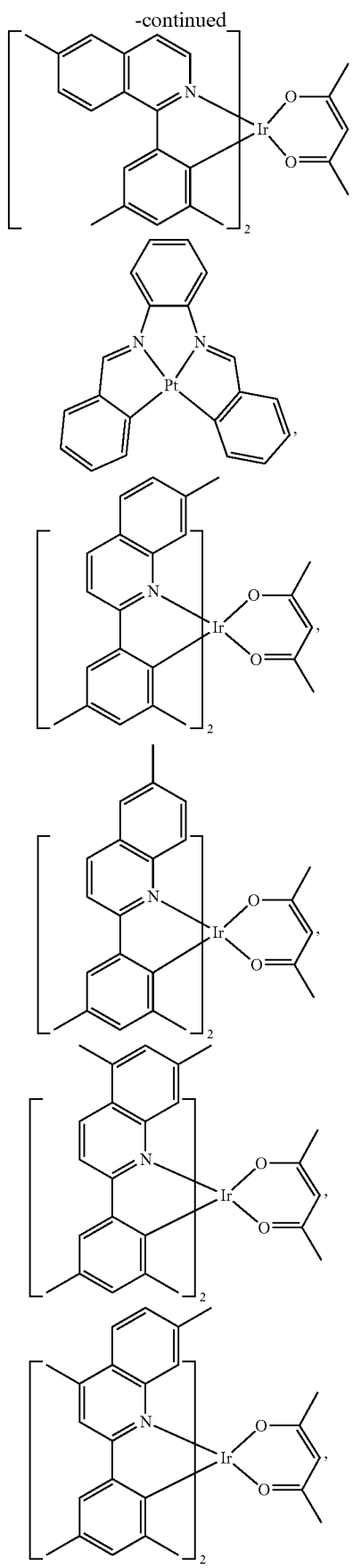
-continued
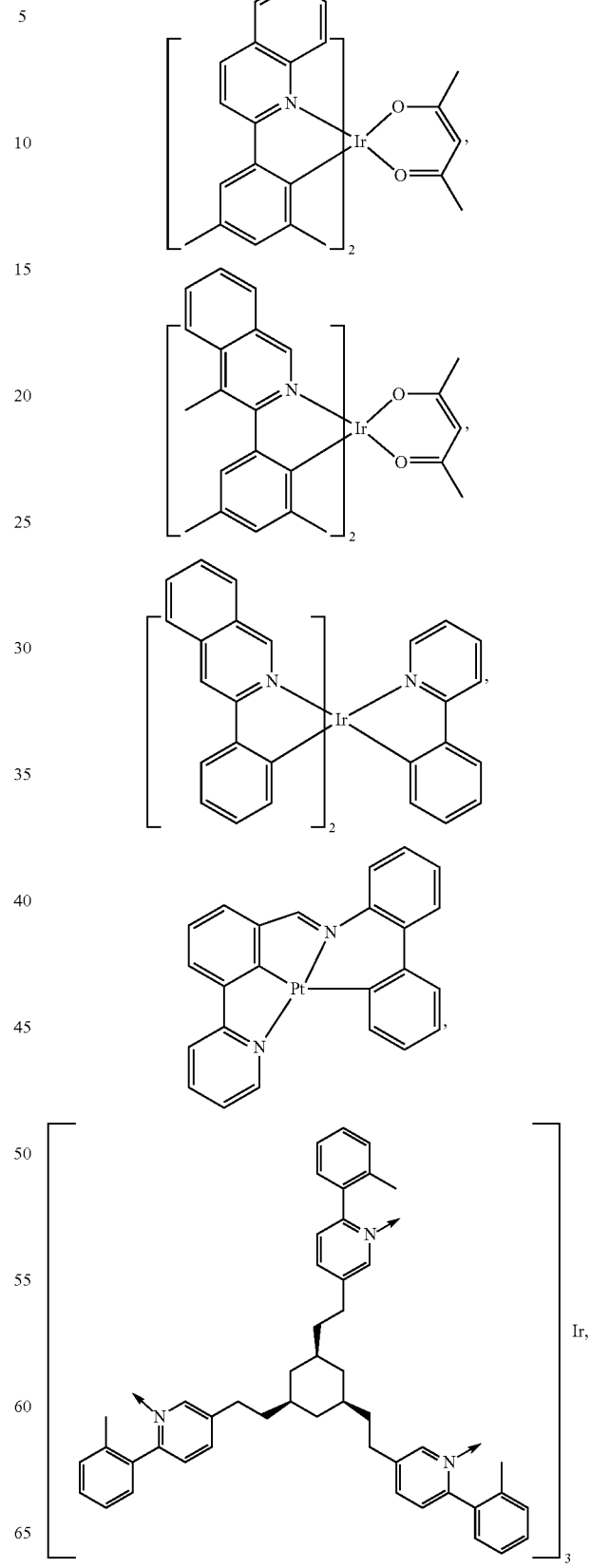

157
-continued
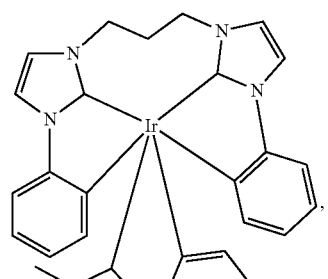
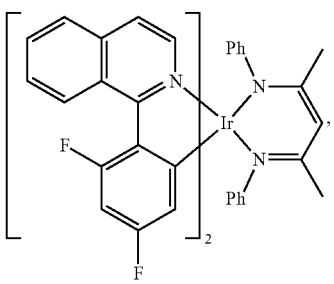
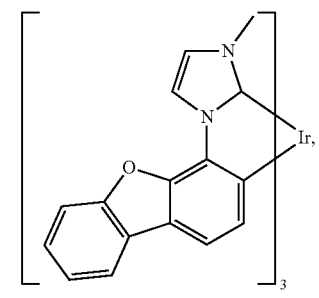
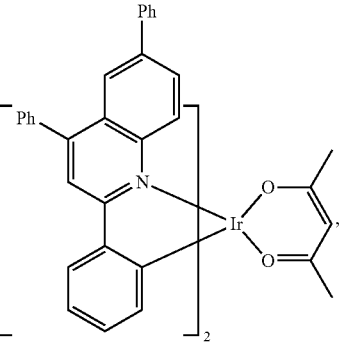
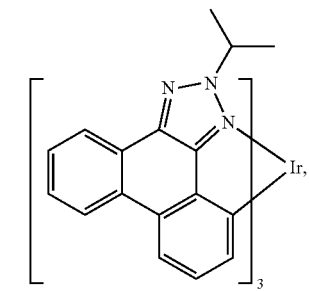
158
-continued
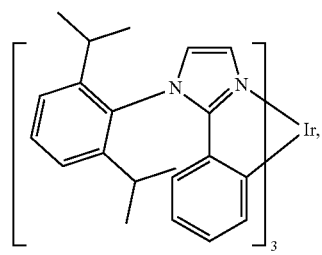
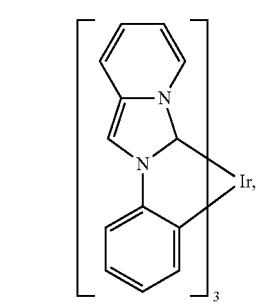
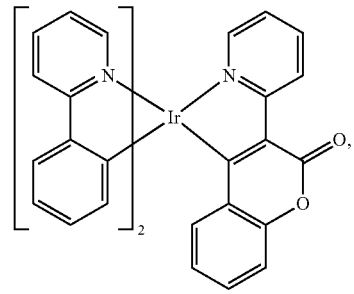
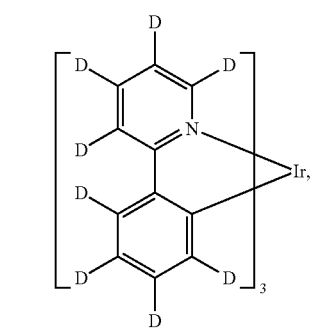
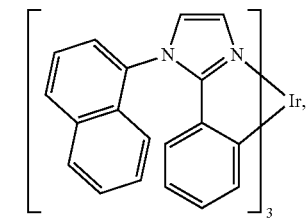
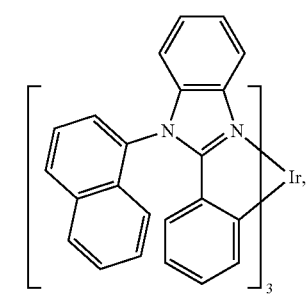

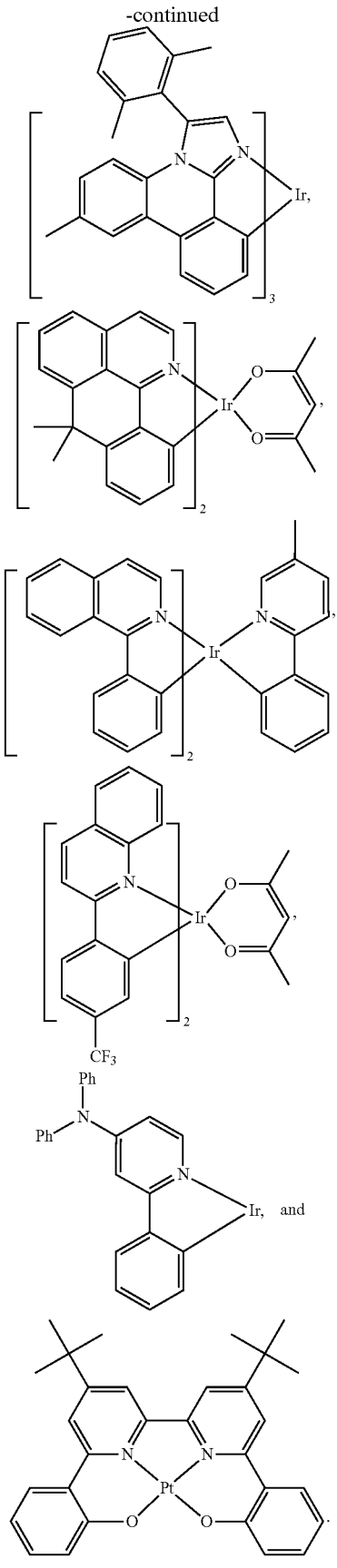

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and or higher triplet energy than the emitter closest to the HBL interface. In some embodiments, the HBL material has a lower HOMO (further from the vacuum level) and or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

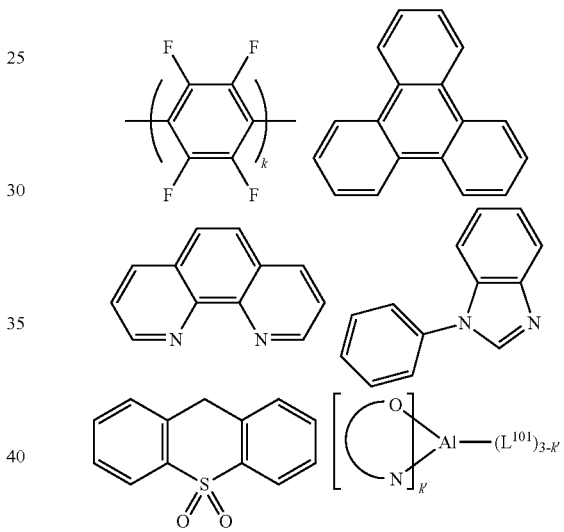

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

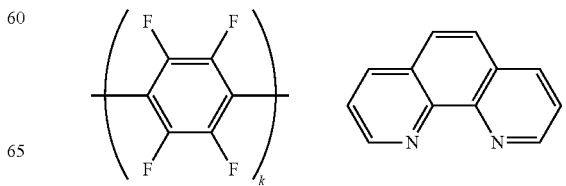

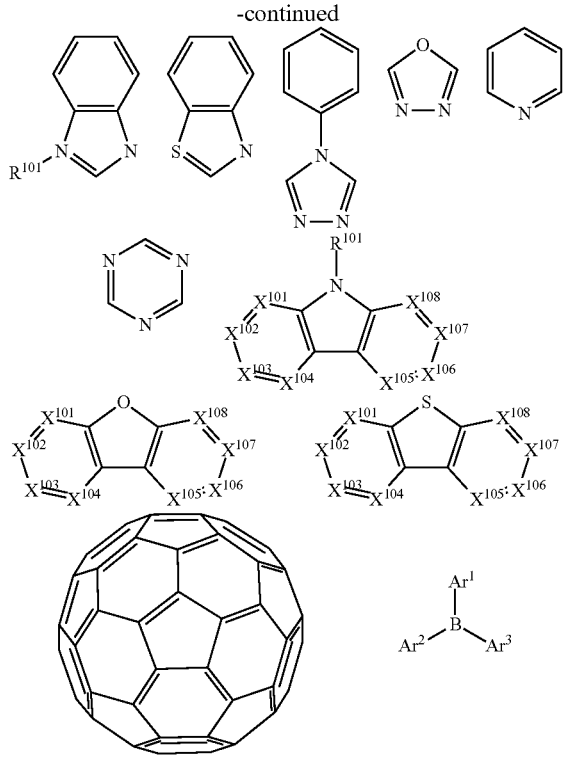

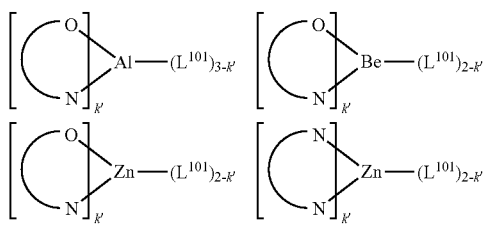

wherein R[101] is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. Ar[1] to Ar[3] has the similar definition as Ar's mentioned above. k is an integer from 1 to 20. X[101] to X[108] is selected from C (including CH) or N.

In another aspect, the metal complexes used in ETL include, but are not limited to the following general formula:

wherein (O—N) or (N—N) is a bidentate ligand, having metal coordinated to atoms O, N or N, N; L[101] is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

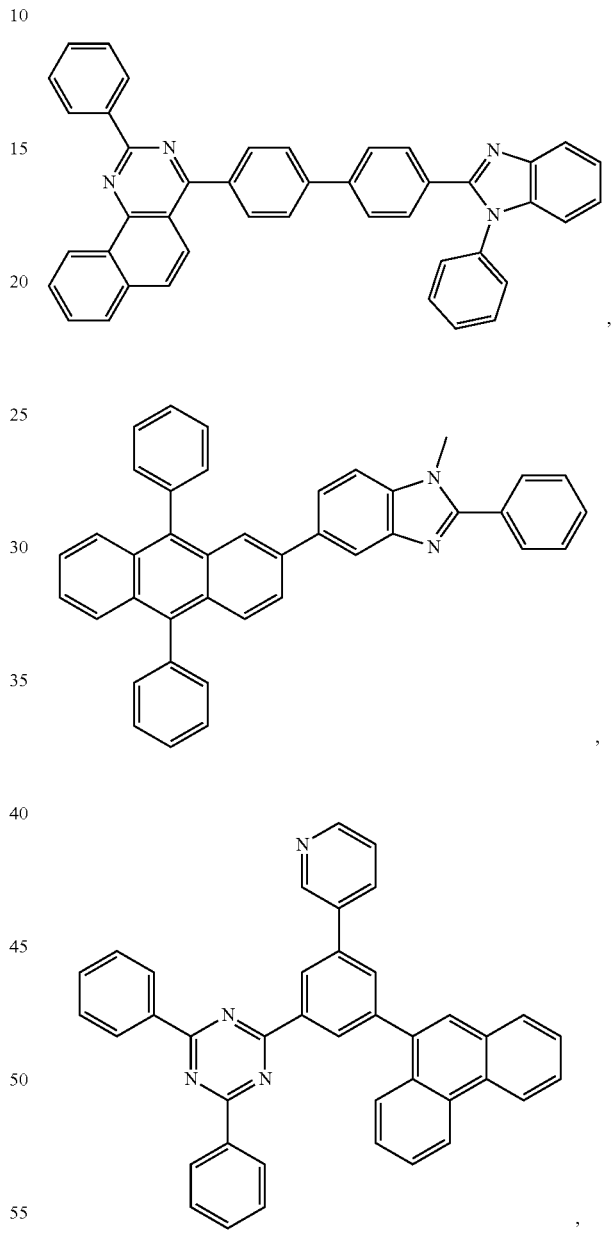

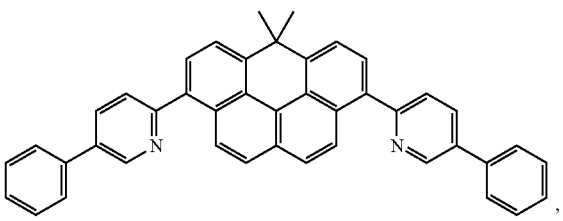

163
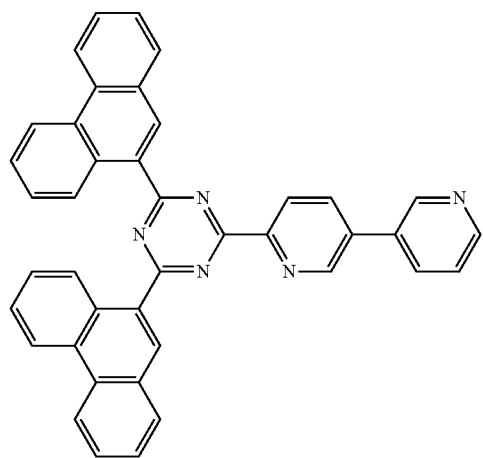
,
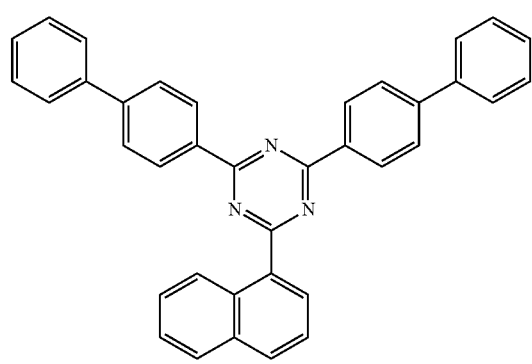
,
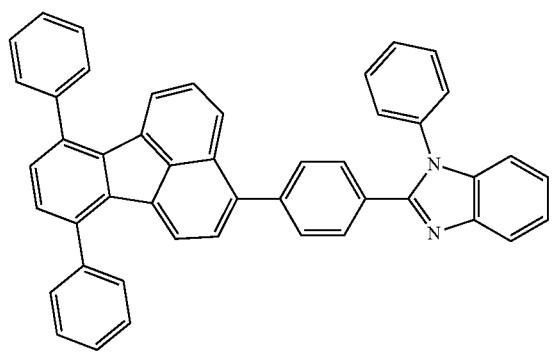
,
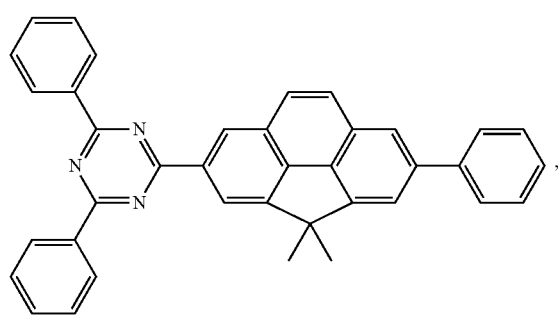
,
164
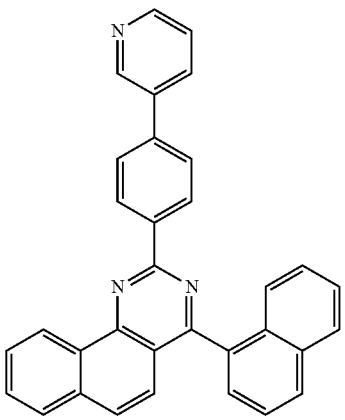
,
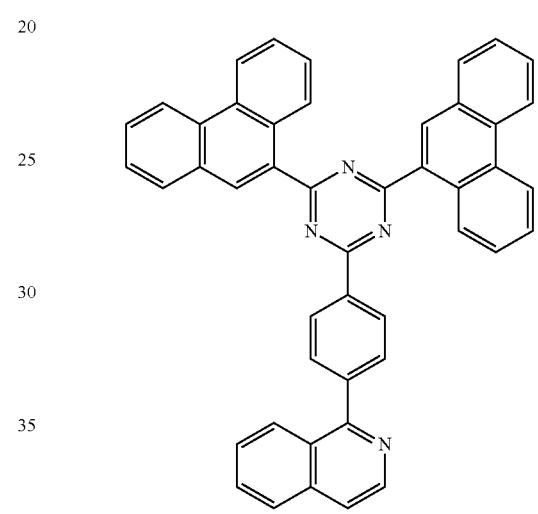
,
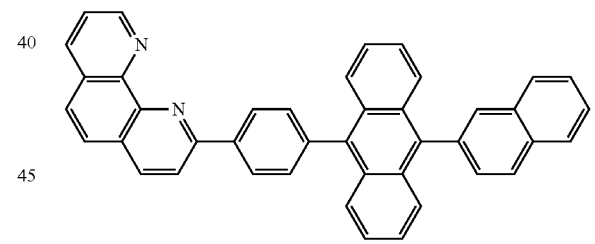
,
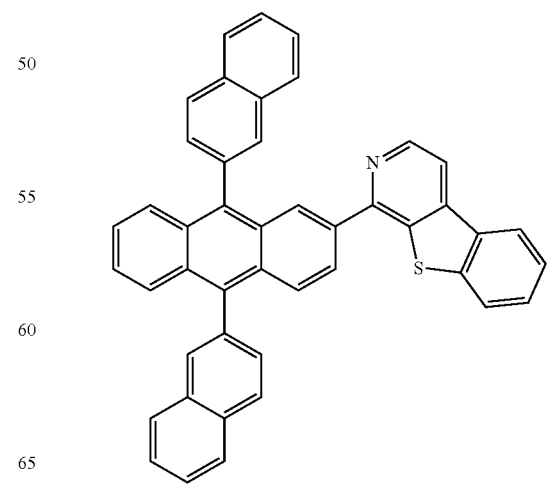
, 165
-continued
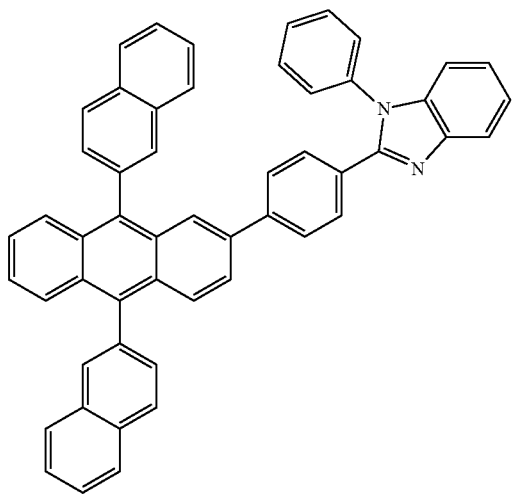
,
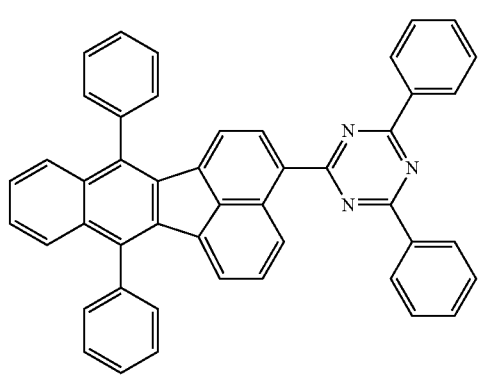
,
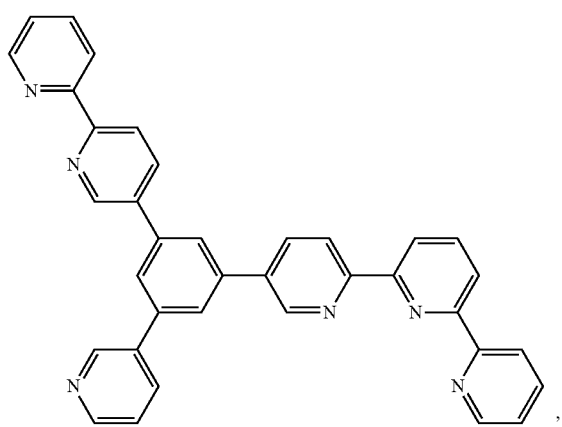
,
166
-continued
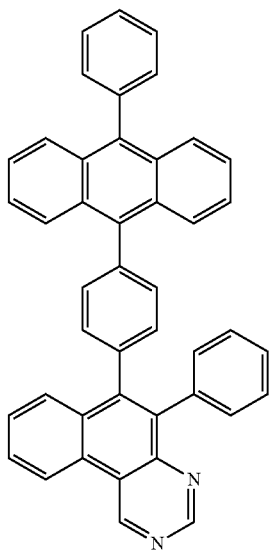
,
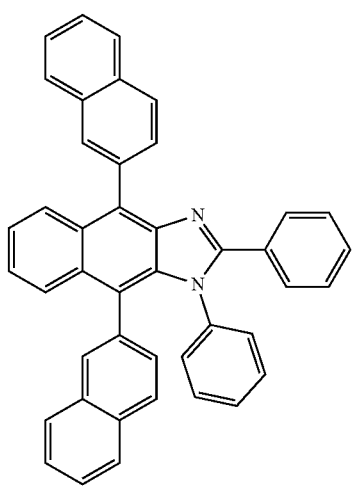
,
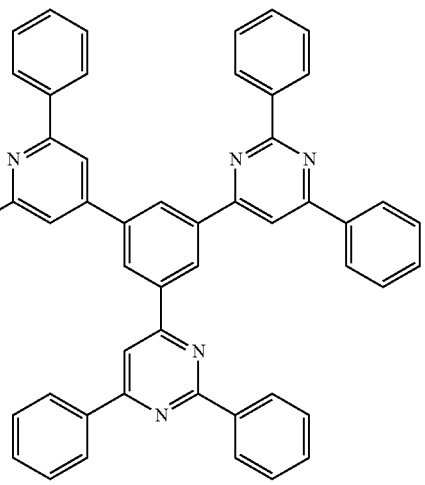
, 167
-continued
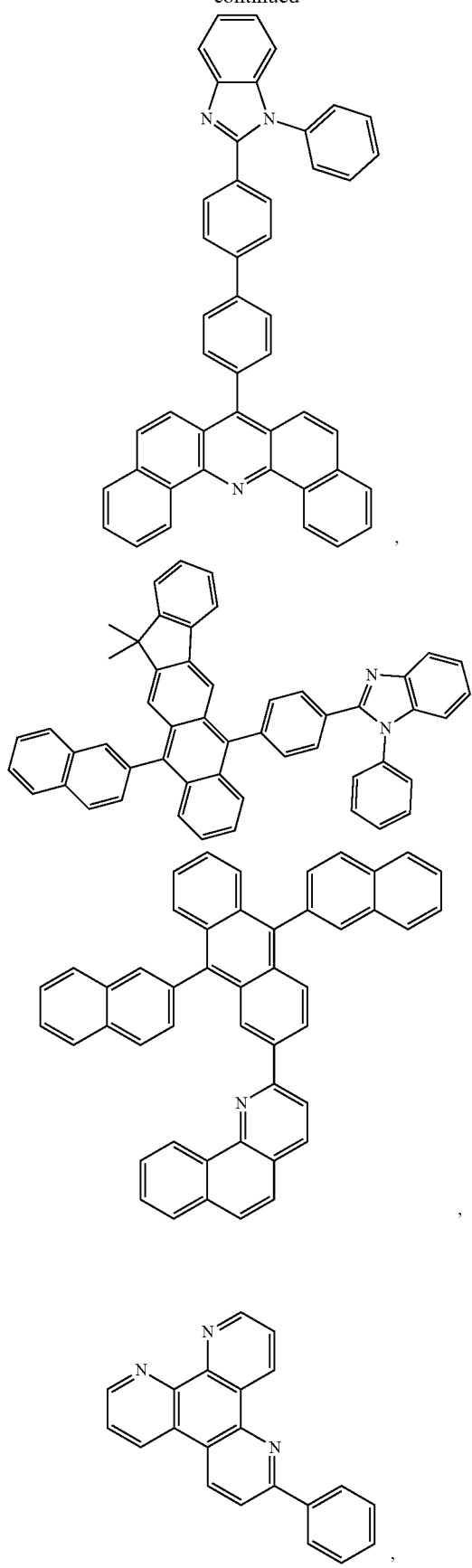
168
-continued
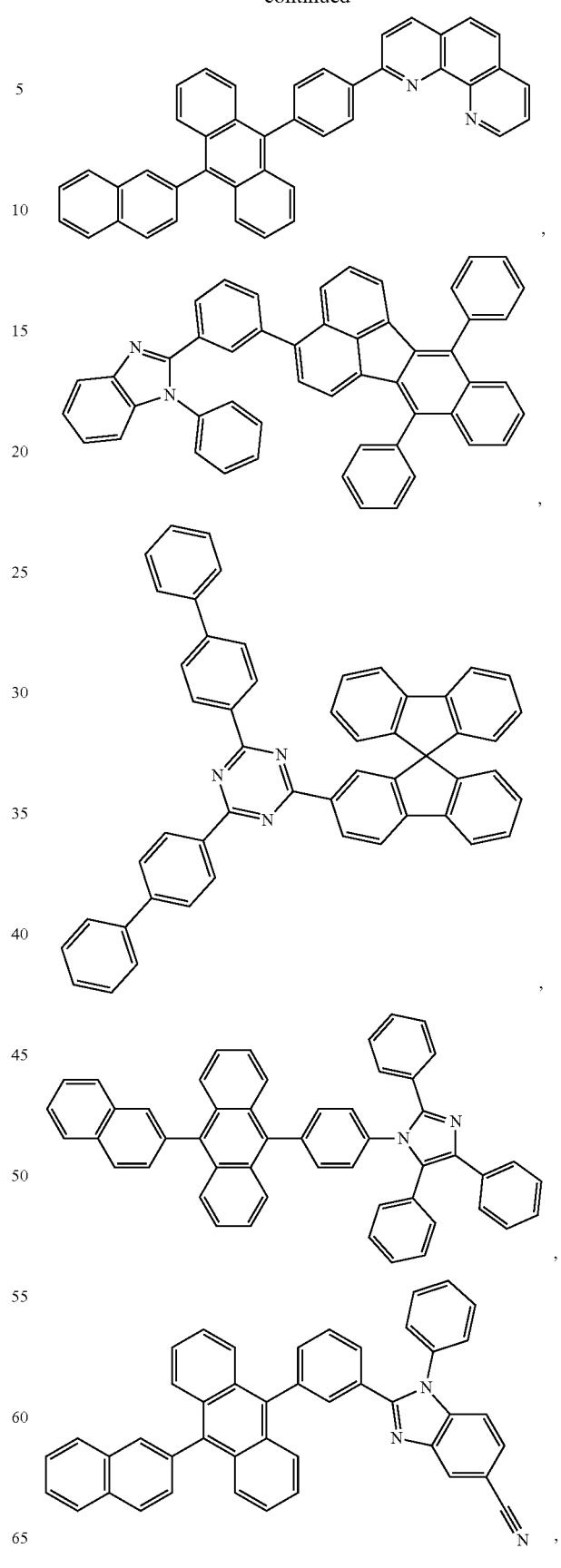

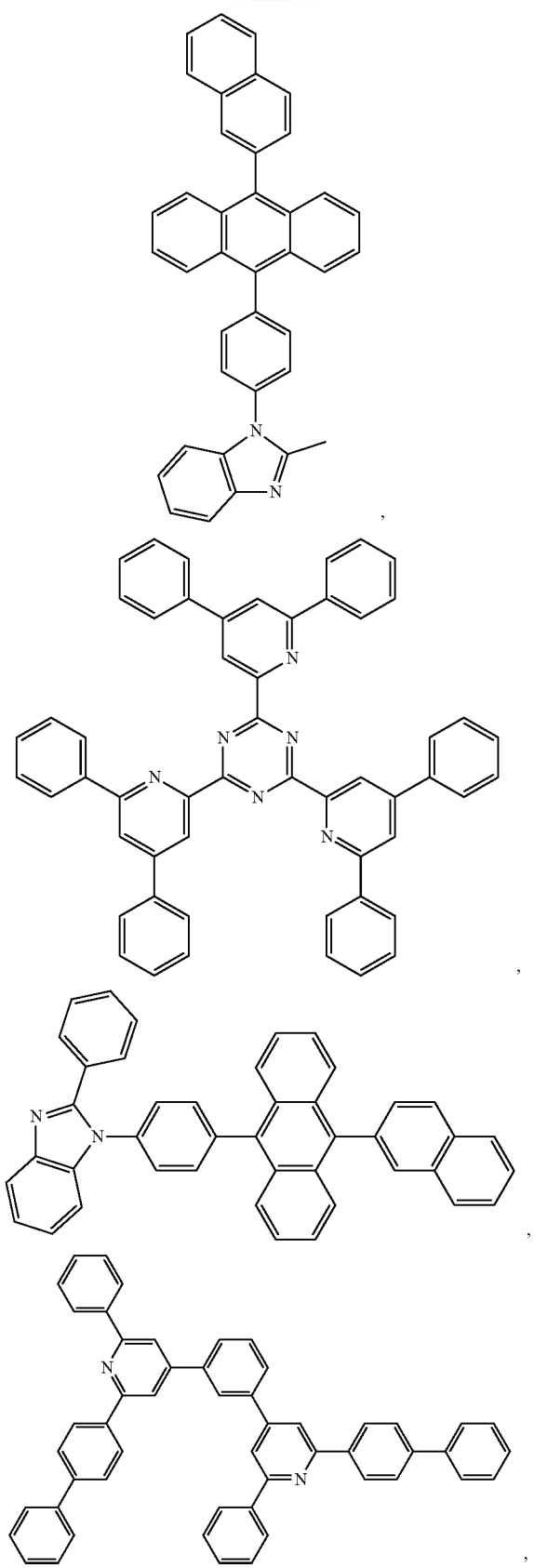

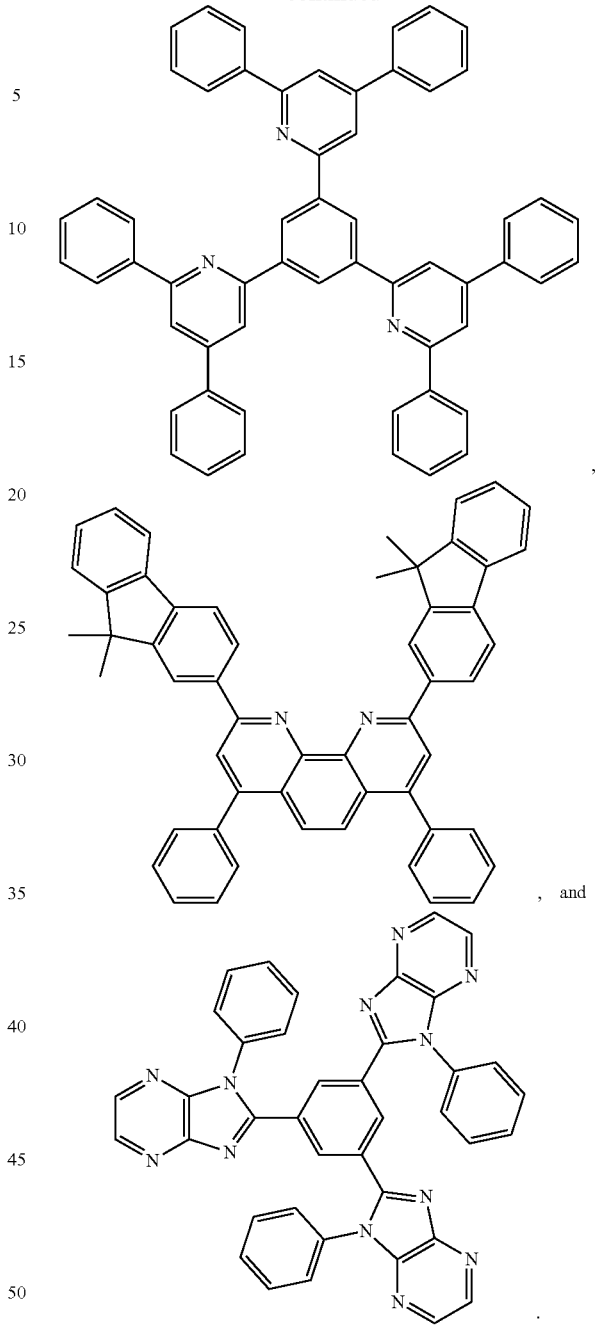

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

EXPERIMENTAL SECTION

Synthesis of Compound A

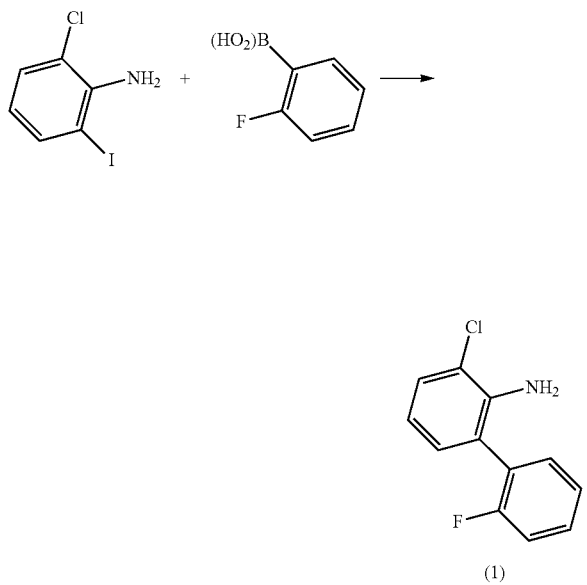

Compound A

Synthesis of 3-Chloro-2'-fluoro-[1,1'-biphenyl]-2-amine (1)

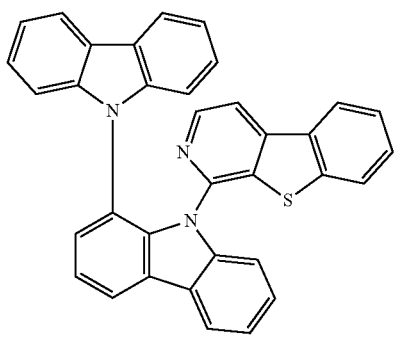

A $N_2$-purged flask containing 2-chloro-6-iodoaniline (10 g, 40 mmol), (2-fluorophenyl)boronic acid (7.0 g, 50 mmol), Pd(dppf)Cl$_2$·CH$_2$Cl$_2$ (1.5 g, 1.8 mmol) and potassium carbonate (10 g, 72 mmol) was charged with 4:1 (1,4-dioxane)/water (100 mL). The reaction mixture was stirred at for 90° C. for 2 h. The mixture was diluted with EtOAc (200 mL), filtered, washed with 1:1 water/brine (2×200 mL) and brine (100 mL), dried over MgSO$_4$, filtered and concentrated. Purification by flash column chromatography (330 g cart., silica gel, 50% DCM/isohexane liquid load, 0-50% DCM/isohexane gradient) provided 3-chloro-2'-fluoro-[1,1'-biphenyl]-2-amine (1) (8.1 g, 36 mmol, 91% yield) as a colourless oil.

Synthesis of N-(3-Chloro-2'-fluoro-[11'-biphenyl]-2-yl)benzo[4,5]thieno[2,3-c]pyridin-1-amine (2)

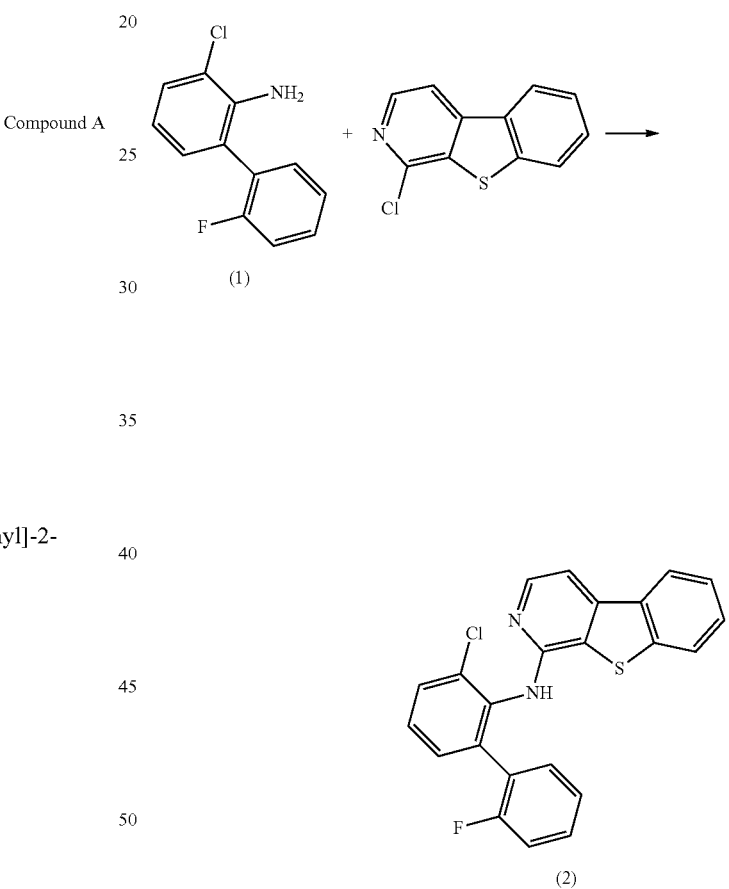

To a $N_2$-purged flask containing 1-chlorobenzo[4,5]thieno[2,3-c]pyridine (5.0 g, 23), xantphos (1.0 g, 1.7 mmol), palladium(II) acetate (0.25 g, 1.1 mmol), cesium carbonate (15 g, 46 mmol) and 3-chloro-2'-fluoro-[1,1'-biphenyl]-2-amine (1) (8.1 g, 37 mmol) was added 1,4-dioxane (100 mL). The reaction mixture was heated at 80° C. overnight. The reaction mixture was diluted with EtOAc (200 mL) and filtered through Celite. The filtrate was concentrated and purified by flash column chromatography (DCM load, silica gel, 330 g cart., 0-50% EtOAc/isohexane) to provide N-(3-chloro-2'-fluoro-[1,1'-biphenyl]-2-yl)benzo[4,5]thieno[2,3-c]pyridin-1-amine (2) (5.6 g, 14 mmol, 60% yield) as a white solid.

Synthesis of 1-(1-Chloro-9H-carbazol-9-yl)benzo[4,5]thieno[2,3-c]pyridine (3)

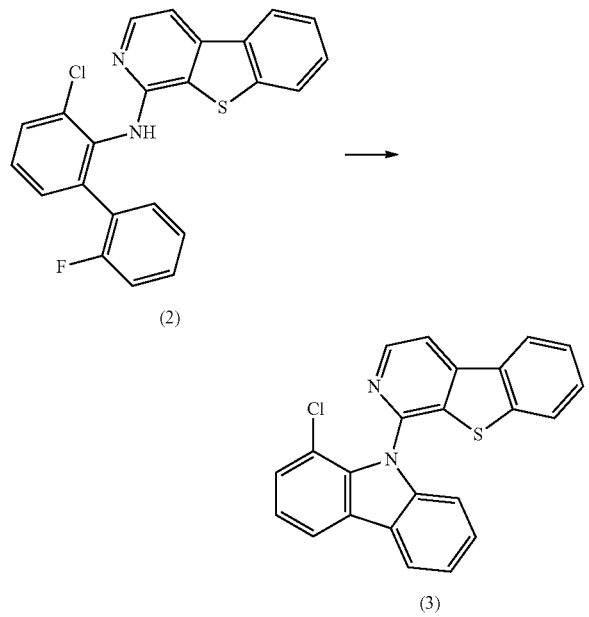

A N$_2$-purged flask containing N-(3-chloro-2'-fluoro-[1,1'-biphenyl]-2-yl)benzo[4,5]thieno[2,3-c]pyridin-1-amine (2) (5.6 g, 14 mmol) and potassium carbonate (8.0 g, 58 mmol) was charged with N-methyl-2-pyrrolidinone (50 mL). The reaction mixture was heated at 180° C. for 30 min. The reaction mixture was cooled to RT, diluted with EtOAc (200 mL), washed with 1:1 brine/water (2×200 mL) and brine (100 mL), dried over MgSO$_4$, filtered and concentrated. Purification by flash column chromatography (silica gel, 330 g cart., solid load, 0-50% MTBE/isohexane; mixed fractions were re-purified once using the same conditions) provided 1-(1-chloro-9H-carbazol-9-yl)benzo[4,5]thieno[2,3-c]pyridine (3) (3.76 g, 9.57 mmol, 69% yield) as a white solid.

Synthesis of 2'-Fluoro-[1,1'-biphenyl]-2-amine (4)

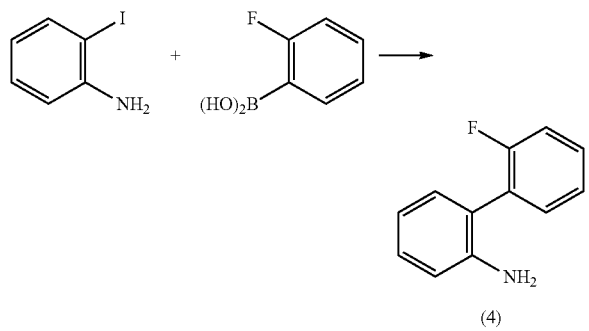

A N$_2$-purged flask containing 2-iodoaniline (6.0 g, 27 mmol), (2-fluorophenyl)boronic acid (5.0 g, 36 mmol), Pd(dppf)Cl$_2$·CH$_2$Cl$_2$ (1.0 g, 1.2 mmol) and potassium carbonate (7.0 g, 51 mmol) was charged with 4:1 (1,4-dioxane)/water (50 mL). The reaction mixture was stirred at for 90° C. for 2 h. The mixture was diluted with EtOAc (200 mL), filtered, washed with 1:1 water/brine (2×200 mL) and brine (100 mL), dried over MgSO$_4$, filtered and concentrated. Purification by flash column chromatography (330 g cart., silica gel, solid load, 50-100% DCM/isohexane) followed by trituration with 20% TBME/isohexane (25 mL) provided 2'-fluoro-[1,1'-biphenyl]-2-amine (4) (3.51 g, 18.0 mmol, 66% yield) as a tan solid.

Synthesis of 9-(Benzo[4,5]thieno[2,3-c]pyridin-1-yl)-N-(2'-fluoro-[1,1'-biphenyl]-2-yl)-9H-carbazol-1-amine (5)

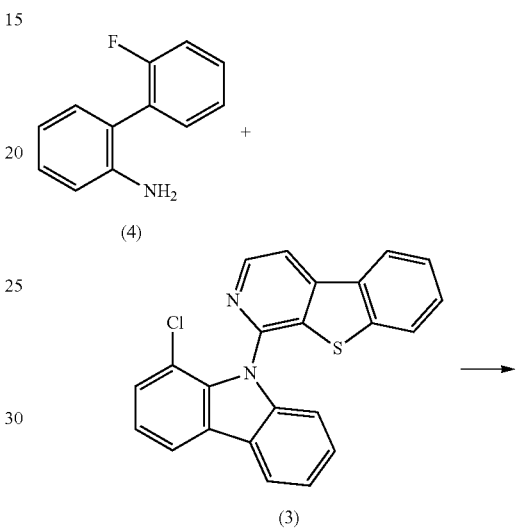

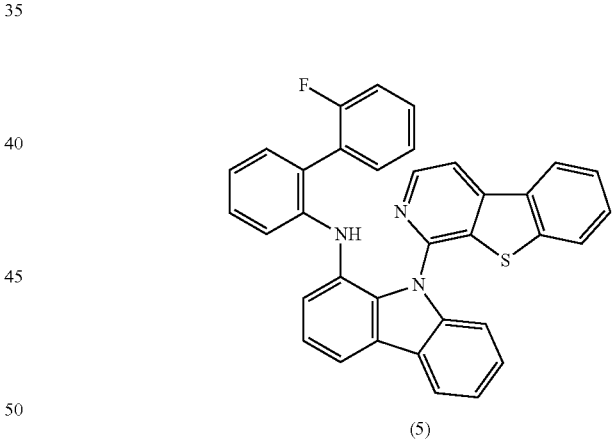

A N$_2$-purged flask containing tri-tert-butylphosphonium tetrafluoroborate (1.0 g, 3.5 mmol), palladium(II) acetate (0.25 g, 1.1 mmol), sodium tert-butoxide (2.8 g, 29 mmol), 2'-fluoro-[1,1'-biphenyl]-2-amine (4) (3.7 g, 20 mmol) and 1-(1-chloro-9H-carbazol-9-yl)benzo[4,5]thieno[2,3-c]pyridine (3) (3.75 g, 9.74 mmol) was charged with o-xylene (40 mL). The reaction mixture was stirred at 140° C. for 3 h. The reaction mixture was cooled to RT, diluted with EtOAc (150 mL), filtered through Celite and concentrated. The crude was purified by flash column chromatography (silica gel (RediSep Gold), 330 g cart., solid load, 0-40% EtOAc/isohexane) to provide 9-(benzo[4,5]thieno[2,3-c]pyridin-1-yl)-N-(2'-fluoro-[1,1'-biphenyl]-2-yl)-9H-carbazol-1-amine (5) (4.67 g, 8.46 mmol, 87% yield) as a yellow foam.

Synthesis of 1-(9H-[1,9'-Bicarbazol]-9-yl)benzo[4,5]thieno[2,3-c]pyridine (Compound A)

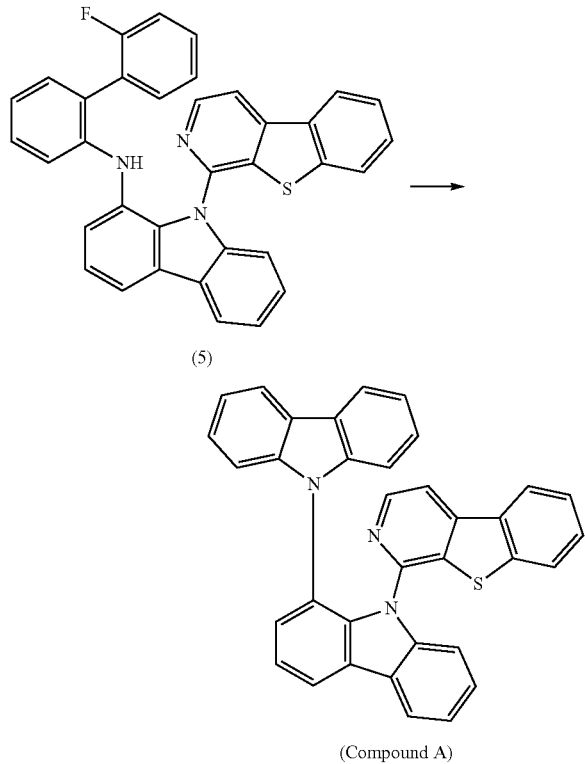

(5)

(Compound A)

A N₂-purged flask containing 9-(benzo[4,5]thieno[2,3-c]pyridin-1-yl)-N-(2'-fluoro-[1,1'-biphenyl]-2-yl)-9H-carbazol-1-amine (5) (4.66 g, 8.70 mmol) and cesium carbonate (15 g, 46 mmol) was charged with N-methyl-2-pyrrolidinone (50 mL). The reaction mixture was heated at 180° C. for 3 h. The reaction mixture was cooled to RT, diluted with EtOAc (200 mL), washed with 1:1 brine/water (2×200 mL) and brine (100 mL), dried over MgSO₄, filtered and concentrated. Purification by flash column chromatography (silica gel, 330 g cart., solid load, 0-100% DCM/isohexane) gave the product as a white solid. The solid was suspended in 5:30 EtOAc/isohexane (35 mL) and stirred at RT overnight. The solid was collected by filtration and rinsed with 10% EtOAc/isohexane (10 mL) to provide 1-(9H-[1,9'-bicarbazol]-9-yl)benzo[4,5]thieno[2,3-c]pyridine (Compound A) (3.4 g, 6.6 mmol, 76% yield) as a white solid.

Compound 1

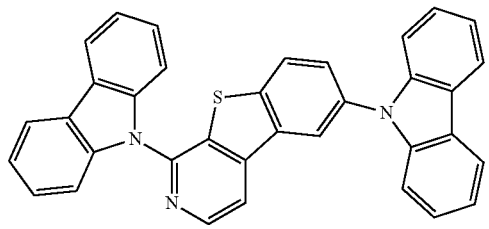

Emitter 1

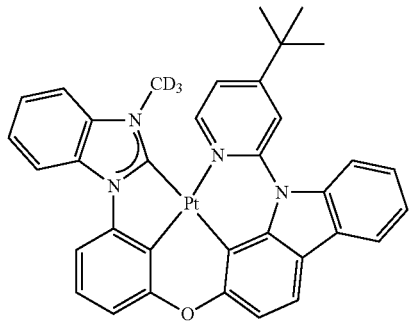

Vacuum deposited thin films were fabricated using Compound 1 and Compound A as single hosts for a blue emitter (Emitter 1). It was found that the PLQY of the thin film using Compound A increased compared to Compound 1 (see Table 1).

TABLE 1

| Host | λ max [nm] | FWHM [nm] | PLQY [%] |
|---|---|---|---|
| Compound A | 456 | 23 | 54% |
| Compound 1 | 459 | 26 | 43% |

The thin films in Table 1 were fabricated in high vacuum (<10⁻⁶ Torr) by thermal evaporation onto a quartz substrate. The films were a 300 Å organic layer composed of the Host doped with 5% by volume of Emitter 1.

We claim:
1. A compound of Formula II:

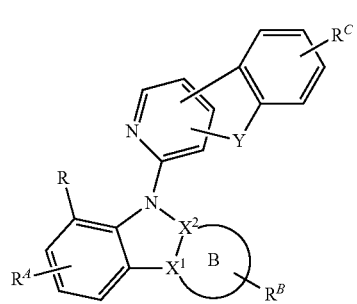

Formula II wherein
ring B is a 5-membered heterocyclic ring or a 6-membered carbocyclic ring;
$X^1$ and $X^2$ are independently $CR^X$ or N, and at least one of $X^1$ or $X^2$ is $CR^X$;
Y is selected from the group consisting of O, S, Se, NR', BR', CR'R", and SiR'R";
R', and R" are each independently selected from the group consisting of alkyl, cycloalkyl, heteroalkyl, heterocycloalkyl, aryl, heteroaryl, and combinations thereof;
R is a substituted or unsubstituted aryl or heteroaryl;
$R^A$, $R^B$, and $R^C$ each independently represent mono to the maximum allowable substitution, or no substitution; and
each $R^X$, $R^A$, $R^B$, and $R^C$ is independently a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof, and wherein any two substituents $R^X$, $R^A$, $R^B$, and $R^C$ may be optionally joined to form a ring, with the proviso that R does not join with $R^A$ to form a ring.

2. The compound of claim 1, wherein each $R^X$, $R^A$, $R^B$, and $R^C$ is independently a hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

3. The compound of claim 1, wherein R comprises a chemical group selected from the group consisting of carbazole, aza-carbazole, dibenzofuran, aza-dibenzofuran, dibenzothiophene, aza-dibenzothiophene, benzene, pyrimidine, and triazine.

4. The compound of claim 1, wherein Y is O or S.

5. The compound of claim 1, wherein $X^1$ is N and $X^2$ is $CR^X$.

6. The compound of claim 1, wherein $X^1$ and $X^2$ are both $CR^X$.

7. The compound of claim 1, wherein ring B is a 5-membered heteroaromatic ring.

8. The compound of claim 1, wherein ring B is a 6-membered carbocyclic ring.

9. The compound of claim 1, wherein two adjacent $R^B$ substituents join to form a 5-membered or 6-membered aromatic ring that is fused to ring B.

10. The compound of claim 1, wherein the compound is selected from the group consisting of

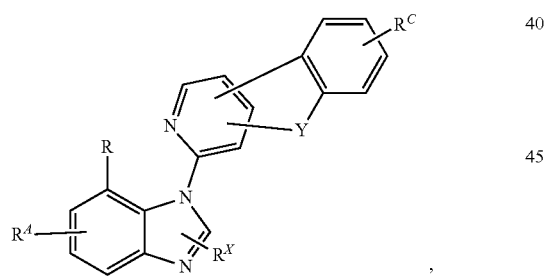

,

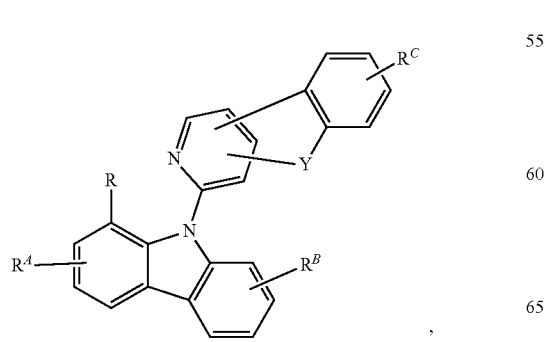

,

-continued

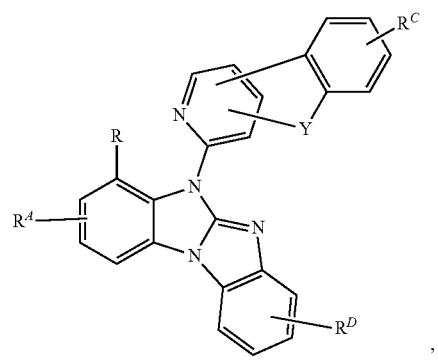

,

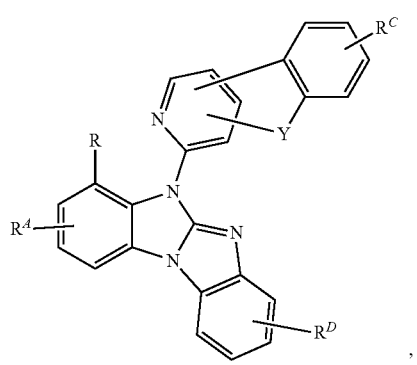

,

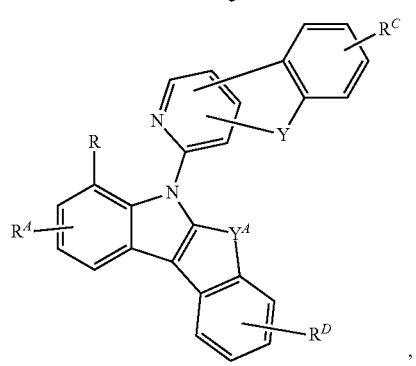

,

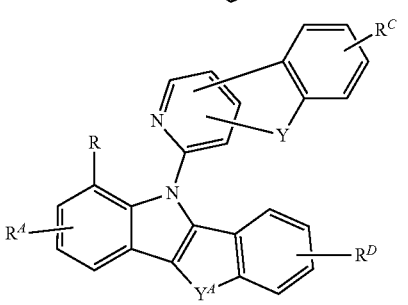

,

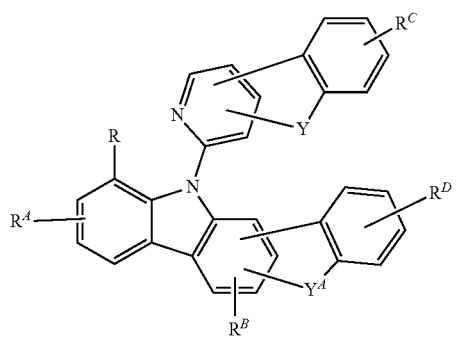

,

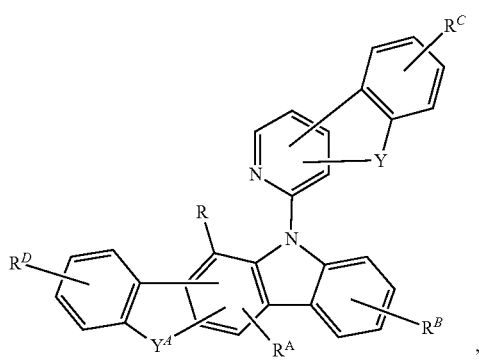
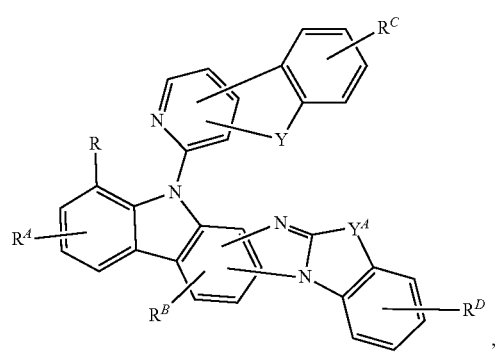
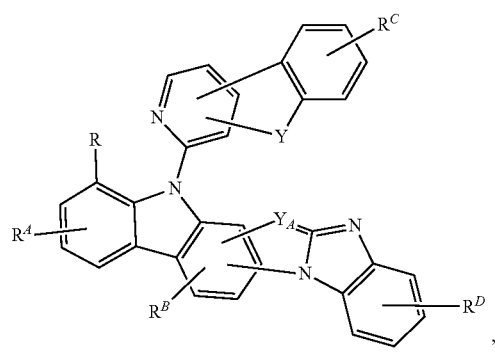
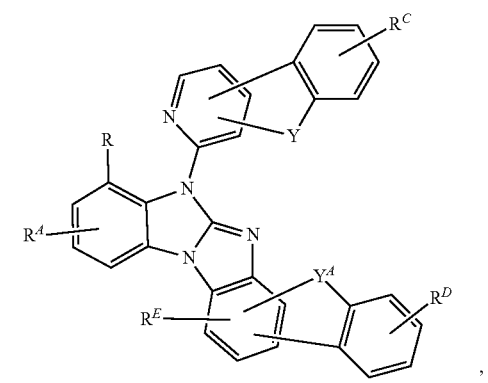
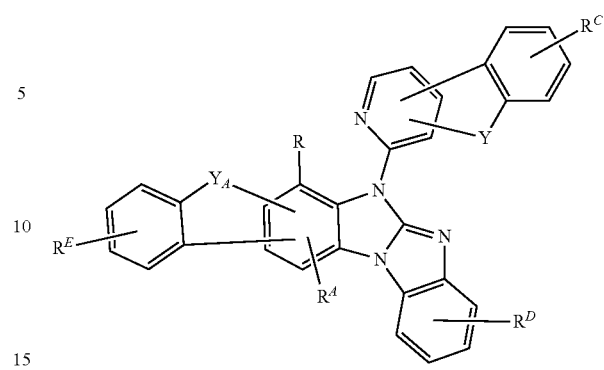
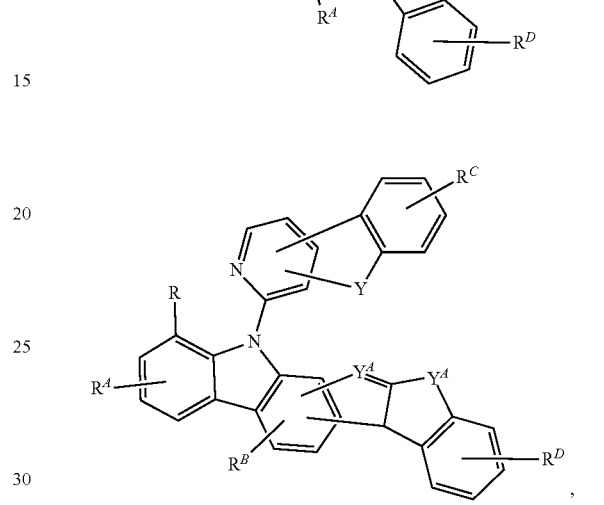
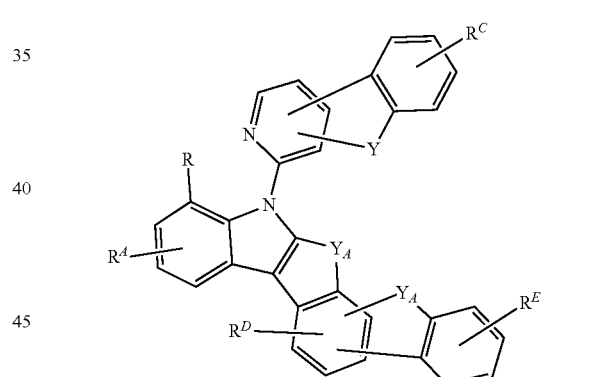
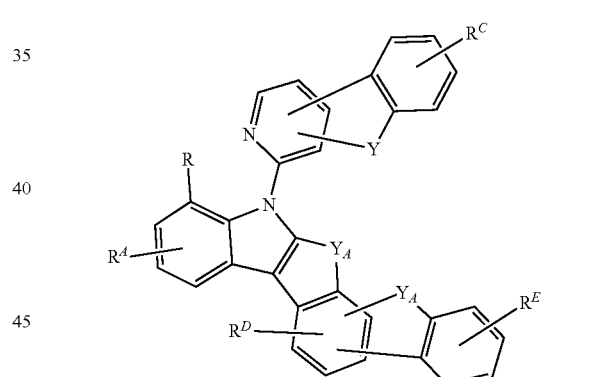

-continued

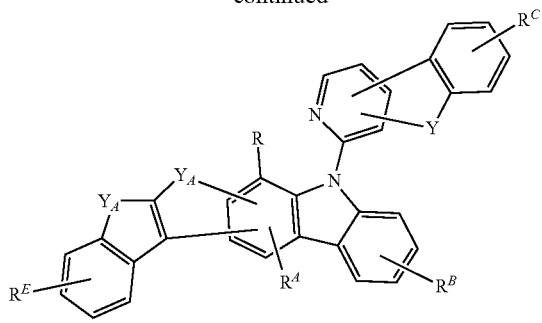

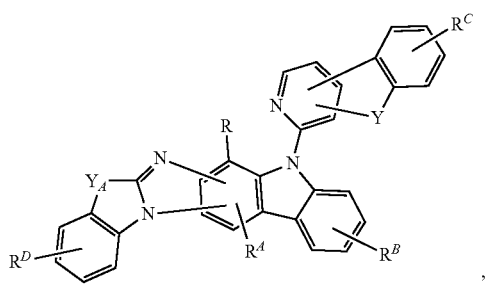

, and

-continued

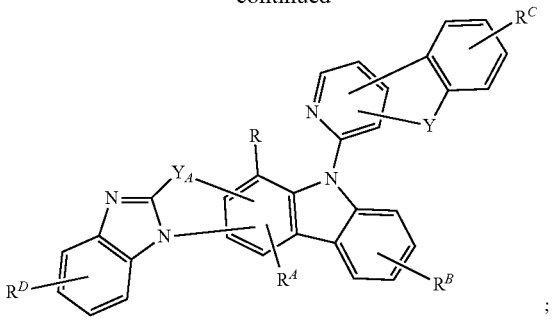

;

wherein
each $Y_A$ is selected from the group consisting of O, S, Se, NR', CR'R", and SiR'R";
$R^D$ and $R^E$ independently represent mono to the maximum allowable substitution, or no substitution; and
each $R^D$ and $R^E$ is independently a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof, and any two substituents $R^D$ or $R^E$ may be optionally joined to form a ring.

11. The compound of claim 1, wherein the compound is Compound X selected from the group consisting of

| Structure | $R_1$, $R_2$, Ar | x equal to | Compound x |
|---|---|---|---|
| 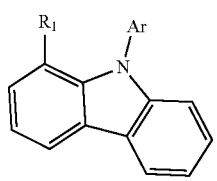 | Ar = Ai<br>$R_1$ = Rj<br>i and j are each independently an integer from 1 to 50 | 50(i − 1) + j + 2500 | Compound 2501-5000 |
| 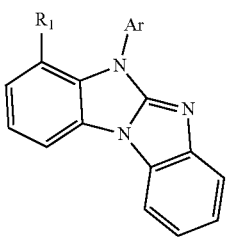 | Ar = Ai<br>$R_1$ = Rj<br>i and j are each independently an integer from 1 to 50 | 50(i − 1) + j + 5000 | Compound 5001-7500 |
| 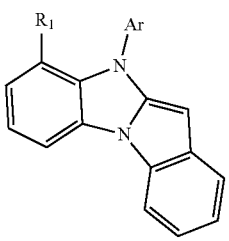 | Ar = Ai<br>$R_1$ = Rj<br>i and j are each independently an integer from 1 to 50 | 50(i − 1) + j + 7500 | Compound 7501-10000 |

-continued

| Structure | R₁, R₂, Ar | x equal to | Compound x |
|---|---|---|---|
| (structure) | Ar = Ai<br>R₁ = Rj<br>i and j are each independently an integer from 1 to 50 | 50(i − 1) + j + 10000 | Compound 10001-12500 |
| (structure) | Ar = Ai<br>R₁ = Rj<br>i and j are each independently an integer from 1 to 50 | 50(i − 1) + j + 12500 | Compound 12501-15000 |
| (structure) | Ar = Ai<br>R₁ = Rj<br>i and j are each independently an integer from 1 to 50 | 50(i − 1) + j + 15000 | Compound 15001-17500 |
| (structure) | Ar = Ai<br>R₁ = Rj<br>i and j are each independently an integer from 1 to 50 | 50(i − 1) + j + 17500 | Compound 17501-20000 |
| (structure) | Ar = Ai<br>R₁ = Rj<br>i and j are each independently an integer from 1 to 50 | 50(i − 1) + j + 20000 | Compound 20001-22500 |
| (structure) | Ar = Ai<br>R₁ = Rj<br>i and j are each independently an integer from 1 to 50 | 50(i − 1) + j + 22500 | Compound 22501-25000 |

-continued

| Structure | R₁, R₂, Ar | x equal to | Compound x |
|---|---|---|---|
| | Ar = Ai<br>R₁ = Rj<br>i and j are each independently an integer from 1 to 50 | 50(i − 1) + j + 25000 | Compound 25001-27500 |
| | Ar = Ai<br>R₁ = Rj<br>i and j are each independently an integer from 1 to 50 | 50(i − 1) + j + 27500 | Compound 27501-30000 |
| | Ar = Ai<br>R₁ = Rj<br>i and j are each independently an integer from 1 to 50 | 50(i − 1) + j + 30000 | Compound 30001-32500 |
| | Ar = Ai<br>R₁ = Rj<br>i and j are each independently an integer from 1 to 50 | 50(i − 1) + j + 32500 | Compound 32501-35000 |
| | Ar = Ai<br>R₁ = Rj<br>i and j are each independently an integer from 1 to 50 | 50(i − 1) + j + 35000 | Compound 35001-37500 |
| | Ar = Ai<br>R₁ = Rj<br>i and j are each independently an integer from 1 to 50 | 50(i − 1) + j + 37500 | Compound 37501-40000 |
| | Ar = Ai<br>R₁ = Rj<br>i and j are each independently an integer from 1 to 50 | 50(i − 1) + j + 40000 | Compound 40001-42500 |

-continued

| Structure | R₁, R₂, Ar | x equal to | Compound x |
|---|---|---|---|
| | Ar = Ai<br>R₁ = Rj<br>i and j are each independently an integer from 1 to 50 | 50(i − 1) + j + 42500 | Compound 42501-45000 |
| | Ar = Ai<br>R₁ = Rj<br>i and j are each independently an integer from 1 to 50 | 50(i − 1) + j + 45000 | Compound 45001-47500 |
| | Ar = Ai<br>R₁ = Rj<br>i and j are each independently an integer from 1 to 50 | 50(i − 1) + j + 47500 | Compound 47501-50000 |
| | Ar = Ai<br>R₁ = Rj<br>R₂ = Rk<br>i, j, and k are each independently an integer from 1 to 50 | 2500(i − 1) + 50(j − 1) + k + 50000 | Compound 50001-175000 |
| | Ar = Ai<br>R₁ = Rj<br>R₂ = Rk<br>i, j, and k are each independently an integer from 1 to 50 | 2500(i − 1) + 50(j − 1) + k + 175000 | Compound 175001-300000 |
| | Ar = Ai<br>R₁ = Rj<br>R₂ = Rk<br>i, j, and k are each independently an integer from 1 to 50 | 2500(i − 1) + 50(j − 1) + k + 300000 | Compound 300001-425000 |

| Structure | R₁, R₂, Ar | x equal to | Compound x |
|---|---|---|---|
| (structure) | Ar = Ai<br>R₁ = Rj<br>R₂ = Rk<br>i, j, and k are each independently an integer from 1 to 50 | 2500(i − 1) +<br>50(j − 1) +<br>k + 425000 | Compound 425001-550000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 550000 | Compound 550001-675000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 675000 | Compound 675001-800000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 800000 | Compound 800001-925000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 925000 | Compound 925001-1050000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 1175000 | Compound 1175001-1300000 |

-continued

| Structure | R₁, R₂, Ar | x equal to | Compound x |
|---|---|---|---|
| (structure) | Ar = Ai<br>R₁ = Rj<br>R₂ = Rk<br>i, j, and k are each independently an integer from 1 to 50 | 2500(i − 1) +<br>50(j − 1) +<br>k + 1300000 | Compound 1300001-1425000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 1425000 | Compound 1425001-1550000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 1550000 | Compound 1550001-1675000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 1675000 | Compound 1675001-1800000 |
| (structure) | Ar = Ai<br>R₁ = Rj<br>R₂ = Rk<br>R₃ = Rm<br>i, j, k and m are each independently an integer from 1 to 50 | 125000(i − 1) +<br>2500(j − 1) +<br>50(k − 1) +<br>m + 1800000 | Compound 1800001-8050000 |
| (structure) | Ar = Ai<br>R₁ = Rj<br>R₂ = Rk<br>R₃ = Rm<br>i, j, k and m are each independently an integer from 1 to 50 | 125000(i − 1) +<br>2500(j − 1) +<br>50(k − 1) +<br>m + 8050000 | Compound 8050001-14300000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 14300000 | Compound 14300001-14425000 |

| Structure | R₁, R₂, Ar | x equal to | Compound x |
|---|---|---|---|
| (structure) | Ar = Ai<br>R₁ = Rj<br>R₂ = Rk<br>i, j, and k are each independently an integer from 1 to 50 | 2500(i − 1) +<br>50(j − 1) +<br>k + 14425000 | Compound 14425001-14550000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 14550000 | Compound 14550001-14675000 |
| (structure) | Ar = Ai<br>R₁ = Rj<br>R₂ = Rk<br>R₃ = Rm<br>i, j, k and m are each independently an integer from 1 to 50 | 125000(i − 1) +<br>2500(j − 1) +<br>50(k − 1) +<br>m + 14675000 | Compound 14675001-20925000 |
| (structure) | Ar = Ai<br>R₁ = Rj<br>R₂ = Rk<br>R₃ = Rm<br>i, j, k and m are each independently an integer from 1 to 50 | 125000(i − 1) +<br>2500(j − 1) +<br>50(k − 1) +<br>m + 20925000 | Compound 20925001-27175000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 27175000 | Compound 27175001-27300000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 27300000 | Compound 27300001-27425000 |

-continued

| Structure | R₁, R₂, Ar | x equal to | Compound x |
|---|---|---|---|
| | Ar = Ai<br>R₁ = Rj<br>R₂ = Rk<br>i, j, and k are each independently an integer from 1 to 50 | 2500(i − 1) +<br>50(j − 1) +<br>k + 27425000 | Compound<br>27425001-27550000 |
| | Ar = Ai<br>R₁ = Rj<br>R₂ = Rk<br>R₃ = Rm<br>i, j, k and m are each independently an integer from 1 to 50 | 125000(i − 1) +<br>2500(j − 1) +<br>50(k − 1) +<br>m + 27550000 | Compound<br>27550001-33800000 |
| | Ar = Ai<br>R₁ = Rj<br>R₂ = Rk<br>R₃ = Rm<br>i, j, k and m are each independently an integer from 1 to 50 | 125000(i − 1) +<br>2500(j − 1) +<br>50(k − 1) +<br>m + 33800000 | Compound<br>33800001-40050000 |
| | Ar = Ai<br>R₁ = Rj<br>R₂ = Rk<br>i, j, and k are each independently an integer from 1 to 50 | 2500(i − 1) +<br>50(j − 1) +<br>k + 40050000 | Compound<br>40050001-40175000 |
| | Ar = Ai<br>R₁ = Rj<br>R₂ = Rk<br>i, j, and k are each independently an integer from 1 to 50 | 2500(i − 1) +<br>50(j − 1) +<br>k + 40175000 | Compound<br>40175001-40300000 |
| | Ar = Ai<br>R₁ = Rj<br>R₂ = Rk<br>i, j, and k are each independently an integer from 1 to 50 | 2500(i − 1) +<br>50(j − 1) +<br>k + 40300000 | Compound<br>40300001-40425000 |

-continued

| Structure | R₁, R₂, Ar | x equal to | Compound x |
|---|---|---|---|
| | Ar = Ai<br>R₁ = Rj<br>R₂ = Rk<br>R₃ = Rm<br>i, j, k and m are each independently an integer from 1 to 50 | 125000(i − 1) +<br>2500(j − 1) +<br>50(k − 1) +<br>m + 40425000 | Compound<br>40425001-46675000 |
| | Ar = Ai<br>R₁ = Rj<br>R₂ = Rk<br>R₃ = Rm<br>i, j, k and m are each independently an integer from 1 to 50 | 125000(i − 1) +<br>2500(j − 1) +<br>50(k − 1) +<br>m + 46675000 | Compound<br>46675001-52925000 |
| | Ar = Ai<br>R₁ = Rj<br>R₂ = Rk<br>i, j, and k are each independently an integer from 1 to 50 | 2500(i − 1) +<br>50(j − 1) +<br>k + 52925000 | Compound<br>52925001-53050000 |
| | Ar = Ai<br>R₁ = Rj<br>R₂ = Rk<br>i, j, and k are each independently an integer from 1 to 50 | 2500(i − 1) +<br>50(j − 1) +<br>k + 53050000 | Compound<br>53050001-53175000 |
| | Ar = Ai<br>R₁ = Rj<br>R₂ = Rk<br>i, j, and k are each independently an integer from 1 to 50 | 2500(i − 1) +<br>50(j − 1) +<br>k + 53175000 | Compound<br>53175001-53300000 |

-continued

| Structure | R₁, R₂, Ar | x equal to | Compound x |
|---|---|---|---|
| (structure) | Ar = Ai<br>R₁ = Rj<br>R₂ = Rk<br>R₃ = Rm<br>i, j, k and m are each independently an integer from 1 to 50 | 125000(i − 1) +<br>2500(j − 1) +<br>50(k − 1) +<br>m + 53300000 | Compound<br>53300001-59550000 |
| (structure) | Ar = Ai<br>R₁ = Rj<br>R₂ = Rk<br>R₃ = Rm<br>i, j, k and m are each independently an integer from 1 to 50 | 125000(i − 1) +<br>2500(j − 1) +<br>50(k − 1) +<br>m + 59550000 | Compound<br>59550001-65800000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 65800000 | Compound<br>65800001-62925000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 65925000 | Compound<br>65925001-66050000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 66050000 | Compound<br>66050001-66175000 |
| (structure) | Ar = Ai<br>R₁ = Rj<br>R₂ = Rk<br>R₃ = Rm<br>i, j, k and m are each independently an integer from 1 to 50 | 125000(i − 1) +<br>2500(j − 1) +<br>50(k − 1) +<br>m + 66175000 | Compound<br>66175001-72425000 |

-continued

| Structure | R₁, R₂, Ar | x equal to | Compound x |
|---|---|---|---|
| (structure) | Ar = Ai<br>R₁ = Rj<br>R₂ = Rk<br>R₃ = Rm<br>i, j, k and m are each independently an integer from 1 to 50 | 125000(i − 1) +<br>2500(j − 1) +<br>50(k − 1) +<br>m + 72425000 | Compound 72425000-78675000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 78675000 | Compound 78675001-78800000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 78800000 | Compound 78800001-78925000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 78925000 | Compound 78925001-79050000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 79050000 | Compound 79050001-79175000 |
| (structure) | Ar = Ai<br>R₁ = Rj<br>R₂ = Rk<br>R₃ = Rm<br>i, j, k and m are each independently an integer from 1 to 50 | 125000(i − 1) +<br>2500(j − 1) +<br>50(k − 1) +<br>m + 79175000 | Compound 79175001-85425000 |

| Structure | R₁, R₂, Ar | x equal to | Compound x |
| --- | --- | --- | --- |
| (structure) | Ar = Ai<br>R₁ = Rj<br>R₂ = Rk<br>R₃ = Rm<br>i, j, k and m are each independently an integer from 1 to 50 | 125000(i − 1) +<br>2500(j − 1) +<br>50(k − 1) +<br>m + 85425000 | Compound 85425001-91675000 |
| (structure) | Ar = Ai<br>R₁ = Rj<br>R₂ = Rk<br>R₃ = Rm<br>i, j, k and m are each independently an integer from 1 to 50 | 125000(i − 1) +<br>2500(j − 1) +<br>50(k − 1) +<br>m + 91675000 | Compound 91675001-97925000 |
| (structure) | Ar = Ai<br>R₁ = Rj<br>R₂ = Rk<br>R₃ = Rm<br>i, j, k and m are each independently an integer from 1 to 50 | 125000(i − 1) +<br>2500(j − 1) +<br>50(k − 1) +<br>m + 97925000 | Compound 97925001-104175000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 104175000 | Compound 104175001-104300000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 104300000 | Compound 104300001-104425000 |
| (structure) | Ar = Ai<br>R₁ = Rj<br>R₂ = Rk<br>i, j, and k are each independently an integer from 1 to 50 | 2500(i − 1) +<br>50(j − 1) +<br>k + 104425000 | Compound 104425001-104550000 |

-continued

| Structure | $R_1$, $R_2$, Ar | x equal to | Compound x |
|---|---|---|---|
| 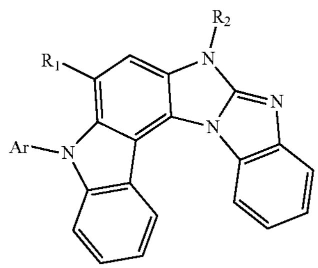 | Ar = Ai<br>$R_1$ = Rj<br>$R_2$ = Rk<br>i, j, and k are each independently an integer from 1 to 50 | 2500(i − 1) +<br>50(j − 1) +<br>k + 104550000 | Compound<br>104550001-104675000 |
| | Ar = Ai<br>$R_1$ = Rj<br>$R_2$ = Rk<br>$R_3$ = Rm<br>i, j, k and m are each independently an integer from 1 to 50 | 125000(i − 1) +<br>2500(j − 1) +<br>50(k − 1) +<br>m + 104675000 | Compound<br>104675001-110925000 |
| | Ar = Ai<br>$R_1$ = Rj<br>$R_2$ = Rk<br>$R_3$ = Rm<br>i, j, k and m are each independently an integer from 1 to 50 | 125000(i − 1) +<br>2500(j − 1) +<br>50(k − 1) +<br>m + 110925000 | Compound<br>110925001-117175000 |
| | Ar = Ai<br>$R_1$ = Rj<br>$R_2$ = Rk<br>$R_3$ = Rm<br>i, j, k and m are each independently an integer from 1 to 50 | 125000(i − 1) +<br>2500(j − 1) +<br>50(k − 1) +<br>m + 117175000 | Compound<br>117175001-123425000 |
| | Ar = Ai<br>$R_1$ = Rj<br>$R_2$ = Rk<br>$R_3$ = Rm<br>i, j, k and m are each independently an integer from 1 to 50 | 125000(i − 1) +<br>2500(j − 1) +<br>50(k − 1) +<br>m + 123425000 | Compound<br>123425001-129675000 |

-continued

| Structure | R₁, R₂, Ar | x equal to | Compound x |
|---|---|---|---|
| | Ar = Ai<br>R₁ = Rj<br>R₂ = Rk<br>i, j, and k are each independently an integer from 1 to 50 | 2500(i − 1) +<br>50(j − 1) +<br>k + 129675000 | Compound<br>129675001-129800000 |
| | Ar = Ai<br>R₁ = Rj<br>R₂ = Rk<br>i, j, and k are each independently an integer from 1 to 50 | 2500(i − 1) +<br>50(j − 1) +<br>k + 129800000 | Compound<br>129800001-129925000 |
| | Ar = Ai<br>R₁ = Rj<br>R₂ = Rk<br>i, j, and k are each independently an integer from 1 to 50 | 2500(i − 1) +<br>50(j − 1) +<br>k + 129925000 | Compound<br>129925001-130050000 |
| | Ar = Ai<br>R₁ = Rj<br>R₂ = Rk<br>i, j, and k are each independently an integer from 1 to 50 | 2500(i − 1) +<br>50(j − 1) +<br>k + 130050000 | Compound<br>130050001-130175000 | wherein A1 to A50 have the following structures:

A1

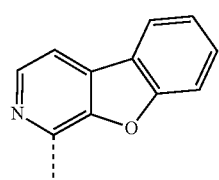

A2

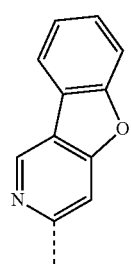

-continued

A3

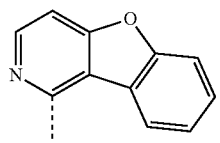

A4

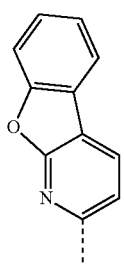

-continued
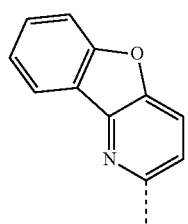
A5
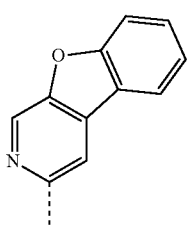
A6
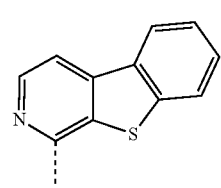
A7
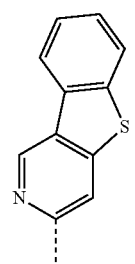
A8
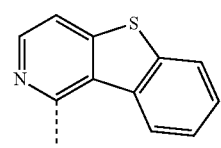
A9
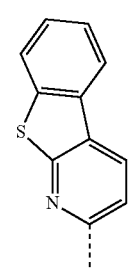
A10
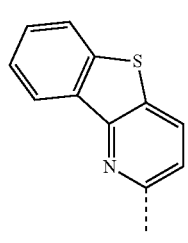
A11
-continued
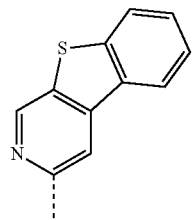
A12
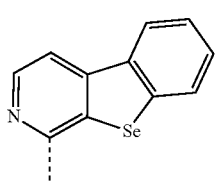
A13
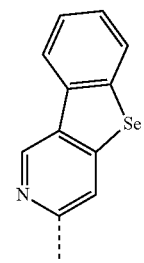
A14
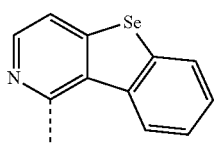
A15
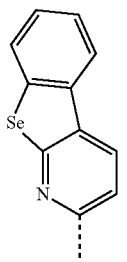
A16
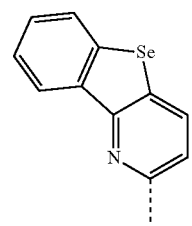
A17
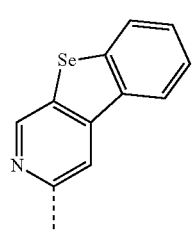
A18

| | |
|---|---|
| A19 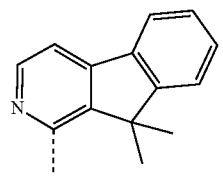 | A26 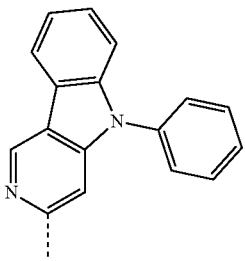 |
| A20 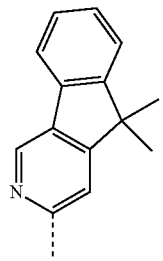 | A27 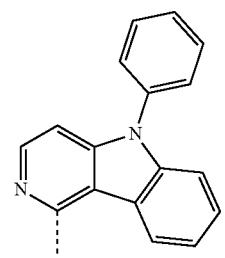 |
| A21 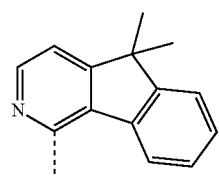 | A28 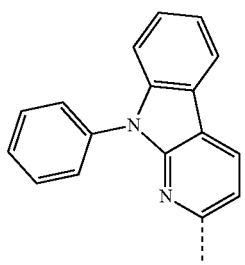 |
| A22 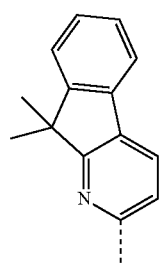 | A29 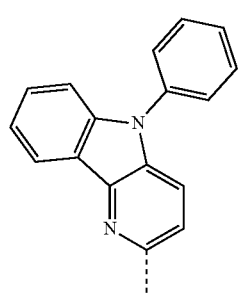 |
| A23 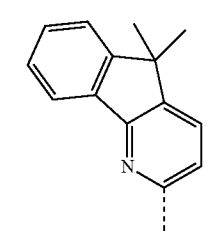 | A30 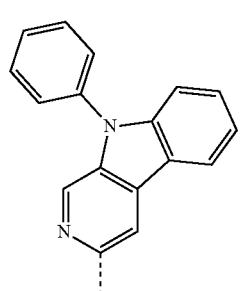 |
| A24 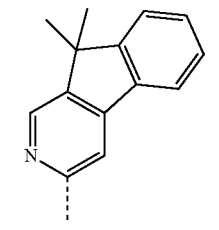 | A31 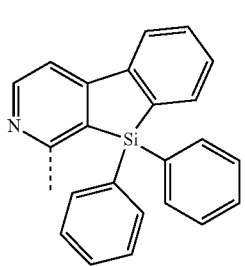 |
| A25 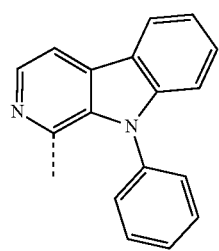 | |

-continued
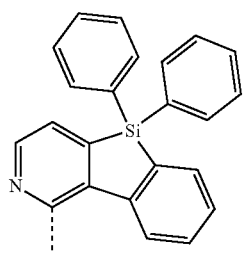
A32
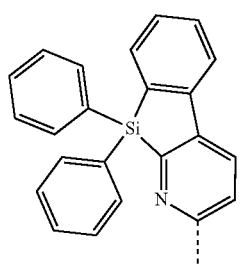
A33
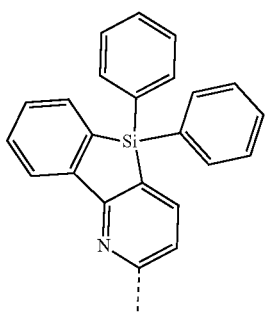
A34
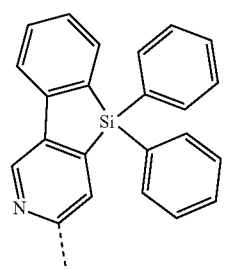
A35
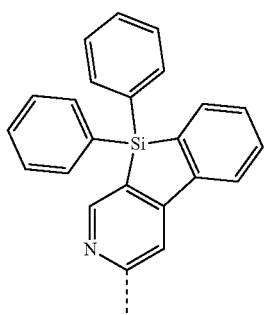
A36
-continued
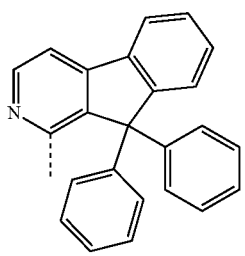
A37
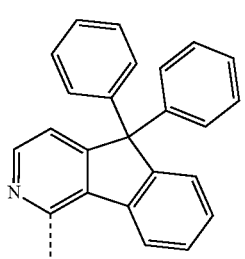
A38
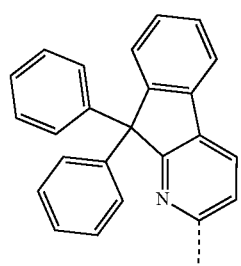
A39
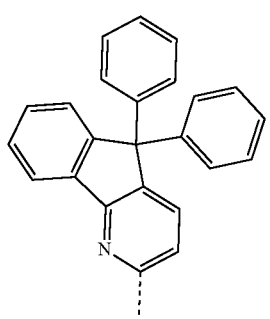
A40
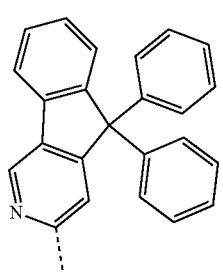
A41

A42 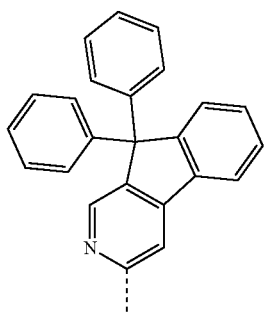
A43 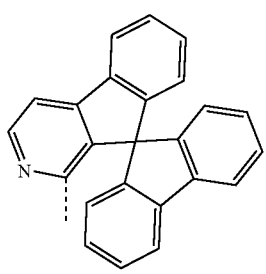
A44 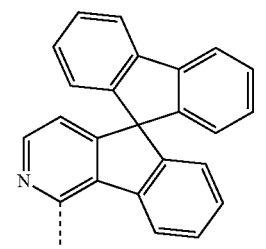
A45 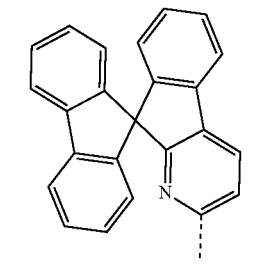
A46 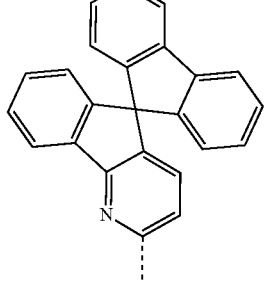
A47 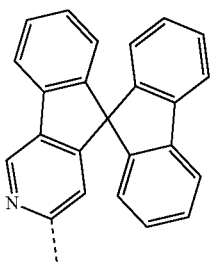
A48 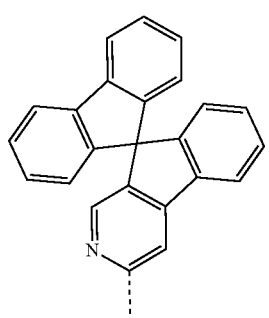
A49 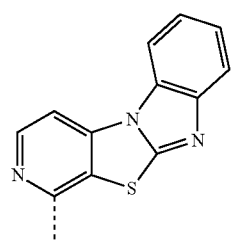
A50 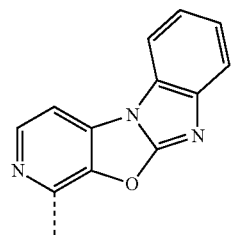
and wherein R5 to R15 and R17 to R50 have the following structures:
R: R5 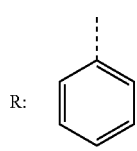
R6 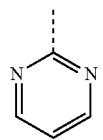

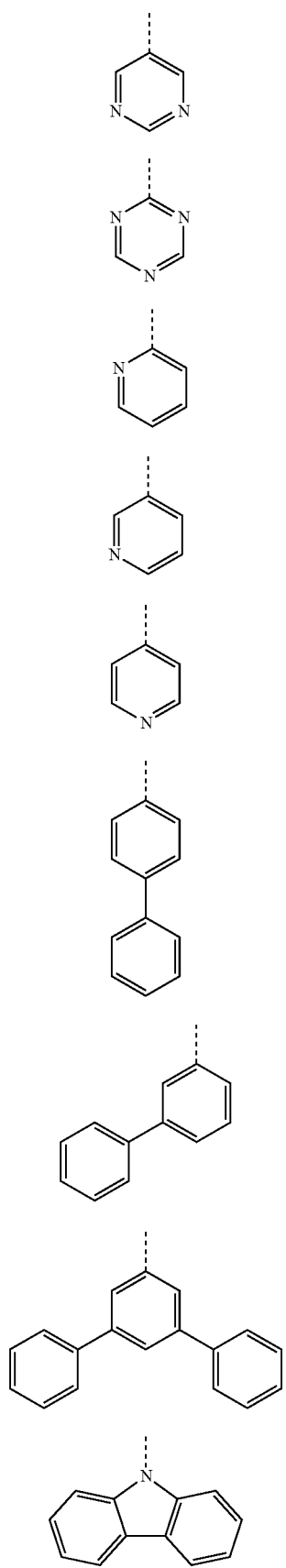
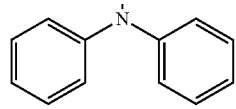
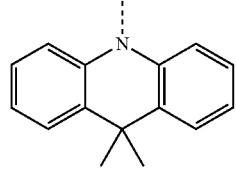
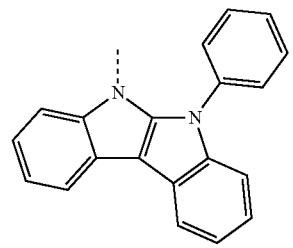
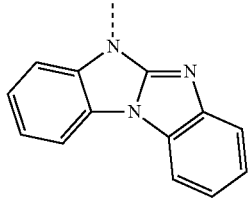
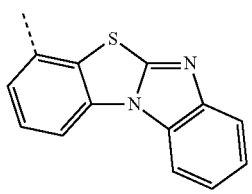
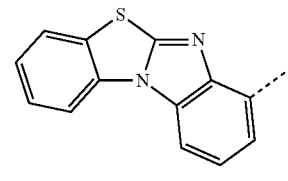
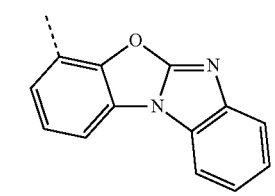
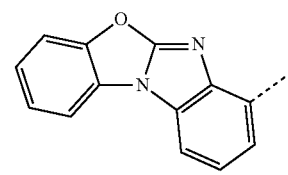

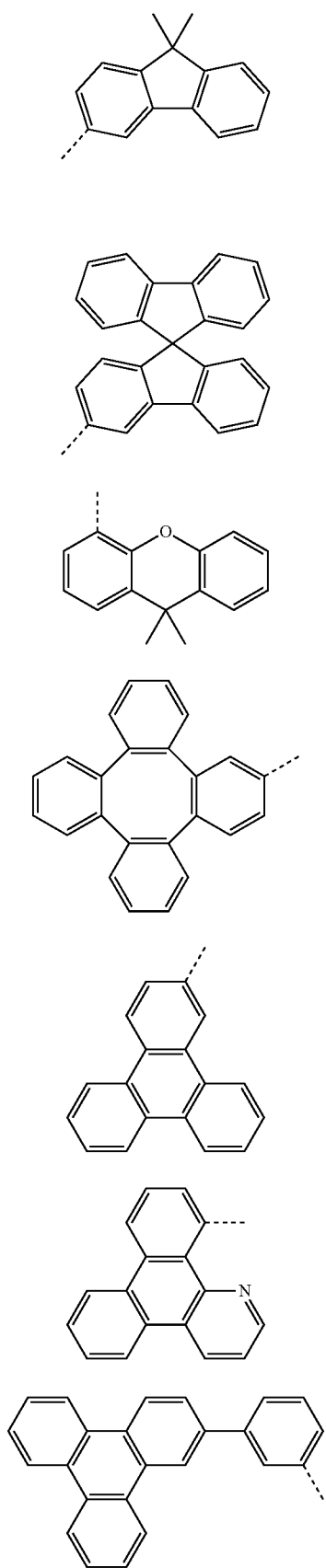
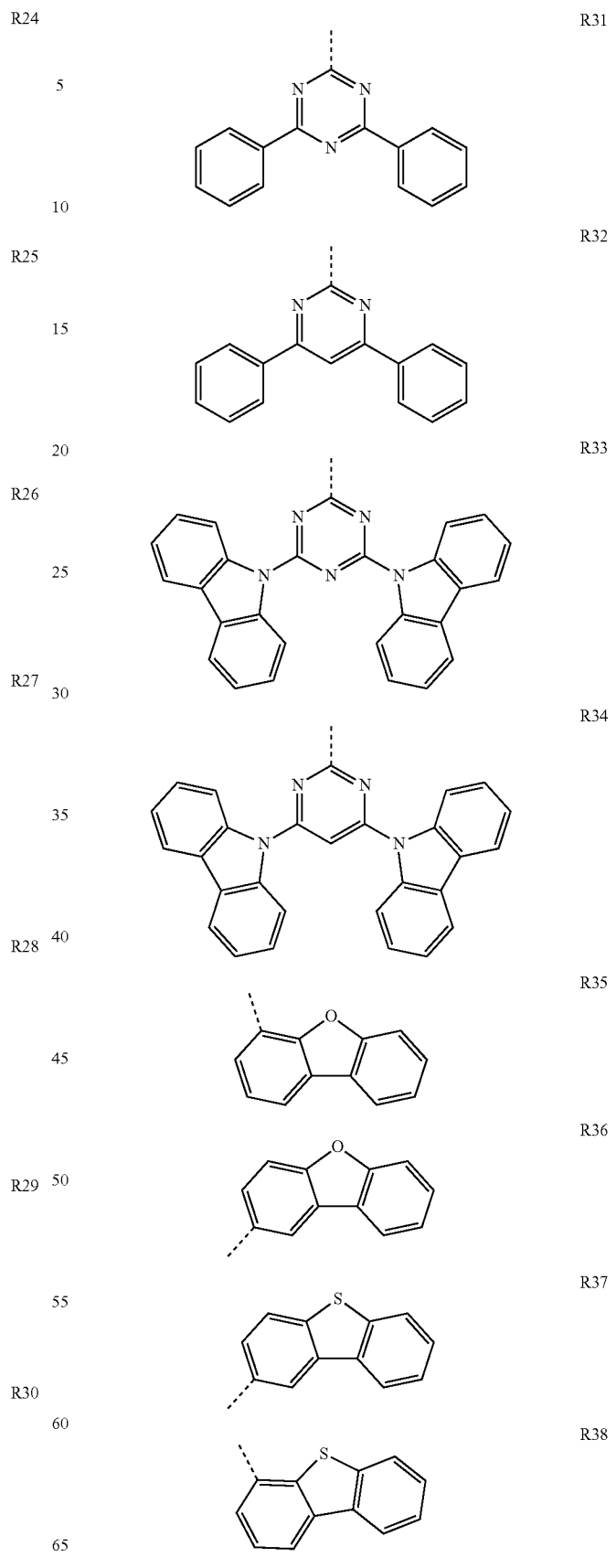

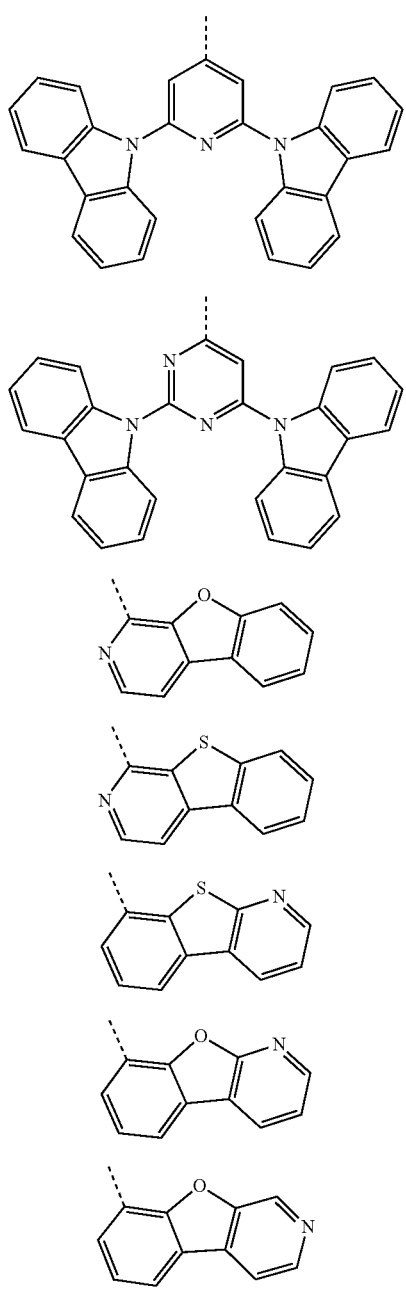
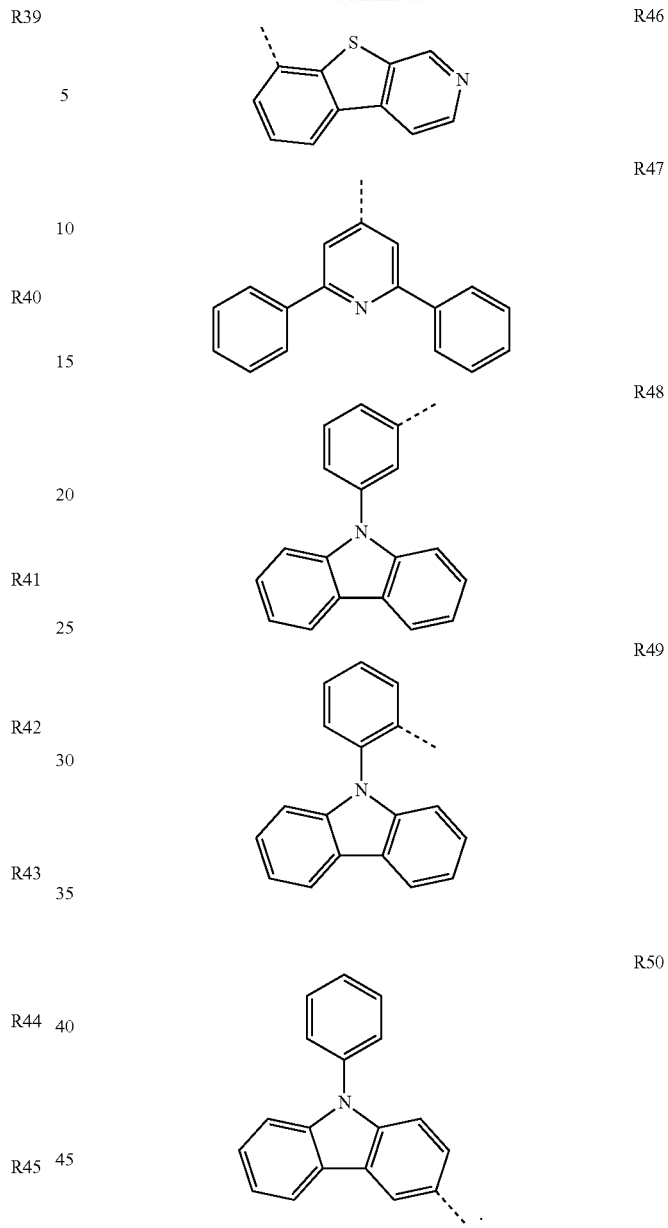
12. The compound of claim 1, wherein the compound is selected from the group consisting of:
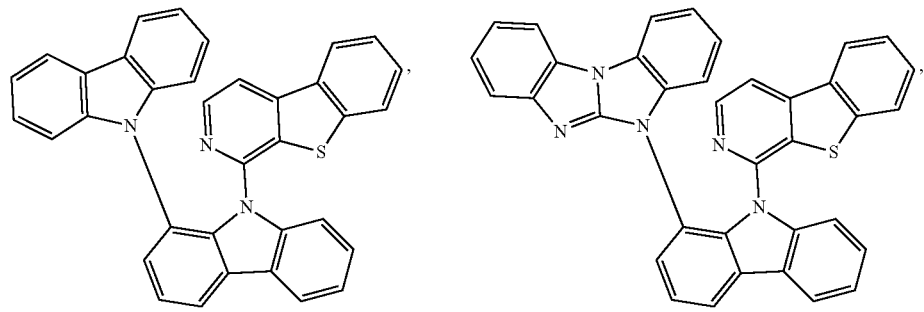

223 224
-continued
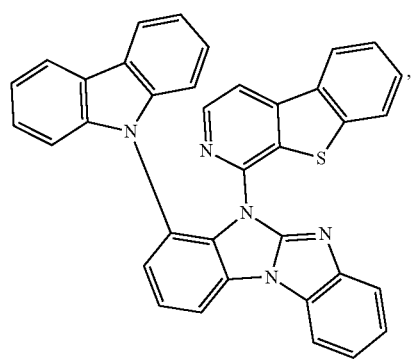 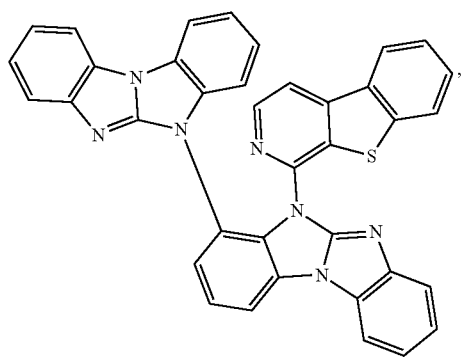
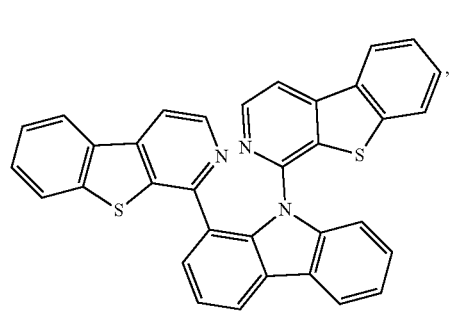 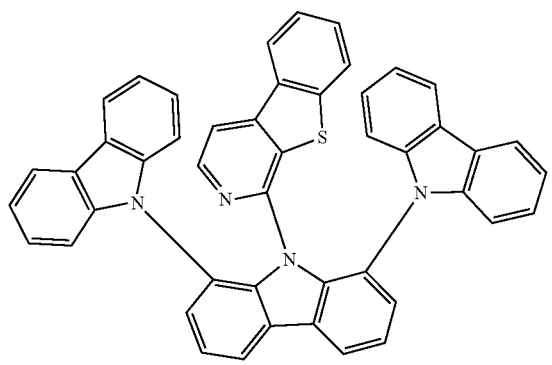
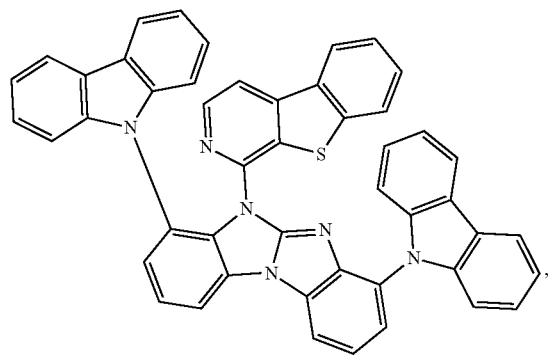 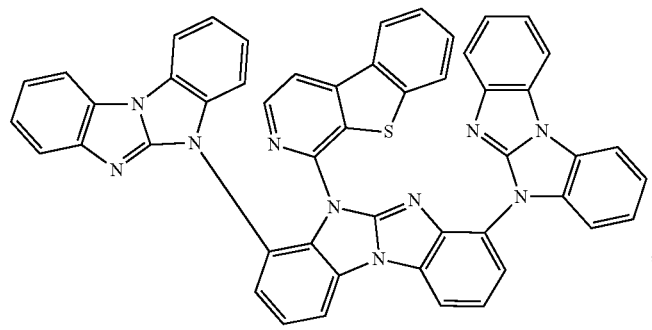
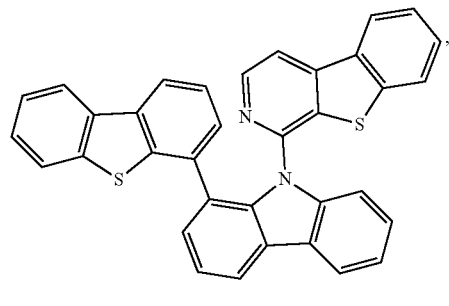 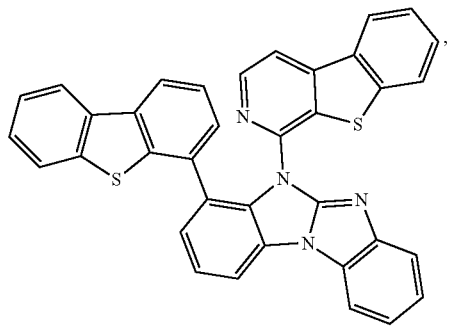

-continued
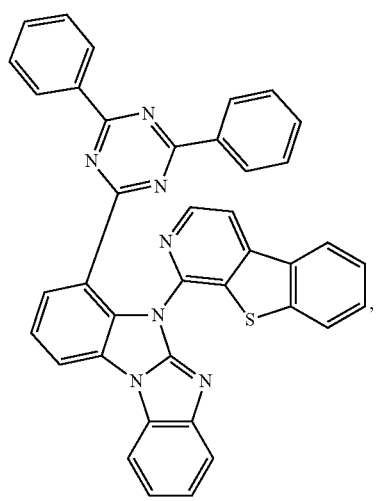
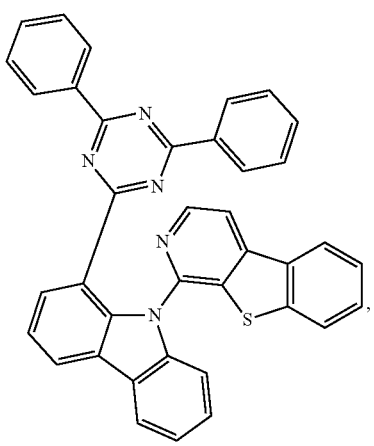
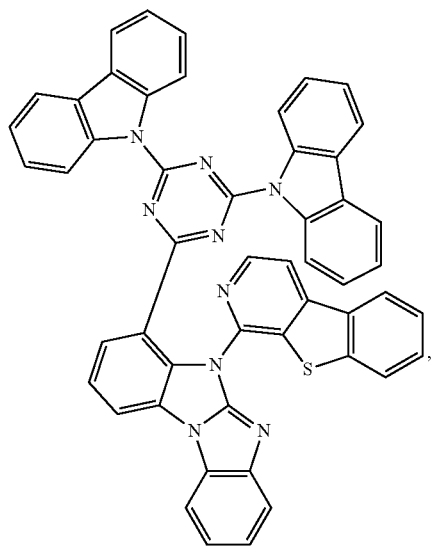
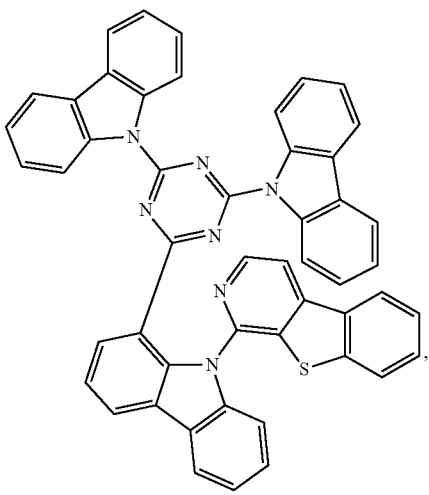
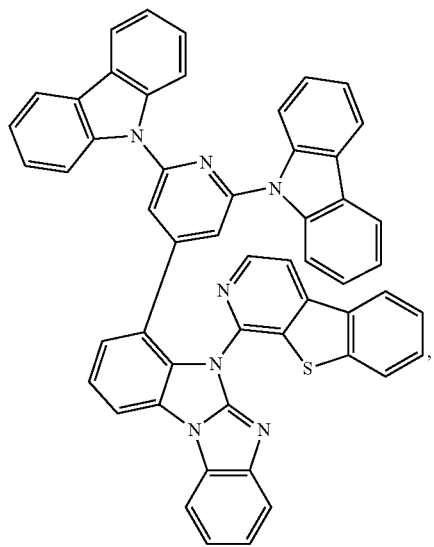
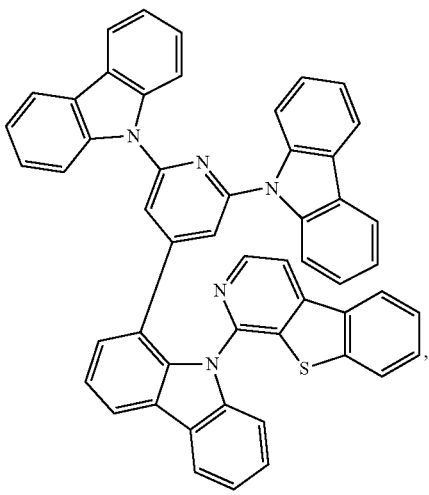

-continued
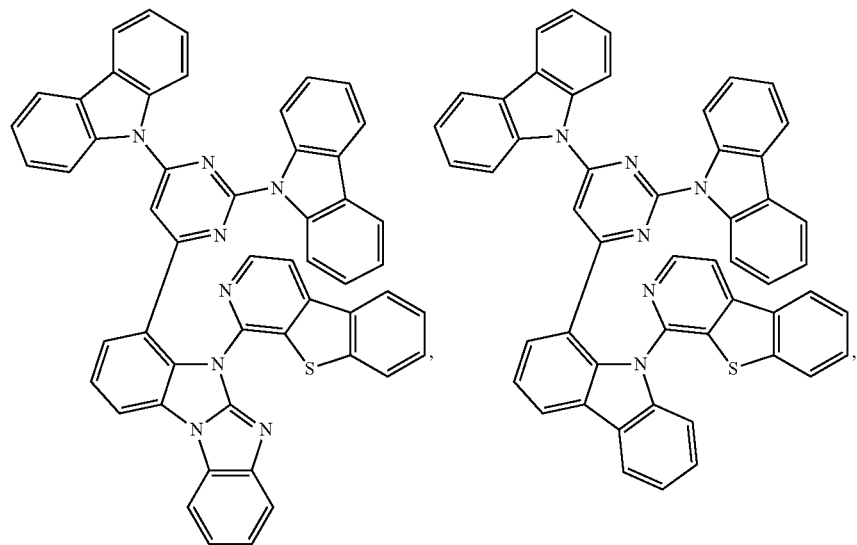
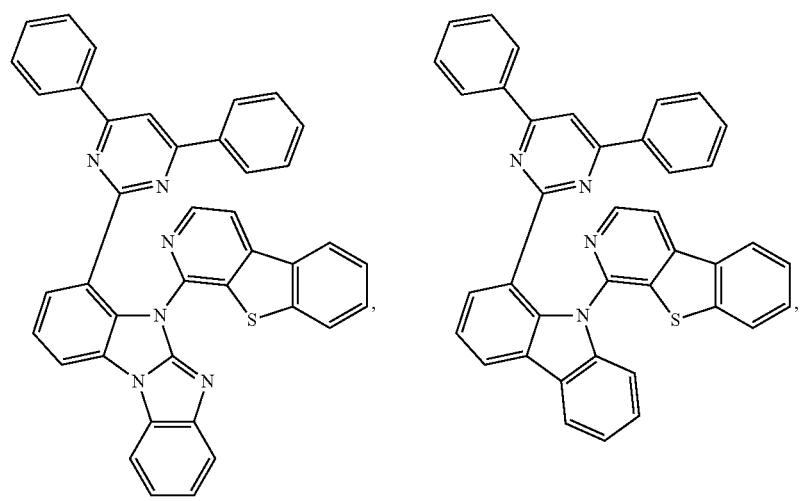
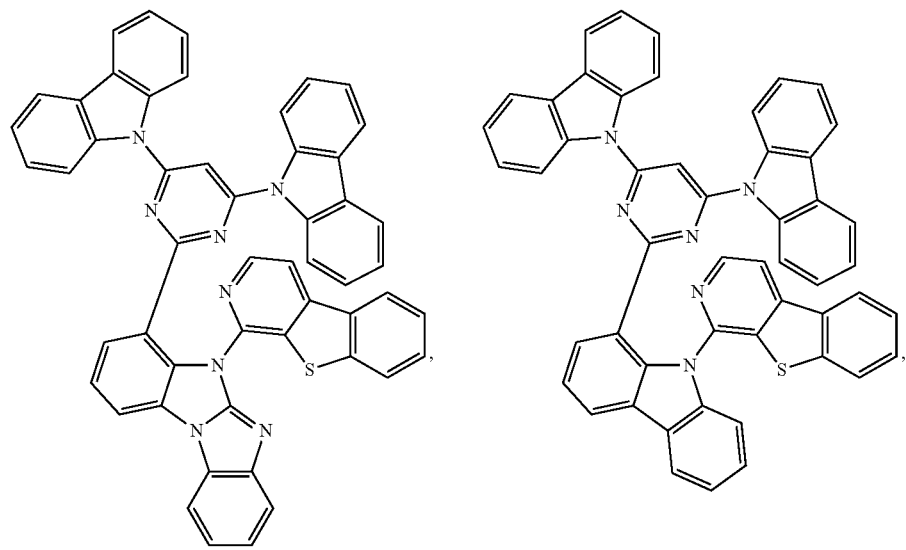

-continued
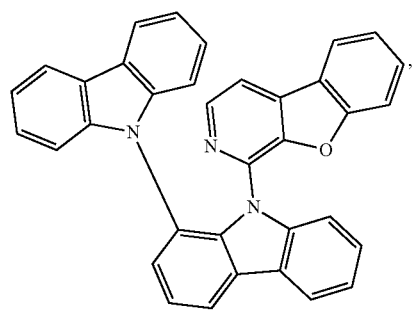
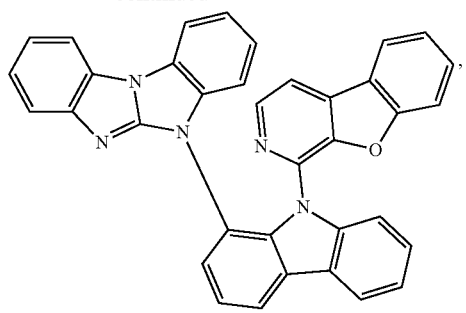
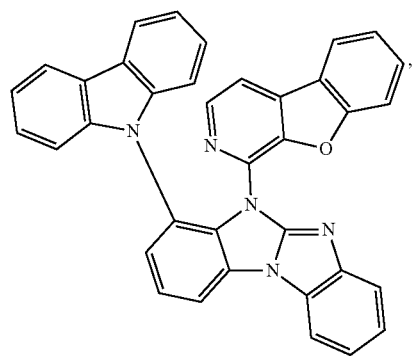
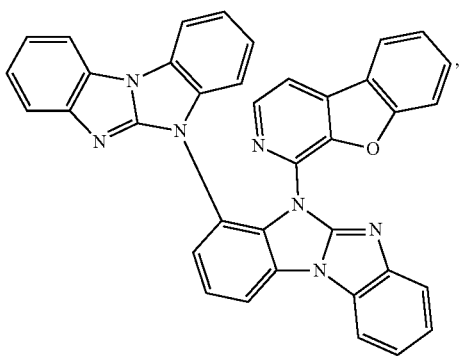
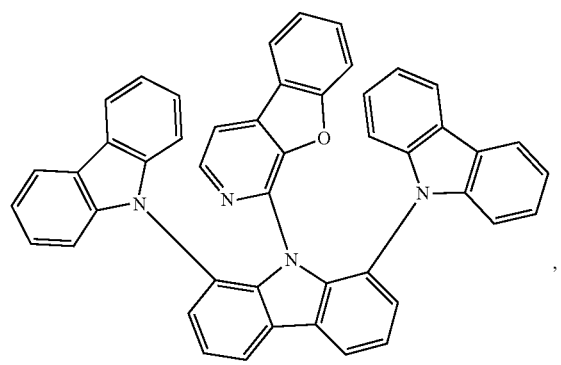
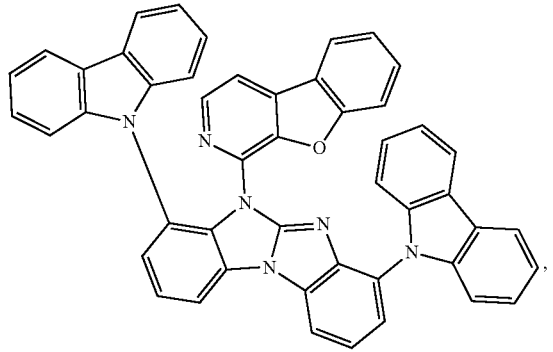
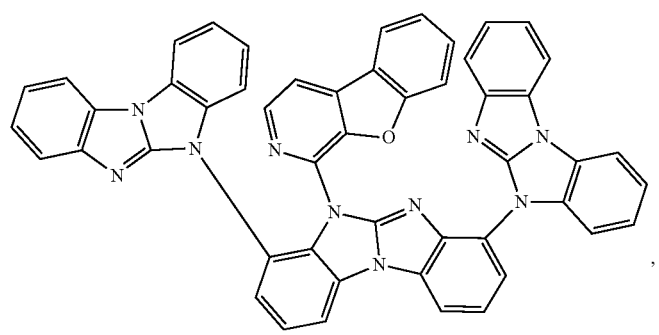
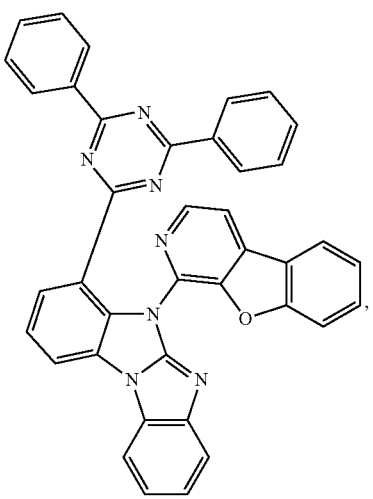

-continued
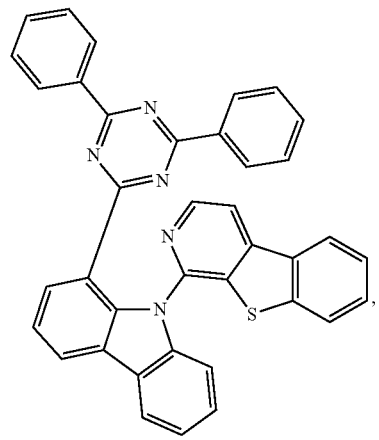
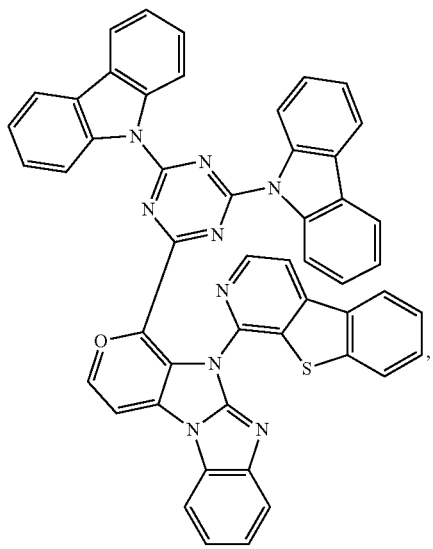
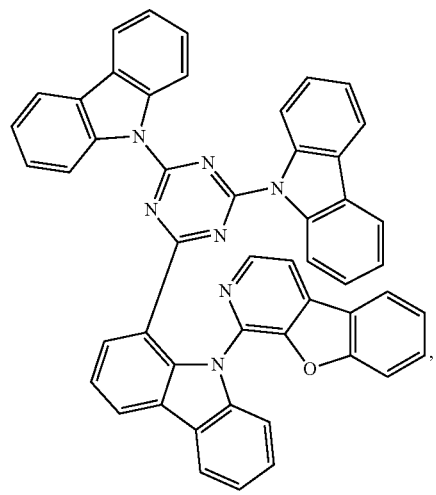
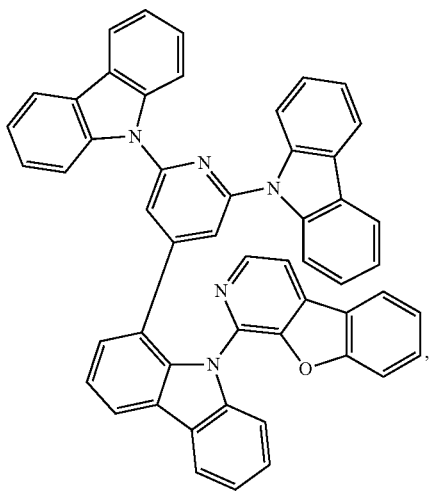
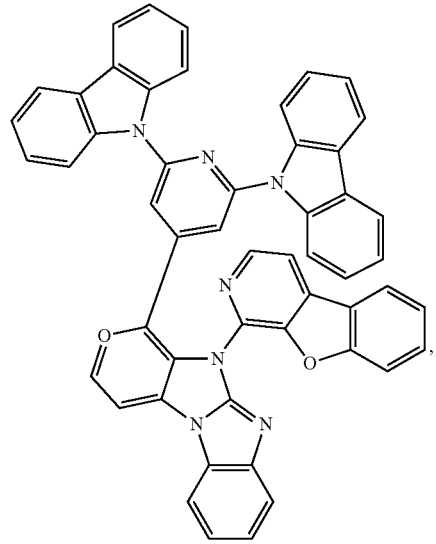
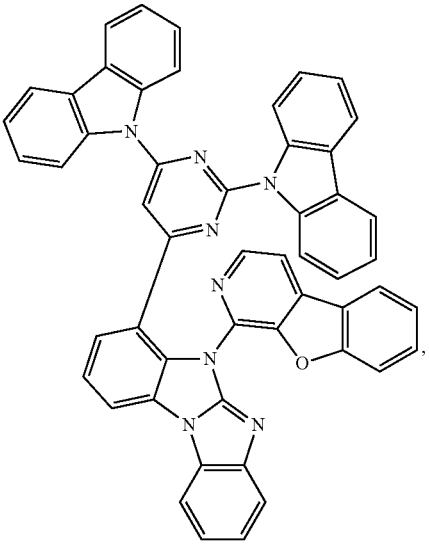

-continued
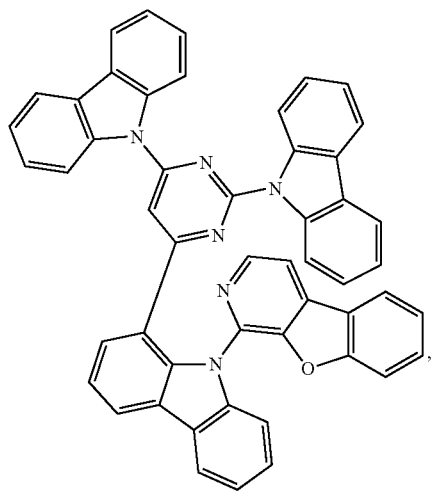
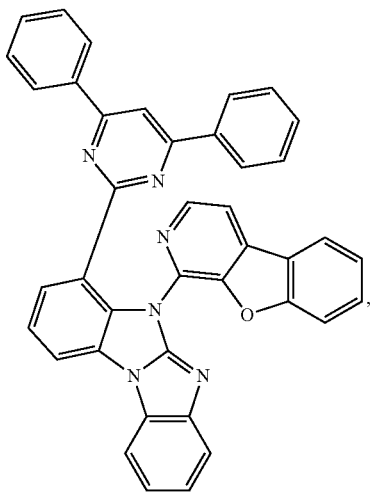
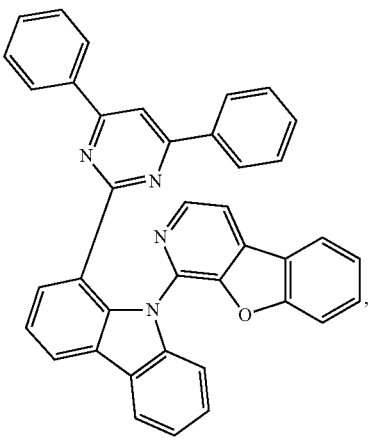
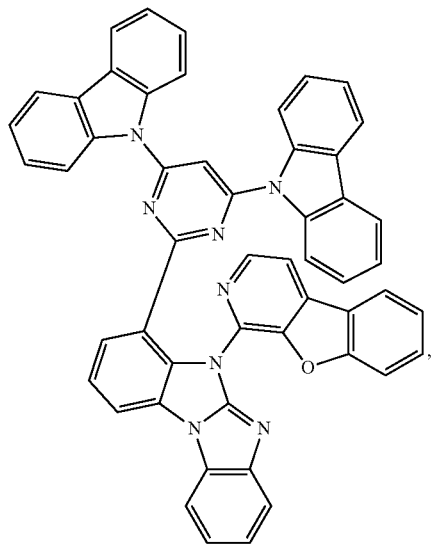
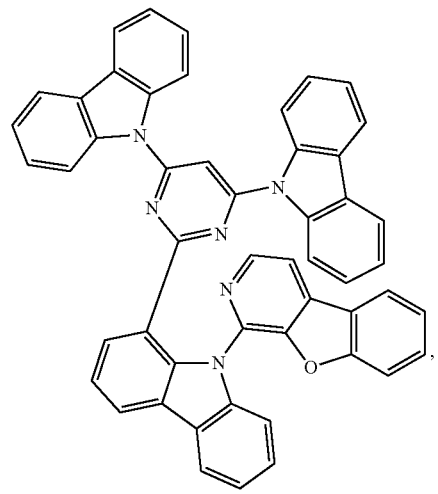
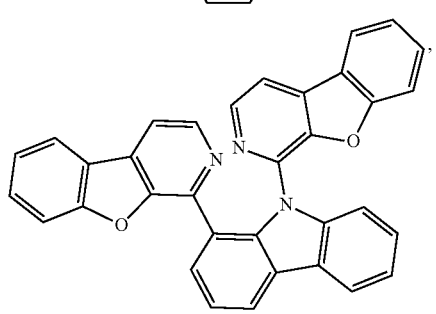
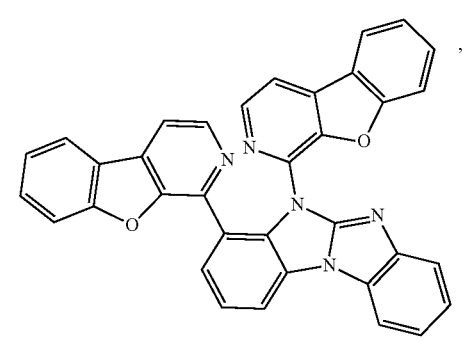
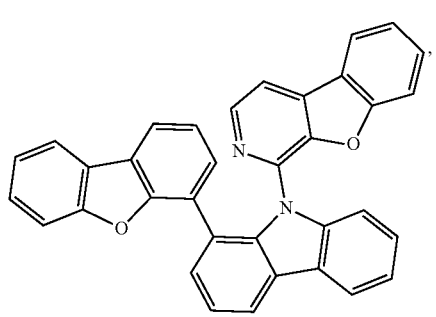
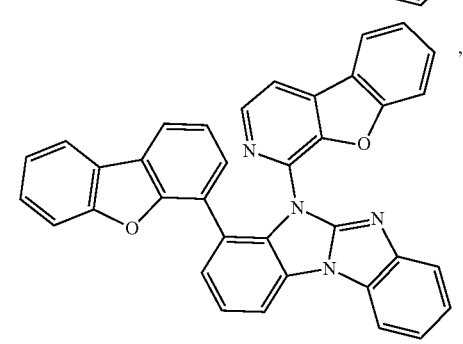

-continued

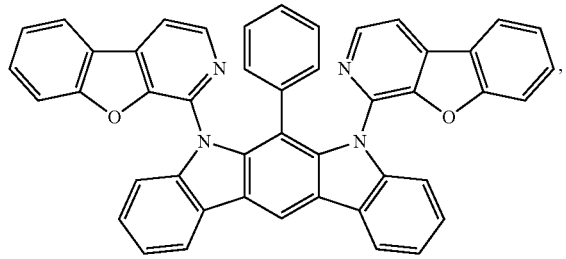
,

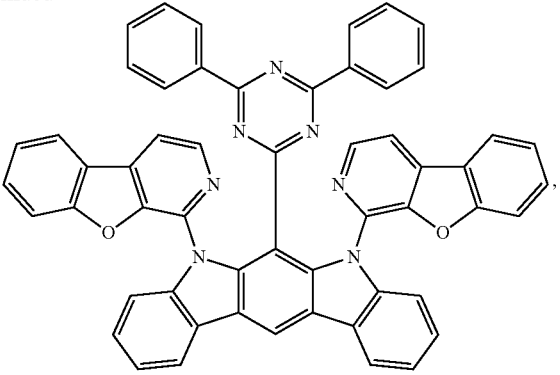
,

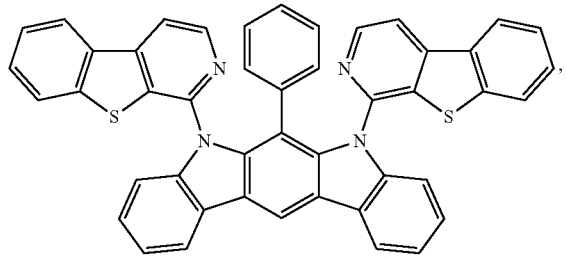
,

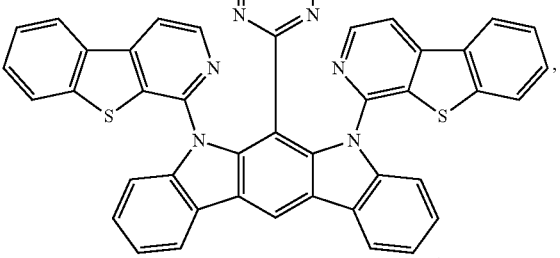
,

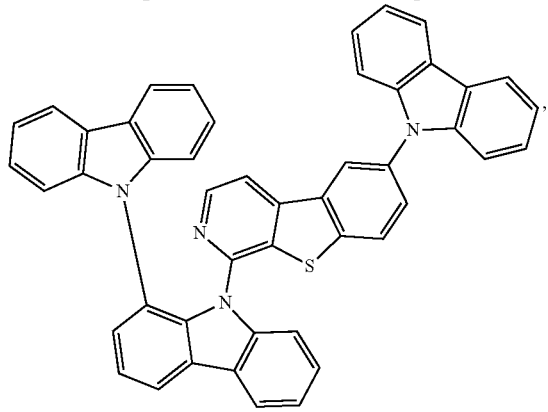
, and

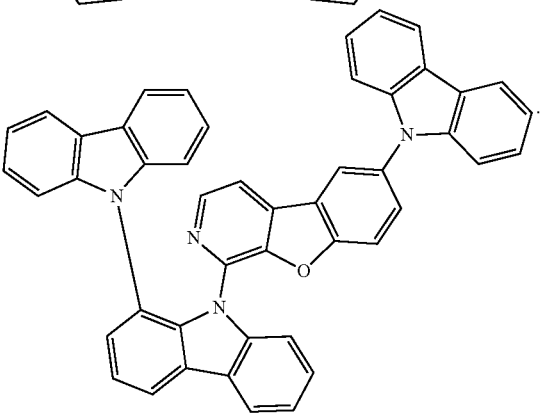
.

13. An organic light emitting device (OLED) comprising an anode, a cathode, and an organic layer disposed between the anode and the cathode, the organic layer comprising a compound according to Formula II:

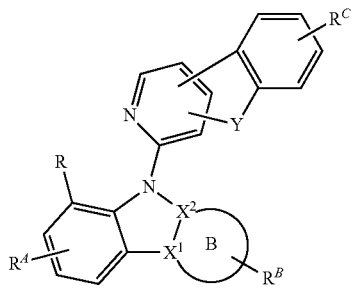

Formula II wherein
ring B is a 5-membered heterocyclic ring or a 6-membered carbocyclic ring;
$X^1$ and $X^2$ are independently $CR^X$ or N, and at least one of $X^1$ or $X^2$ is $CR^X$;
Y is selected from the group consisting of O, S, Se, NR', BR', CR'R", and SiR'R";
R', and R" are each independently selected from the group consisting of alkyl, cycloalkyl, heteroalkyl, heterocycloalkyl, aryl, heteroaryl, and combinations thereof;
R is a substituted or unsubstituted aryl or heteroaryl;
$R^A$, $R^B$, and $R^C$ each independently represent mono to the maximum allowable substitution, or no substitution; and
each $R^X$, $R^A$, $R^B$, and $R^C$ is independently a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof, and wherein any two substituents $R^X$, $R^A$, $R^B$, and $R^C$ may be optionally joined to form a ring, with the proviso that R does not join with $R^A$ to form a ring.

14. The OLED of claim 13, wherein the organic layer is an emissive layer and includes a compound according to Formula I, the compound being a host compound.

15. The OLED of claim 13, wherein the organic layer further comprises a phosphorescent emissive dopant; wherein the emissive dopant is a transition metal complex having at least one ligand or part of the ligand if the ligand is more than bidentate selected from the group consisting of:

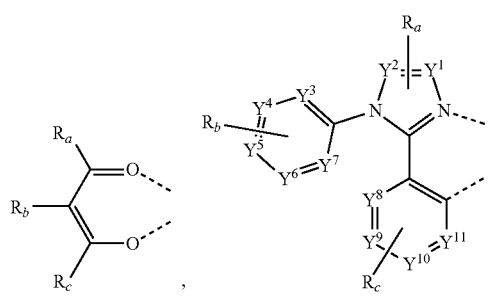

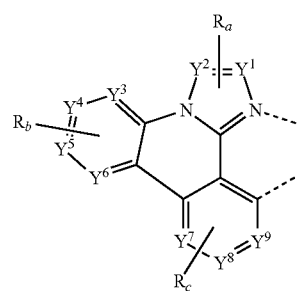

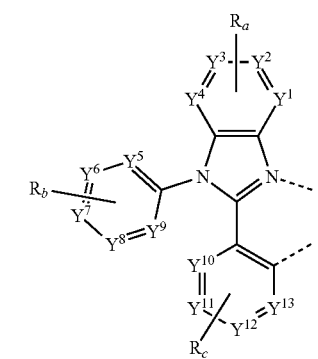

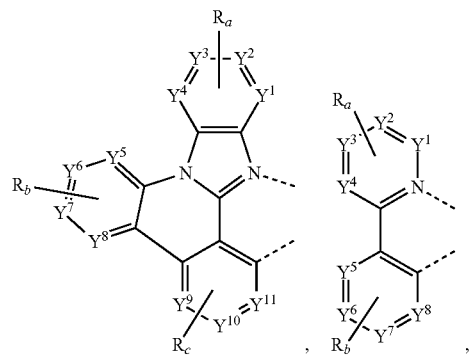

-continued

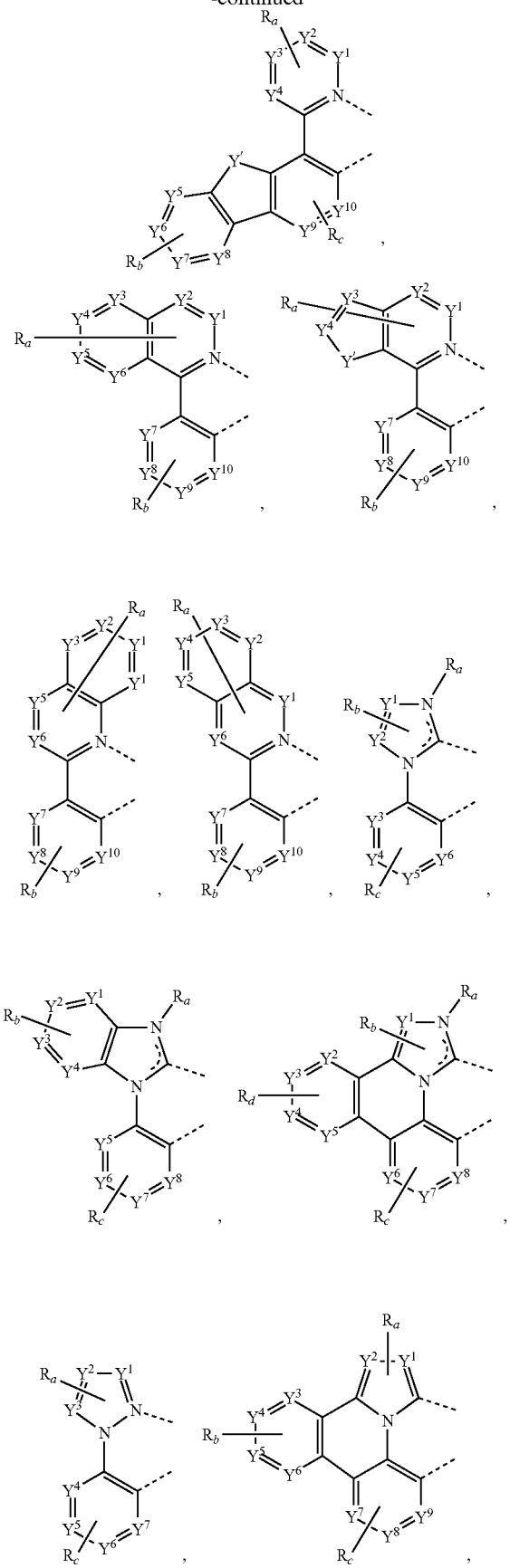

-continued

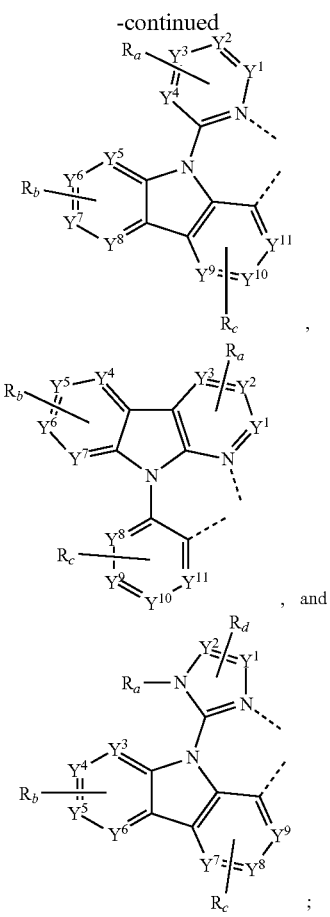

wherein
each $Y^1$ to $Y^{13}$ is independently selected from C or N;
Y' is selected from the group consisting of $BR_e$, $NR_e$, $PR_e$, O, S, Se, C=O, S=O, $SO_2$, $CR_eR_f$, $SiR_eR_f$, and $GeR_eR_f$;
$R_a$, $R_b$, $R_c$, and $R_d$ independently represent from mono substitution to the maximum possible number of substitution, or no substitution; each $R_a$, $R_b$, $R_c$, $R_d$, $R_e$ and $R_f$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and any two adjacent substituents $R_a$, $R_b$, $R_c$, and $R_d$ may optionally be joined to form a ring or form a multidentate ligand; and $R_e$ and $R_f$ may optionally be joined to form a ring.

16. The OLED of claim 13, wherein the organic layer is a blocking layer and the compound according to Formula I is a blocking material in the organic layer, or the organic layer is a transporting layer and the compound according to Formula I is a transporting material in the organic layer.

17. A consumer product comprising an organic light-emitting device (OLED) comprising an anode, a cathode, and an organic layer disposed between the anode and the cathode, the organic layer comprising a compound according Formula II:

Formula II

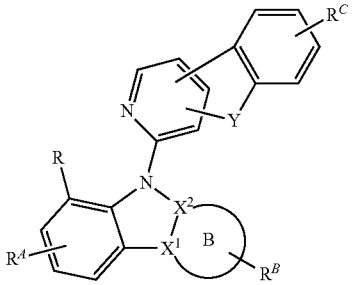

wherein
ring B is a 5-membered heterocyclic ring or a 6-membered carbocyclic ring;
$X^1$ and $X^2$ are independently $CR^X$ or N, and at least one of $X^1$ or $X^2$ is $CR^X$;
Y is selected from the group consisting of O, S, Se, NR', BR', CR'R", and SiR'R";
R', and R" are each independently selected from the group consisting of alkyl, cycloalkyl, heteroalkyl, heterocycloalkyl, aryl, heteroaryl, and combinations thereof;
R is a substituted or unsubstituted aryl or heteroaryl;
$R^A$, $R^B$, and $R^C$ each independently represent mono to the maximum allowable substitution, or no substitution; and
each $R^X$, $R^A$, $R^B$, and $R^C$ is independently a hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof, and wherein any two substituents $R^X$, $R^A$, $R^B$, and $R^C$ may be optionally joined to form a ring, with the proviso that R does not join with $R^A$ to form a ring.

18. A formulation comprising a compound according to claim 1.

* * * * *